United States Patent
Sommadossi et al.

(10) Patent No.: US 7,582,618 B2
(45) Date of Patent: *Sep. 1, 2009

(54) 2'-C-METHYL-3'-O-L-VALINE ESTER RIBOFURANOSYL CYTIDINE FOR TREATMENT OF FLAVIVIRIDAE INFECTIONS

(75) Inventors: Jean-Pierre Sommadossi, Cambridge, MA (US); Paolo LaColla, Capoterra (IT); Gilles Gosselin, Montpellier (FR)

(73) Assignees: Idenix Pharmaceuticals, Inc., Cambridge, MA (US); University of Cagliari, Cagliari (IT); Centre National de la Recherche Scientifique, Paris (FR); L'Universite Montpellier II, Montpellier (FR)

( * ) Notice: Subject to any disclaimer, the term of this patent is extended or adjusted under 35 U.S.C. 154(b) by 88 days.

This patent is subject to a terminal disclaimer.

(21) Appl. No.: 11/516,928

(22) Filed: Sep. 6, 2006

(65) Prior Publication Data

US 2007/0275883 A1 Nov. 29, 2007

Related U.S. Application Data

(63) Continuation of application No. 10/607,909, filed on Jun. 27, 2003, now Pat. No. 7,456,155.

(60) Provisional application No. 60/392,351, filed on Jun. 28, 2002.

(51) Int. Cl.
*A01N 43/04* (2006.01)
*A61K 31/70* (2006.01)

(52) U.S. Cl. .............................. 514/49; 514/25; 514/42; 514/43; 514/44; 514/50

(58) Field of Classification Search ........................ None
See application file for complete search history.

(56) References Cited

U.S. PATENT DOCUMENTS

| | | | |
|---|---|---|---|
| 3,074,929 A | 1/1963 | Hitchings et al. |
| 3,116,282 A | 12/1963 | Hunter |
| 3,480,613 A | 11/1969 | Walton |
| 3,798,209 A | 3/1974 | Wilkowski et al. |
| 3,891,623 A | 6/1975 | Vorbruggen et al. |
| 4,022,889 A | 5/1977 | Bannister et al. |
| 4,058,602 A | 11/1977 | Beisler et al. |
| RE29,835 E | 11/1978 | Witkowski et al. |
| 4,209,613 A | 6/1980 | Vorbruggen et al. |
| 4,239,753 A | 12/1980 | Skulnick et al. |
| 4,294,766 A | 10/1981 | Schmidt et al. |
| 4,522,811 A | 6/1985 | Eppstein et al. |
| 4,605,659 A | 8/1986 | Verheyden et al. |
| 4,689,404 A | 8/1987 | Kawada et al. |
| 4,754,026 A | 6/1988 | Kawada et al. |
| 4,814,477 A | 3/1989 | Wijnberg et al. |
| 4,880,784 A | 11/1989 | Robins et al. |
| 4,952,740 A | 8/1990 | Juge et al. |
| 4,957,924 A | 9/1990 | Beauchamp |
| 5,034,394 A | 7/1991 | Daluge |
| 5,122,517 A | 6/1992 | Vince et al. |
| 5,149,794 A | 9/1992 | Yatvin et al. |
| 5,157,027 A | 10/1992 | Biller et al. |
| 5,194,654 A | 3/1993 | Hostetler et al. |
| 5,200,514 A | 4/1993 | Chu |
| 5,223,263 A | 6/1993 | Hostetler et al. |
| 5,246,924 A | 9/1993 | Fox et al. |
| 5,256,641 A | 10/1993 | Yatvin et al. |
| 5,322,955 A | 6/1994 | Matsumoto et al. |
| 5,371,210 A | 12/1994 | Chou |
| 5,372,808 A | 12/1994 | Blatt et al. |
| 5,391,769 A | 2/1995 | Matsumoto et al. |
| 5,401,861 A | 3/1995 | Chou |
| 5,411,947 A | 5/1995 | Hostetler et al. |
| 5,463,092 A | 10/1995 | Hostetler et al. |
| 5,539,116 A | 7/1996 | Liotta et al. |
| 5,543,389 A | 8/1996 | Yatvin et al. |
| 5,543,390 A | 8/1996 | Yatvin et al. |
| 5,543,391 A | 8/1996 | Yatvin et al. |
| 5,554,728 A | 9/1996 | Basava et al. |
| 5,565,438 A | 10/1996 | Chu et al. |

(Continued)

FOREIGN PATENT DOCUMENTS

CA 2252144 4/2000

(Continued)

OTHER PUBLICATIONS

Baginski, S. G, et al., "Mechanism of action of a pestivirus antiviral compound," *PNAS USA*, 97(14) : 7981-7986 (2000).

(Continued)

*Primary Examiner*—Traviss C McIntosh, III
(74) *Attorney, Agent, or Firm*—Jones Day

(57) ABSTRACT

The 3'-L-valine ester of β-D-2'-C-methyl-ribofuranosyl cytidine provides superior results against flaviviruses and pestiviruses, including hepatitis C virus. Based on this discovery, compounds, compositions, methods and uses are provided for the treatment of flaviviridae, including HCV, that include the administration of an effective amount of val-mCyd or its salt, ester, prodrug or derivative, optionally in a pharmaceutically acceptable carrier. In an alternative embodiment, val-mCyd is used to treat any virus that replicates through an RNA-dependent RNA polymerase.

36 Claims, 12 Drawing Sheets

U.S. PATENT DOCUMENTS

| | | |
|---|---|---|
| 5,567,688 A | 10/1996 | Chu et al. |
| 5,587,362 A | 12/1996 | Chu et al. |
| 5,606,048 A | 2/1997 | Chou et al. |
| 5,676,942 A | 10/1997 | Testa et al. |
| 5,696,277 A | 12/1997 | Hostetler et al. |
| 5,738,845 A | 4/1998 | Imakawa |
| 5,744,600 A | 4/1998 | Mansuri et al. |
| 5,750,676 A | 5/1998 | Vorbruggen et al. |
| 5,763,418 A | 6/1998 | Matsuda et al. |
| 5,780,617 A | 7/1998 | van den Bosch et al. |
| 5,789,608 A | 8/1998 | Glazier |
| 5,821,357 A | 10/1998 | Chou et al. |
| 5,830,455 A | 11/1998 | Valtuena et al. |
| 5,849,696 A | 12/1998 | Chretien et al. |
| 5,908,621 A | 6/1999 | Glue et al. |
| 5,928,636 A | 7/1999 | Alber et al. |
| 5,942,223 A | 8/1999 | Bazer et al. |
| 5,977,061 A | 11/1999 | Holy et al. |
| 5,977,325 A | 11/1999 | McCarthy et al. |
| 5,980,884 A | 11/1999 | Blatt et al. |
| 6,002,029 A | 12/1999 | Hostetler et al. |
| 6,063,628 A | 5/2000 | Loeb et al. |
| 6,140,310 A | 10/2000 | Glazier |
| 6,153,594 A | 11/2000 | Borretzen et al. |
| 6,156,501 A | 12/2000 | McGall et al. |
| 6,172,046 B1 | 1/2001 | Albrecht |
| 6,248,878 B1 | 6/2001 | Matulic-Adamic et al. |
| 6,252,060 B1 | 6/2001 | Hostetler |
| 6,271,212 B1 | 8/2001 | Chu et al. |
| 6,277,830 B1 | 8/2001 | Ganguly et al. |
| 6,312,662 B1 | 11/2001 | Erion et al. |
| 6,340,690 B1 | 1/2002 | Bachand et al. |
| 6,348,587 B1 | 2/2002 | Schinazi et al. |
| 6,369,040 B1 | 4/2002 | Acevedo et al. |
| 6,395,716 B1 | 5/2002 | Gosselin et al. |
| 6,436,437 B1 | 8/2002 | Yatvin et al. |
| 6,444,652 B1 | 9/2002 | Gosselin et al. |
| 6,448,392 B1 | 9/2002 | Hostetler et al. |
| 6,455,508 B1 | 9/2002 | Ramasamy et al. |
| 6,458,772 B1 | 10/2002 | Zhou et al. |
| 6,458,773 B1 | 10/2002 | Gosselin et al. |
| 6,472,373 B1 | 10/2002 | Albrecht |
| 6,495,677 B1 | 12/2002 | Ramasamy et al. |
| 6,566,344 B1 | 5/2003 | Gosselin et al. |
| 6,566,365 B1 | 5/2003 | Storer |
| 6,569,837 B1 | 5/2003 | Gosselin et al. |
| 6,573,248 B2 | 6/2003 | Ramasamy et al. |
| 6,596,700 B2 | 7/2003 | Sommadossi et al. |
| 6,599,887 B2 | 7/2003 | Hostetler et al. |
| 6,605,614 B2 | 8/2003 | Bachand et al. |
| 6,642,206 B2 | 11/2003 | Ramasamy et al. |
| 6,660,721 B2 | 12/2003 | Devos et al. |
| 6,748,161 B2 | 6/2004 | Ko et al. |
| 6,752,981 B1 | 6/2004 | Erion et al. |
| 6,777,395 B2 | 8/2004 | Bhat et al. |
| 6,784,161 B2 | 8/2004 | Ismaili et al. |
| 6,784,166 B2 | 8/2004 | Devos et al. |
| 6,787,526 B1 | 9/2004 | Bryant et al. |
| 6,812,219 B2 * | 11/2004 | LaColla et al. .............. 514/49 |
| 6,815,542 B2 | 11/2004 | Hong et al. |
| 6,831,069 B2 | 12/2004 | Tam et al. |
| 6,833,361 B2 | 12/2004 | Hong et al. |
| 6,846,810 B2 | 1/2005 | Martin et al. |
| 6,875,751 B2 * | 4/2005 | Imbach et al. .............. 514/49 |
| 6,908,924 B2 | 6/2005 | Watanabe et al. |
| 6,911,424 B2 | 6/2005 | Schinazi et al. |
| 6,914,054 B2 * | 7/2005 | Sommadossi et al. ......... 514/49 |
| 6,927,291 B2 | 8/2005 | Jin et al. |
| 6,946,115 B2 | 9/2005 | Erion et al. |
| 6,946,450 B2 | 9/2005 | Gosselin et al. |
| 6,949,522 B2 | 9/2005 | Otto et al. |
| 6,965,033 B2 | 11/2005 | Jiang et al. |
| 7,056,895 B2 | 6/2006 | Ramasamy et al. |
| 7,094,770 B2 | 8/2006 | Watanabe et al. |
| 7,101,861 B2 | 9/2006 | Sommadossi et al. |
| 7,105,493 B2 * | 9/2006 | Sommadossi et al. .......... 514/42 |
| 7,105,499 B2 | 9/2006 | Carroll et al. |
| 7,125,855 B2 | 10/2006 | Bhat et al. |
| 7,144,868 B2 | 12/2006 | Roberts et al. |
| 7,148,206 B2 | 12/2006 | Sommadossi et al. |
| 7,151,089 B2 | 12/2006 | Roberts et al. |
| 7,157,434 B2 | 1/2007 | Keicher et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,202,224 B2 | 4/2007 | Eldrup et al. |
| 2002/0019363 A1 | 2/2002 | Ismaili et al. |
| 2002/0035085 A1 | 3/2002 | Somadossi et al. |
| 2002/0052345 A1 | 5/2002 | Erion et al. |
| 2002/0055473 A1 | 5/2002 | Ganguly et al. |
| 2002/0055483 A1 | 5/2002 | Watanabe et al. |
| 2002/0095033 A1 | 7/2002 | Ramasamy et al. |
| 2002/0099072 A1 | 7/2002 | Bachand et al. |
| 2002/0127203 A1 | 9/2002 | Albrecht |
| 2002/0147160 A1 | 10/2002 | Bhat et al. |
| 2002/0156030 A1 | 10/2002 | Ramasamy et al. |
| 2002/0173490 A1 | 11/2002 | Jiang et al. |
| 2002/0198171 A1 | 12/2002 | Schinazi et al. |
| 2003/0008841 A1 | 1/2003 | Devos et al. |
| 2003/0028013 A1 | 2/2003 | Hong et al. |
| 2003/0039630 A1 | 2/2003 | Albrecht |
| 2003/0050229 A1 | 3/2003 | LaColla et al. |
| 2003/0053986 A1 | 3/2003 | Zahm |
| 2003/0055013 A1 | 3/2003 | Brass |
| 2003/0060400 A1 | 3/2003 | LaColla et al. |
| 2003/0083306 A1 | 5/2003 | Imbach et al. |
| 2003/0083307 A1 | 5/2003 | Devos et al. |
| 2003/0087873 A1 | 5/2003 | Stuyver et al. |
| 2003/0124512 A1 | 7/2003 | Stuyver |
| 2003/0220290 A1 | 11/2003 | Gosselin et al. |
| 2003/0225028 A1 | 12/2003 | Gosselin et al. |
| 2003/0225029 A1 | 12/2003 | Stuyver et al. |
| 2003/0225037 A1 | 12/2003 | Storer et al. |
| 2003/0236216 A1 | 12/2003 | Devos et al. |
| 2004/0002476 A1 | 1/2004 | Stuyver et al. |
| 2004/0002596 A1 | 1/2004 | Hong et al. |
| 2004/0006002 A1 | 1/2004 | Sommadossi et al. |
| 2004/0023921 A1 | 2/2004 | Hong et al. |
| 2004/0059104 A1 | 3/2004 | Cook et al. |
| 2004/0063622 A1 | 4/2004 | Sommadossi et al. |
| 2004/0063658 A1 | 4/2004 | Roberts et al. |
| 2004/0067901 A1 | 4/2004 | Bhat et al. |
| 2004/0072788 A1 | 4/2004 | Bhat et al. |
| 2004/0077587 A1 | 4/2004 | Sommadossi et al. |
| 2004/0097461 A1 | 5/2004 | Sommadossi et al. |
| 2004/0097462 A1 | 5/2004 | Sommadossi et al. |
| 2004/0101535 A1 | 5/2004 | Sommadossi et al. |
| 2004/0102414 A1 | 5/2004 | Sommadossi et al. |
| 2004/0110717 A1 | 6/2004 | Bhat et al. |
| 2004/0110718 A1 | 6/2004 | Devos et al. |
| 2004/0121980 A1 | 6/2004 | Martin et al. |
| 2004/0147464 A1 | 7/2004 | Roberts et al. |
| 2004/0229839 A1 | 11/2004 | Babu et al. |
| 2004/0248844 A1 | 12/2004 | Ismaili et al. |
| 2004/0259934 A1 | 12/2004 | Olsen et al. |
| 2004/0266722 A1 | 12/2004 | Devos et al. |
| 2004/0266723 A1 | 12/2004 | Otto et al. |
| 2004/0266996 A1 | 12/2004 | Rabi |
| 2005/0009737 A1 | 1/2005 | Clark |
| 2005/0020825 A1 | 1/2005 | Storer et al. |
| 2005/0031588 A1 | 2/2005 | Sommadossi et al. |
| 2005/0038240 A1 | 2/2005 | Connolly et al. |
| 2005/0090463 A1 | 4/2005 | Roberts et al. |
| 2005/0101550 A1 | 5/2005 | Roberts et al. |

| | | | |
|---|---|---|---|
| 2005/0107312 A1 | 5/2005 | Keicher et al. | |
| 2005/0113330 A1 | 5/2005 | Bryant et al. | |
| 2005/0119200 A1 | 6/2005 | Roberts et al. | |
| 2005/0124532 A1 | 6/2005 | Sommadossi et al. | |
| 2005/0137141 A1 | 6/2005 | Hilfinger | |
| 2005/0137161 A1 | 6/2005 | Sommadossi et al. | |
| 2005/0215511 A1 | 9/2005 | Roberts et al. | |
| 2006/0040890 A1 | 2/2006 | Martin et al. | |
| 2006/0111311 A1 | 5/2006 | Keicher et al. | |
| 2006/0166865 A1 | 7/2006 | Sommadossi et al. | |
| 2006/0194835 A1 | 8/2006 | Dugourd et al. | |
| 2006/0199783 A1 | 9/2006 | Wang et al. | |
| 2006/0241064 A1 | 10/2006 | Roberts et al. | |
| 2007/0015905 A1 | 1/2007 | LaColla et al. | |
| 2007/0060503 A1 | 3/2007 | Gosselin et al. | |
| 2007/0060504 A1 | 3/2007 | Gosselin et al. | |
| 2007/0203334 A1 | 8/2007 | Mayes et al. | |

FOREIGN PATENT DOCUMENTS

| | | |
|---|---|---|
| DE | 1919307 | 1/1971 |
| DE | 2122991 | 11/1972 |
| DE | 2508312 | 9/1976 |
| DE | 140254 | 2/1980 |
| DE | 3512781 A1 | 10/1985 |
| DE | 4224737 | 2/1994 |
| DE | 102005012681 | 9/2006 |
| EP | 0288847 | 4/1988 |
| EP | 0180276 B1 | 12/1988 |
| EP | 0352248 | 1/1990 |
| EP | 0494119 | 1/1992 |
| EP | 0526655 | 2/1993 |
| EP | 0553358 | 8/1993 |
| EP | 0587364 | 3/1994 |
| EP | 0742287 | 11/1996 |
| EP | 0747 389 | 12/1996 |
| EP | 0350287 B1 | 9/2000 |
| EP | 0650371 B1 | 11/2000 |
| FR | 1521076 | 4/1968 |
| FR | 1581628 | 9/1969 |
| FR | 2662165 | 11/1991 |
| GB | 924246 | 4/1963 |
| GB | 984877 | 3/1965 |
| GB | 1187824 | 5/1966 |
| GB | 1163 102 | 9/1969 |
| GB | 1163 103 | 9/1969 |
| GB | 1209 654 | 10/1970 |
| GB | 1542442 | 3/1979 |
| JP | 71021872 | 3/1968 |
| JP | 48048495 | 9/1971 |
| JP | 61212592 | 9/1986 |
| JP | 61263995 | 11/1986 |
| JP | 61263996 | 11/1986 |
| JP | 63215694 | 9/1988 |
| JP | 02091022 | 3/1990 |
| JP | 06135988 | 5/1994 |
| JP | 06211890 | 8/1994 |
| JP | 06228186 | 8/1994 |
| JP | 06293645 | 10/1994 |
| JP | 09059292 | 3/1997 |
| WO | WO 89/02733 A1 | 4/1989 |
| WO | WO 90/00555 A1 | 1/1990 |
| WO | WO 91/16920 A1 | 11/1991 |
| WO | WO 91/18914 A1 | 12/1991 |
| WO | WO 91/19721 A1 | 12/1991 |
| WO | WO 92/15308 | 9/1992 |
| WO | WO 92/18517 | 10/1992 |
| WO | WO 93/00910 A1 | 1/1993 |
| WO | WO 94/01117 | 1/1994 |
| WO | WO 94/26273 A1 | 11/1994 |
| WO | WO 96/15132 A1 | 5/1996 |
| WO | WO 98/16184 | 4/1998 |
| WO | WO 99/15194 A1 | 4/1999 |
| WO | WO 99/23104 | 5/1999 |
| WO | WO 99/43691 A1 | 9/1999 |
| WO | WO 99/45016 A2 | 9/1999 |
| WO | WO 99/52514 | 10/1999 |
| WO | WO 99/59621 A1 | 11/1999 |
| WO | WO 99/64016 A1 | 12/1999 |
| WO | WO 00/09531 | 2/2000 |
| WO | WO 00/24355 A1 | 5/2000 |
| WO | WO 00/25799 | 5/2000 |
| WO | WO 00/37110 A2 | 6/2000 |
| WO | WO 00/37110 A3 | 6/2000 |
| WO | WO 00/52015 A2 | 9/2000 |
| WO | WO 00/52015 A3 | 9/2000 |
| WO | WO 01/32153 | 11/2000 |
| WO | WO 01/81359 A1 | 11/2000 |
| WO | WO 01/90121 A2 | 11/2000 |
| WO | WO 01/90121 A3 | 11/2000 |
| WO | WO 01/18013 A1 | 3/2001 |
| WO | WO 01/92282 A2 | 6/2001 |
| WO | WO 01/92282 A3 | 6/2001 |
| WO | WO 01/47935 A2 | 7/2001 |
| WO | WO 01/47935 A3 | 7/2001 |
| WO | WO 01/49700 | 7/2001 |
| WO | WO 01/60315 A2 | 8/2001 |
| WO | WO 01/68663 | 9/2001 |
| WO | WO 01/32153 A2 | 10/2001 |
| WO | WO 01/79246 A2 | 10/2001 |
| WO | WO 01/79246 A3 | 10/2001 |
| WO | WO 01/91737 | 12/2001 |
| WO | WO 01/96353 A2 | 12/2001 |
| WO | WO 01/96353 A3 | 12/2001 |
| WO | WO 02/03997 | 1/2002 |
| WO | WO 02/18404 A2 | 3/2002 |
| WO | WO 02/18404 A3 | 3/2002 |
| WO | WO 02/32414 A2 | 4/2002 |
| WO | WO 02/32414 A3 | 4/2002 |
| WO | WO 02/32920 A2 | 4/2002 |
| WO | WO 02/48165 A2 | 6/2002 |
| WO | WO 02/48165 A3 | 6/2002 |
| WO | WO 02/057287 A2 | 7/2002 |
| WO | WO 02/057287 A3 | 7/2002 |
| WO | WO 02/057425 A2 | 7/2002 |
| WO | WO 02/070533 | 9/2002 |
| WO | WO 02/094289 | 11/2002 |
| WO | WO 02/100415 | 12/2002 |
| WO | WO 03/024461 A1 | 3/2003 |
| WO | WO 03/026589 | 4/2003 |
| WO | WO 03/026675 | 4/2003 |
| WO | WO 03/039523 | 5/2003 |
| WO | WO 03/051899 | 6/2003 |
| WO | WO 03/081899 | 6/2003 |
| WO | WO 03/061385 | 7/2003 |
| WO | WO 03/061576 | 7/2003 |
| WO | WO 03/062255 | 7/2003 |
| WO | WO 03/062256 | 7/2003 |
| WO | WO 03/062257 | 7/2003 |
| WO | WO 03/063771 | 8/2003 |
| WO | WO 03/068162 | 8/2003 |
| WO | WO 03/068164 | 8/2003 |
| WO | WO 03/068244 | 8/2003 |
| WO | WO 03/072757 | 9/2003 |
| WO | WO 03/093290 | 11/2003 |
| WO | WO 03/099840 | 12/2003 |
| WO | WO 03/100017 | 12/2003 |
| WO | WO 03/105770 | 12/2003 |
| WO | WO 03/106577 | 12/2003 |
| WO | WO 04/000858 | 12/2003 |
| WO | WO 2004/002422 | 1/2004 |
| WO | WO 2004/002999 | 1/2004 |
| WO | WO 2004/003138 A2 | 1/2004 |
| WO | WO 2004/007512 A2 | 1/2004 |
| WO | WO 2004/009020 A2 | 1/2004 |
| WO | WO 2004/023921 | 3/2004 |

| WO | WO 2004/028481 | 4/2004 |
| --- | --- | --- |
| WO | WO 2004/041203 | 5/2004 |
| WO | WO 2004/043977 | 5/2004 |
| WO | WO 2004/043978 | 5/2004 |
| WO | WO 2004/044132 | 5/2004 |
| WO | WO 2004/046159 | 6/2004 |
| WO | WO 2004/046331 | 6/2004 |
| WO | WO 2004/052899 | 6/2004 |
| WO | WO 2004/058792 | 7/2004 |
| WO | WO 2004/065398 | 8/2004 |
| WO | WO 2004/072090 | 8/2004 |
| WO | WO 2004/080466 | 9/2004 |
| WO | WO 2004/084796 | 10/2004 |
| WO | WO 2004/096149 | 11/2004 |
| WO | WO 2004/106356 | 12/2004 |
| WO | WO 2005/003147 | 1/2005 |
| WO | WO 2005/012327 | 2/2005 |
| WO | WO 2005/020884 | 3/2005 |
| WO | WO 2005/020885 | 3/2005 |
| WO | WO 2005/021568 | 3/2005 |
| WO | WO 2005/030258 | 4/2005 |
| WO | WO 2005/042556 | 5/2005 |
| WO | WO 2005/123087 | 12/2005 |
| WO | WO 2006/002231 | 1/2006 |
| WO | WO 2006/012078 | 2/2006 |
| WO | WO 2006/012440 | 2/2006 |
| WO | WO 2006/016930 | 2/2006 |
| WO | WO 2006/037028 | 4/2006 |
| WO | WO 2006/037227 | 4/2006 |
| WO | WO 2006/063717 | 6/2006 |
| WO | WO 2006/065335 | 6/2006 |
| WO | WO 2006/097323 | 9/2006 |
| WO | WO 2006/100087 | 9/2006 |
| WO | WO 2006/121820 | 11/2006 |
| WO | WO 2006/130532 | 12/2006 |
| WO | WO 2007/011777 | 1/2007 |
| WO | WO 2007/025304 | 1/2007 |

OTHER PUBLICATIONS

Battaglia, A.M. et al., "Combination Therapy with Interferon and Ribavirin in the Treatment of Chronic Hepatitis C Infection", *Ann. Pharmacother*, 34:487-494 (2000).

Berenguer, M. et al., "Hepatitis C virus in the transplant setting", *Antivir. Ther.*, 3 (Suppl 3):125-136 (1998).

Berman, E, et al., "Synergistic cytotoxic effect of azidothymidine and recombinant interferon alpha on normal human bone marrow progenitor cells," *Blood*, 74(4):1281-1286 (1989).

Bhat et al. (Oral Session V, Hepatitis C Virus, Flaviviridae, 2003 (Oral Session V, Hepatitis C Virus, Flaviviridae; 16$^{th}$ International Conference on Antiviral Research (Apr. 27, 2003, Savannah, Ga.); p. A75).

Browne, M.J., et al., "2',3'-didehydro-3'-deoxythymidine (d4T) in patients with AIDS or AIDS-Related Complex: A Phase I trial," *J. Infect. Dis.*, 167(1):21-29 (1993).

Colacino, J. M., "Review article: Mechanisms for the anti-hepatitis B virus activity and mitochondrial toxicity of fialurdine (FIAU)," *Antiviral Res.*, 29(2-3): 125-39 (1996).

Cui, L., et al., "Cellular and molecular events leading to mitochondrial toxicity of 1-(2-deoxy-2-fluoro-1-β-D-arabinofuranosyl)-5-iodouracil in human liver cells," *J. Clin. Invest.*, 95:555-563 (1995).

Davis, G.L., "Current therapy for chronic Hepatitis C," *Gastroenterology* 118:S104-S114 (2000).

De Francesco, R., et al., "Approaching a new era for hepatitis C virus therapy: inhibitors of the NS3-4A serine protease and the NS5B RNA-dependent RNA polymerase," *Antiviral Research*, 58: 1-16 (2003).

De Lombaert, S., et al., "N-Phosphonomethyl dipeptides and their phosphonate prodrugs, a new generation of neutral endopeptidase (NEP, EC 3.4.24.11) inhibitors," *J. Med. Chem.*, 37:498-511 (1994).

Dornsife, R.E., et al, "In vitro potency of inhibition by antiviral drugs of hematopoietic progenitor colony formation correlates with exposure at hemotoxic levels in Human Immunodeficiency Virus-positive humans," *Antimicrob. Agents Chemother.*, 40(2):514-519 (1996).

Dymock, B.W., et al., "Review: Novel approaches to the treatment of hepatitis C virus infection," *Antiviral Chemistry & Chemotherapy*, 11(2):79-95 (2000).

Eldrup et al. (Oral Session V, Hepatitis C Virus, Flaviviridae; 16$^{th}$ International Conference on Antiviral Research (Apr. 27, 2003, Savannah, Ga.).

Farkas, J., et al., "Nucleic acid components and their analogues. XCIV. Synthesis of 6-amino-9-(1-deoxy-β-D-psicofuranosyl)purine", *Collect. Czech. Chem. Commun.* 32:2663-2667 (1967).

Farkas, J., et al., "Nucleic acid components and their analogues. LXXIX. Synthesis of methyl 1-deoxy-D-psicofuranosides substituted at $C_{(1)}$ with halo atoms or a mercapto group," *Collect. Czech. Chem. Commun.*, 31:1535-1543 (1996).

Farquhar, D., et al., "Synthesis and biological evaluation of neutral derivatives of 3-fluoro-2'-deoxyuridine 5'-phosphate," *J. Med. Chem.* 26: 1153 (1983).

Farquhar, D., et al., "Synthesis and biological evaluation of 9-[5'-(2-oxo-1,3,2-oxazaphosphorinan-2-yl)-β-D-arabinosyl]adenine and 9-[5'-(2-oxo-1,3,2-dioxazaphosphorinan-2-yl)-β-D-arabinosyl]adenine: Potential neutral precursors of 9-[β-D-arabinofuranosyl]adenine 5'-monophosphate," *J. Med. Chem.* 28:1358-1381 (1985).

Ferrari R., et al., "Characterization of soluble hepatitis C virus RNA-dependent RNA polymerase expressed in *Escherichia coli*," *Journal of Virology*, 73(2), 1649-1654 (1999).

Fischl, M.A., et al., "Zalcitabine compared with zidovudine in patients with advanced HIV-1 infection who received previous zidovudine therapy," *Ann. Intern. Med.*, 18(10):762-769 (1993).

Freed, J.J., et al., "Evidence for acyloxymethyl esters of pyrimidine 5'-deoxyribonucleotides as extracellular sources of ative 5'-deoxyribonucleotides in cultured cells," *Biochemical Pharmacology*. 38:3193-3198 (1989).

Gunic, E., et al., "Synthesis and cytotoxicity of 4'-C- and 5'-C-substituted Toyocamycins," *Bioorg. Med. Chem.*, 9:163-170 (2001).

Harry-O'Kuru, R.E., J.M. Smith, and M.S. Wolfe, "A short, flexible route toward 2'-C-branched ribonucleosides", *J.Org. Chem.* 62, 1754-1759 (1997). (Scheme 11).

Hostetler, K.Y., et al., "Synthesis and antiretroviral activity of phospholipids analogs of azidothymidine and other antiviral nucleosides," *J. Biol. Chem.*, 265:6112-6117 (1990).

Hostetler, K.Y., et al., "Greatly enhanced inhibition of Human Immunodeficiency Virus Type I replication in CEM and HT4-6C cells by 3'-deoxythymidine diphosphate dimyristoylglycerol, a lipid prodrug of 3'-deoxythymidine," *Antimicrob. Agents Chemother.*, 36:2025.2029 (Sep. 1992).

Hunston, R.N., et al., "Synthesis and biological properties of some cyclic phosphotriesters drived from 2'-deoxy-5-fluorouridine," *J. Med. Chem.* 27:440-444 (1984).

Jones, G. H.; Moffatt, J. G., *Methods in Carbohydrate Chemistry*; Whisler, R. L. and Moffatt, J. L. Eds; Academic Press: New York, 1972; 315-322.

Jones, G. H., et al., "4'-substituted nucleosides. 5. Hydroxymethylation of nucleoside 5'-aldehydes," *J. Org. Chem.*, 44:1309-1317 (1979).

Khamnei, S., "Neighboring group catalysis in the design of nucleotide prodrugs," *J. Med. Chem.*, 39:4109-4115 (1996).

Kucera, L.S., et al., "Novel membrane-interactive ether lipid analogs that inhibit infectious HIV-1 production and induce defective virus formation," *AIDS Res. Hum. Retro Viruses*, 6:491-501 (1990).

Kurtzberg J., et al., "Differential toxicity of carbovir and AZT to human bone marrow hematopoietic progenitor cells in vitro," *Exp. Hematol.*, 18(10):1094-1096 (1990).

Leonard, N. J., et al., "5-Amino-5-deoxyribose derivatives. Synthesis and use in the preparation of "reversed" nucleosides" *J. Heterocycl. Chem.*, 3:485-489 (Dec. 1966).

Lerza, R, et al., "In vitro synergistic inhibition of human bone marrow hemopoietic progenitor growth by a 3'-azido-3'-deoxy-thymidine, 2',3'-dideoxycytidine combination," *Exp. Hematol.*, 25(3):252-255 (1997).

Lewis W, et al., "Zidovudine induces molecular, biochemical, and ultrastructural changes in rat skeletal muscle mitochondria," *J. Clin. Invest.*, 89(4):1354-1360 (1992).

Lewis, L. D., et al., "Ultrastructural changes associated with reduced mitochondrial DNA and impaired mitochondrial function in the presence of 2'3'-dideoxycytidine," *Antimicrob. Agents Chemother.*, 36(9):2061-2065 (1992).

Lewis, W., et al., "Fialuridine an dits metabolites inhibit DNA polymerase γ at sites of ultiple adjacent analog incorporation, decrease mtDNA abundance, and cause mitochondrial structural defects in cultured hepatoblasts," *Proceedings of the National Academy of Sciences*, USA, 93(8): 3592-7 (1996).

Lohmann V., et al., "Biochemical and kinetic analyses of NS5B RNA-dependent RNA polymerase of the Hepatitis C virus," *Virology*, 249, 108-118 (1998).

Luh, T.-Y., et al., "A convenient method for the selective esterification of amino-alcohols," *Synthetic Communications*, 8(5):327-333 (1978).

McCormick, J., et al., "Structure and total synthesis of HF-7, a neuroactive glyconucleoside disulfate from he funnel-web spide *Hololena curta*," *J. Am. Chem. Soc.*, 121(24), 5661-5664 (1999).

McKenzie, R., et al., "Hepatic failure and lactic acidosis due to fialuridine (FIAU), an investigational nucleoside analogue for chronic hepatitis B", *N. Engl. J. Med.*, 333(17):1099-1105 (1995).

Meier, C., et al., "Cyclic saligenyl phosphotriesters of 2',3'-dideoxy-2',3'-didehydrothymidine (d4T)—A new pro-nucleic approach." *Bioorganic & Med. Chem. Letters* 7(2):99-104 (1997).

Medina, D. J., et al., "Comparison of mitochondrial morphology, mitochondrial DNA content, and cell viability in cultured cells treated with three anti-Human Immunodeficiency Virus dideoxynucleosides," *Antimicrob. Agents Chemother.*, 38(8):1824-8 (1994).

Meyer, R.B., Jr., et al., "2'-O-Acyl-6-thioinosine cyclic 3',5'-phosphates as prodrugs of thioinosinic acid," *J. Med. Chem.* 22: 811-815 (1979).

Neidlein, R., et al., "Mild preparationof 1-benzyuloxyiminoalkylphosphonic dichlorides: Application to the synthesis of cyclic phosphonic diesters and cyclic monoester amides," *Heterocycles* 35:1185-1203 (1993).

Nutt, R.F., et al., "Branched-chain sugar nucleosides. III. 3'-C-methyladenine", *J.Org. Chem.*, 33:1789-1795 (1968).

Olsen, et al. (Oral Session V, Hepatitis C Virus, Flaviviridae; 16th International Conference on Antiviral Research (Apr. 27, 2003, Savannah, Ga.) p. A76).

Pan-Zhou, X-R, et al., "Differential effects of antiretroviral nucleoside analogs on mitochondrial function in HepG2 cells," *Antimicrob. Agents Chemother.* 44:496-503 (2000).

Piantadosi, C., et al., "Synthesis and evaluation of novel ether lipid nucleoside conjugates for anti-HIV-1 activity," *J. Med. Chem.* 34:1408-1414 (1991).

Richman, D.D., et al., "The toxicity of azidothymidine (AZT) in the treatment of patients with AIDS and AIDS-Related Complex," *N. Engl. J. Med.*, 317(4):192-197 (1987).

Sommadossi J-P, et al., "Comparison of cytotoxicity of the (−)- and (+)- enantiomer of 2',3'-dideoxy-3'-thiacytidine in normal human bone marrow progenitor cells," *Biochemical Pharmacology* 44(10):1921-1925 (1992).

Sommadossi J.-P., et al., "Toxicity of 3'-azido-3'-deoxythymidine and 9-(1,3-dihydroxy-2-propoxymethyl)guanine for normal human hematopoietic progenitor cells in vitro," *Antimicrobial Agents and Chemotherapy*, 31:452-454 (1987).

Starrett, J.E.Jr., et al., "Synthesis, oral bioavailability determination, and in vitro evaluation of prodrugs of the antiviral agents 9-(2-(phosphonomethoxy)ethyl]adenine (PMEA)," *J. Med. Chem.* 37: 1857-1864 (1994).

Weinberg, R.S., et al., "Effect of antiviral drugs and hematopoietic growth factors on in vitro erythropoiesis," *Mt. Sinai J. Med.* 1998;65(1):5-13.

Yarchoan, R., et al. "Long-term toxicity / activity profile of 2',3'-dideoxyinosine in AIDS or AIDS-related complex," *The Lancet*, 336(8714):526-529 (1990).

Yoshida Y, et al., "Reversal of azidothymidine-induced bone marrow suppression by 2',3'-dideoxythymidine as studied by hemopoietic clonal culture," *AIDS Res. Hum. Retroviruses*, 6(7):929-932 (1990).

Zon, G., "Cyclophosphamide Analogues," Chapter 4 in *Progress in Medicinal Chemistry*, Vol. 19, G.P. Ellis and G.B. West, Eds., pp. 205-246 (1982).

Awano, H., et al., "Nucleosides and nucleotides. Part 144. Synthesis and antiviral activity of 5-substituted (2'S)-2'-deoxy-2'-C-methylcytidines and -uridines," *Archiv der Pharmazie*, VCH Verlagsgesellschaft mbh, Weinheim, DE. 329 :66-72 (Feb. 1, 1996).

Beigelman, L.N., et al, "A general method for synthesis of 3'-C-alkylnucleosides," *Nucleic Acids Symp. Ser.*, 9:115-118 (1981).

Bianco, et al.,"*Synthesis of a New Carbocyclic Nucleoside Analog*", Tetrahedron Letters, vol. 38. No. 36., Set 8 1997.

Cappellacci, L., et al., "Ribose-modified nucleosides as ligands for adenosine receptors: Synthesis, conformational analysis, and biological evaluation of 1'-C-methyl adenosine analogues," *J. Med. Chem.*, 45:1196-1202 (2002).

Chiacchio, ., et al.,"Steroselective Synthesis of 2'-Amino-2',3'-Dideoxynucleosides by Nitrone 1,3-Dipolar Cycloaddition: A New Efficient Entry Toward d4T and iIts 2-Methyl Analogue ", *J. Org. Chem.* vol. 64: 28-36 (1999).

Czernecki S. et al., "Synthesis of 2'-deoxy-2'-spirocyclopropyl Cytidine as Potential Inhibitor of Ribonuclotide Diphosphate Reductase", *Can. J. Chem.*, 71: 413-416 (1993).

Federov, I.I., et al., "3'-C-branched 2'-deoxy-5-methyluridines: Synthesis, enzyme inhibition, and antiviral properties," *J. Med. Chem.*, 35:4567-4575 (1992).

Franchetti, P., et al., "2'-C-Methyl analogues of selective adenosine receptor agonists: synthesis and binding studies," *J. Med. Chem.*, 41(10):1708-1715 (1998).

Hassan, A.E.A. , et al., "Nucleosides and Nucleotides. 156. Chelation-Controlled and Nonchelation-Controlled Diastereofacial Selective Thiophenol Addition Reactions at the 2'-Position of 2'-[(Alkoxycarbonyl)methylene]-2'-deoxyuridines: Conversion of (Z0-2'-[(Alkoxycarbonyl)methylene]-2'-Deoxyuridines into Their (E)-Isomers", *J. Org. Chem.*, 62: 11-17 (1997).

Hassan, A.E.A. , et al., "Nucleosides and Nucleotides. 151. Conversion of (Z)-2'-(Cyanomethylene)-2'-Deoxyuridines into Their (E)-Isomers via Addition of Thiophenol to the Cyanomethylene Moiety Followed by Oxidative Syn-elimination Reactions", *J. Org. Chem.*, 61: 6261-6267 (1996).

Hossain N. , et al., "Synthesis of 2'- and 3'-Spiro-Isoxazolidine Derivatives of Thymidine& Their Conversions To 2', 3'-Dideoxy-2', 3'-Didehydro-3'-C-Substituted Nucleosides by Radical Promoted Fragmentation", *Tetrahedron*, 49: 10133-10156 (1993).

Hattori, H., et al., "Nucleosides and nucleotides. 158.," *J. Med. Chem.*, 39:5005-5011 (1996).

Hrebabecky, H., et al., "Nucleic acid components and their analogues. CXLIX. Synthesis of pyrimidine nucleosides derived from 1-deoxy-D-psicose," *Collect. Czech. Chem. Commun.*, 37:2059-2065 (1972).

Hrebabecky, H., et al. "Synthesis of 7- and 9β-D-psicofuranosylguanine and their 1'-deoxy derivatives," *Collect. Czech. Chem. Commun.*, 39:2115-2123 (1974).

Johnson, C.R., et al., "3'-C-Trifluoromethyl ribonucleosides," *Nucleosides & Nucleotides*, 14(1&2):185-194 (1995).

Li, Nan.-Sheng., et al., "2'-C-branched ribonucleosides. 2. Synthesis of 2'-C-β-trifluoromethyl pyrimidine ribonucleosides," *Organic Letters*,3(7):1025-1028 (2001).

Mahmoudian M. et al., "A Versatile Procedure for the Generation of Nucleoside 5-'Carboxylic Acids Using Nucleoside Oxidase", *Tetrahadron*, 54: 8171-8182 (1998).

Matsuda, A., et al., "Radical deoxygenation of *tert*-alcohols in 2'-branched-chain sugar pyrimidine nucleosides: Synthesis and antileukemic activity of 2'-deoxy-2'(S)-methylcytidine," *Chem. Pharm. Bull.*, 35(9):3967-3970 (1987).

Matsuda, A., et al., "Nucleosides and Nucleotides. 94. Radical deoxygenation of *tert*-alcohols in 1-(2-C-alkylpentofuranosyl)pyrimidines: Synthesis of (2'S)-2'-deoxy-2'-C-methylcytidine, an antileukemic nucleoside," *J. Med. Chem.*,34:234-239 (1991).

Mikhailov, S.N., et al., "Synthesis and properties of 3'C-methylnucleosides and their phosphoric esters," Carbohydrate Research, 124:75-96 (1983).
Mural, Y., et al., "A synthesis and an X-ray analysis of 2'-C-, 3'-C- and 5'-C-methylsangivamycins," Heterocycles, 1(33):391-404 (1992).
Ong, S.P., et al, "Synthesis of 3'-C-methyladenosine and 3'-C-methyluridine diphosphates and their interaction with the ribonucleoside diphosphate reductase from Corynebacterium nephridii," Biochemistry, 31(45):11210-11215 (1992).
Rosenthal, A., et al., Branched-chain sugar nucleosides. Synthesis of 3'-C-ethyl (and 3'-C-butyl)uridine Carbohydrate Research, 79:235-242 (1980).
Schmit, C., "Synthesis of 2'-deoxy-2'-α-monofluoromethyl and trifluoromethylnucleosides," Synlett, Thieme Verlag, Stuttgart, DE, (4):241-242 (1994).
Sharma, P.K., et al., "Synthesis of 3'-trifluoromethyl nucleosides as potential antiviral agents," Nucleosides, Nucleotides and Nucleic Acids, 19(4):757-774 (2000).
Tronchet, J.M.J.; et al., "72. Synthèse et désamination enzymatique des C-hydroxyméthyl-3'-et C-méthyl-3'-beta-D-xylofurannosyl-9-adénin es," Helv. Chim. Acta, 62:689-695 (1979).
Velazquez, S. , et al., "Synthesis of [1[3',5'-bis-O-(tert-butyldimethylsilyl-β-D-arabino- and β-D-ribofuranosyl] cytosine]-2'-spiro-5"-(4"-amino-1", 2"-oxathiole-2", 2"-dioxide). Analogues of the Highly Specific Anti-HIV-1 agent TSAO-T", Tetrahedron, 50: 11013-11022 (1994).
Wolf, J., et al., "New 2'-C-branched-chain sugar nucleoside analogs with potential antiviral or antitumor activity," Synthesis, Georg Thieme Verlag. Stuttgart, DE, (8):773-778 (Aug. 1992).
Vassilev, R., et al., "Bovine Viral Diarrhea Virus Induced Apoptosis Correlates With Increased Intracellular Viral RNA Accumulation", Virus Research, 69: 95-107 (2000).
U.S. Appl. No. 10/845,976, filed May 14, 2004, Storer, et al.
U.S. Appl. No. 11/005,443, filed Dec. 6, 2004, Gosselin, et al.
U.S. Appl. No. 11/516,928, filed Sep. 6, 2006, Sommadossi, et al.
U.S. Appl. No. 11/644,304, filed Dec. 22, 2006, Mayes, et al.
Afdhal, et al., Enhanced antiviral efficacy for valopicitabine pluc PEG-interferon in hepatitis C patients with HCV genotype-1 infection. Journal of Hepatology 2005, Vol. 42, Supplement 2, p. 39-40.
Alt, et al., "Specific inhibition of hepatitis C viral gene expression by antisense phosphorothioate oligodeoxynucleotides," Hepatology, 22:707-717 (1995).
Alt, et al., "Core Specific Antisense Phosphorothioate Oligodeoxynucleotides as Ptent and Specific Inhibitors of Hepatitis C Viral Translation." Arch. Virol. (1997) 142: 589-599.
Altmann, et al., "The Synthesis of 1'-Methyl Carbocyclic Thymidine and Its Effect on Nucleic Acid Duplex Stability," Synlett, Thieme Verlag. Stuttgart, De, 10:853-855 (1994).
Altmann, et al., The Effects of 2'- and 3'-Alkyl Substituents on Oligonucleotide Hybridization and Stability, Biorganic & Medicinal Chemistry Letter. 1994. 4. No. 16. 1969-74.
Beigelman et al., "New synthesis of 2'-C-methylnucleosides starting from D-glucose and D-ribose" Carbohydrate Res., 1987.166,.219-232.
Beigelman et al., "Epimerization During the Acetolysis of 3-O-Acetyl-5-O-Benzoyl-1,2-o-Isopropylidene-3-C-Methyl-a, D-Ribofuranose. Synthesis of 3'-C-Methylnucleosides with the B-D-ribo-and a-D-arabino Configurations," Carbohydrate Research, 181:77-88 (1988).
Beigelman et al., Functionally complete analogs of nucleosides. The use of D-glucose for the synthesis of 2-C-methyl-D-ribose derivatives and related nucleosides. Biorrganicheskaya Khimiya. 1986, Vol. 12(10), pp. 1359-1365.
Berenguer, M., et al., "Hepatitis B and C viruses: Molecular identification and targeted antiviral therapies," Proceedings of the Association of American Physicians, 110(2), 98-112 (1998).
Bhopale, Girish Mahadeorao, et al., "Emerging drugs for chronic hepatitis C," Hepatology Research (2005), 32(3), 146-153.
Billich, et al., "Nucleoside Phosphotransferase from Malt Sprouts." Biol. Chem. Hoppe-Seyler, Vol. 367, pp. 267-278, Apr. 1986.
Bio, et al., "Practical Synthesis of a Potent Hepatitis C Virus RNA Replication Inhibitor." Journal of Organic Chemistry (2004), 69(19), 6257-6266.

Bloch A., et al., "The Role of the 5'-Hydroxyl Group of Adenosine in Determining Substrate Specificity for Adenosine Deaminase," J. Med. Chem., 10(5):908-12 (Sep. 1967).
Bryant M.L., et al., "Antiviral L-Nucleosides Specific for Hepatitis B Virus Infection," Antimicrobial Agents and Chemotherapy, 45(1):229-235 (Jan. 2001).
Cappelacci ,et al., "Synthesis, Biological Evaluation, and Molecular Modeling of Ribose-Modified Adenosine Analogues as Adenosine Receptor Agonists." Journal of Medicinal Chemistry (2005), 48(5), 1550-1562.
Carroll, S.S., "Nucleoside analog inhibitors of hepatitis C virus replication," Infectious Disorders: Drug Targets (2006), 6(1), 17-29.
Carroll S.S., et al., "Inhibition of hepatitis C virus RNA replication by 2'-modified nucleoside analogs," J. Biol. Chem., 278(14): 11979-11984 (2003).
Cavelier, F., et al., "Studies of Selective Boc Removal in the Presence of Silyl Ethers," Tetrahedron Letters, 37: 5131-5134 (1996).
Chand, Pooran: et al.. "Synthesis of (2S,3S,4R,5R)-2-(4- amino-5H-pyrrolo[3,2-d]pyrimidin-7-yl)-5-(hydroxymethyl)-3-methylpyr-rolidine-3,4-diol, an analog of potent HCV inhibitor." Collection Symposium Series (2005), 7(Chemistry of Nucleic Acid Components), 329-332.
Chen et al., Heterocycles, vol. 28, No. 2, 1989, pp. 593-601.
Chiaramonte, et al., "Inhibition of CMP-Sialic Acid Transport into Golgi Vesicles by Nucleoside Monophates." Biochemistry 2001, 40, 14260-14267.
Clark, et al., Synthesis and antiviral activity . . . , Bioorganic & Medicinal Chemistry Letters, 16, 2006, 1712-1715.
Clark, et al., "Design, Synthesis, and Antiviral Activity of 2'-Deoxy-2'-fluoro-2'-C-methylcytidine, a Potent Inhibitor of Hepatitis C Virus Replication." Journal of Medicinal Chemistry (2005), 48(17), 5504-5508.
Coelmont, Lotte, "Ribavirin antagonizes the in vitro anti-hepatitis C virus activity of 2'-C-methycytidine, the active component of valopicitabine," Antimicrobial Agents and Chemotherapy (2006), 50(10), 3444-3446.
Cook, G.S., "Improving the treatment of hepatitis C infection in the UK," Expert Opinion on Pharmacotherapy, (2007) vol. 8, No. 2, pp. 183-191.
Cornberg, M., et al., "Present and future therapy for hepatitis C virus," Expert review of Anti-Infective Therapy, (2006) vol. 4, No. 5, pp. 781-793.
Cretton-Scott, E., et al., "Pharmacokinetics of B-L-2'-Deoxyctidine Prodrugs in Monkeys," Antiviral res., 50:A44 (2001).
Czernecki, S., et al., "Synthesis of various 3'-branched 2', 3'-unsaturated pyrimidine nucleosides as potential anti-HIV agents," J. Org. Chem., 57: 7325-7328 (1992).
Dalpiaz, et al., "Temperature dependence of the affinity enhancement of selective adenosine A1 receptor agonism: a thermodynamic analysis." European Journal of Pharmacology (2002), 448(2-3), 123-131.
Daniels et al., "Tautomerism of Uracil and Thymine in Aqueous Solution: Spectroscopic Evidence", Proc. Nat. Acad. Sci. USA, vol. 69, No. 9, pp. 2488-2491, 1972.
Davis, G.L., "New Therapies: Oral Inhibitors and Immune Modulators," Clinics in Liver Disease, (2006) vol. 10, No. 4, pp. 867-880.
Davisson, V.J., et al., "Synthesis of Nucleotide 5'-Diphosphates from 5'-O-Tosyl Nucleosides," J. Org. Chem., 52(9):1794-1801 (1987).
Ding, et al., "Synthesis of 2'-b-C-methyl toyocamycin and sangivamycin analogs as potential HCV inhibitors." Bioorganic & Medicinal Chemistry Letters (2005), 15(3), 725-727.
Ding, et al., "Synthesis of 9-(2-b-C-methyl-b-D-ribofuranosyl)-6-substituted purine derivatives as inhibitors of HCV RNA replication." Bioorganic & Medicinal Chemistry Letters (2005), 15(3), 709-713.
Dutartre, H., et al., "General catalytic deficiency of hepatitis C virus RNA polymerase with an S282T mutation and mutually exclusive resistance towards 2'-modified nucleotide analogues," Antimicrobial Agents and Chemotherapy, (2006) vol. 50, No. 12, pp. 4161-4169.
Eldrup et al., "Structure-Activity Relationship of Heterobase-Modified 2'-C-Methyl Ribonucleosides as Inhibitors of Hepatitis C Virus RNA Replication." Department of Medicinal Chemistry, Isis Pharmaceuticals, Carlsbad, CA, USA. Journal of Medicinal Chemistry (2004), 47(21), 5284-5297.

Eldrup, et al., "Structure-Activity Relationship of Purine Ribonucleosides for Inhibition of Hepatitis C Virus RNA-Dependent RNA Polymerase.", Department of Medicinal Chemistry, Isis Pharmaceuticals, Carlsbad, CA, USA. Journal of Medicinal Chemistry (2004), 47(9), 2283-2295.

Faivre-Buet, et al., "Synthesis of 1'-Deoxypsicofuanosyl-Dexoynucleosides as Potential Anti-HIV Agents." Nucleosides & Nucleotides, vol. 11, No. 7, 1992, pp. 1411-1424.

Farquhar et al., "Biologically reversible phosphate-protective groups," J. Phurm. Sci., 1983, 72(3): 324.

Feast, A.A.J., et al., "Studies on the D-Glucosaccharinic Acids," Acta Chemica Scandinavica 19(5):1127-1134 (1965).

Fox, J. J., et al., "Thiolation of nucleosides. II. Synthesis of 5-methyl-2'-deoxycytidine and related pyrimidine nucleosides," J. Am. Chem. Soc., 81: 178-187 (Jan. 5, 1959).

Francesco, et al. Antiviral Research 58 (2003) 1-16.

Franchetti, et al., "Antitumor Activity of C-Methyl-b-D-ribofuranosyladenine Nucleoside Ribonucleotide Reductase Inhibitors." Journal of Medicinal Chemistry (2005), 48(15), 4983-4989.

Fujimori, et al., "A Convenient and Stereoselective Synthesis of 2'-Deoxy-[beta]-L-nucleosides," Nucleosides & Nucleotides, 11(2-4), 341-349 (1992); only CAPLUS abstract supplied.

Furukawa, Y., et al. "A novel method for synthesis of purine nucleosides using Friedel-Crafts catalysts," Chem. Pharm. Bull., 16(6):1076-1080 (Jun. 1968).

Galderisi, U., et al., "Antisense oligonucleoties as therapeutic agents," Journal of Cellular Physiology, 181(2):251-257 (Nov. 1999).

Gallo, et al., "2'-C-Methyluridine Phosphoramidite: A New Building Block for the Preparation of RNA Analogues Carrying the 2'-hydroxyl Group." Tetrahedron, 57 (2001), 5707-5713.

Gerotto, et al., Effect of retreatment with interferon alone or interferon plus ribavirin on hepatitis C virus quasispecies diversification in nonresponder pateinets with chronic hepatitis C. Journal of Virology, Sep. 1999, vol. 73, No. 9, p. 7241-7247.

Giradet, et al., "Synthesis and Cytotoxicity of 4-Amino-5-oxopyrido[2,3-d]pyrimidine Nucleosides." Journal of Medicinal Chemistry (2000), 43(20), 3704-3713.

Gretch, D.R., "Use and interpretation of HCV diagonostic tests in the clinical setting." Clinics in Live Disease, Nov. 1997, vol. 1, No. 3, pp. 547-557.

Grouiller, et al., "Novel-p-toluensesulfaonylation and Thionocarbonylation of Unprotected Thymine Nucleosides," Synlett, 1993: 221-222 (1993).

Grouiller et al., "Structural studies on a psicofuranosyl nucleoside, a potential antiviral agent." J. Pharm. Belg., 47(4), 381-3 (1992).

Grunnagel, et al., "Preparation of D-Tagatose." Justus Liebigs Annalen der Chemie (1969), 721: 234-5.

Haraguchi, et al., "Preparation and Reactions of 2'-and 3'- Vinyl Bromides of Uracil Nucleosides: Versatile Synthons for Anti-HIV Agents," Tetrahedron Letters, 32(28): 3391-94 (1991).

Haraguchi, et al., "Stereoselective Synthesis of 1'-C-Branched Uracil Nucleosides from Uridine," Nucleotides & Nucleotides, 14(3-5): 417-420 (1995).

Harry-O'Kuru, et al., "2'-C-alkylribonucleosides: Design, Synthesis and Conformation," Nucleosides & Nucleotides, vol. 16: 1457-60 (1997).

Hattori, H., et al., "Nucleosides and Nucleotides 175. Structural requirements of the sugar moiety for the antitumor activities of new nucleoside antimetabolites, 1-(3-C-ethynyl-b-D-ribo-pentofuranosyl)cytosine and—uracil," J. Med. Chem., 41: 2892-2902 (1998).

Hayakawa, et al., "Reaction of organometallic reagents with 2'- and 3'-ketouridine derivatives: synthesis of uracil nucleosides branched at the 2'- and 3'-positions." Chemical & Pharmaceutical Bulletin (1987), 35(6), 2605-8.

Hoard, D.E., et al., "Conversion of Mono- and Oligodeoxyribonucleotides to 5'-Triphosphates," J. Am Chem. Soc., 87(8):1785-1788 (Apr. 20, 1965).

Hodge, et al., "Amadori Rearrangement Products." Methods in Carbohydrate Chemistry (1963), 2: 99-107.

Holy, A., "Nucleic Acid Components and Their Analogs. CLIII. Preparation of 2'-deoxy-L-Ribonucleosides fo the Pyrimidine Series," Collect. Czech. Chem. Commun., 37(12): 4072-4087 (1972).

Hu, et al., Viral, host and interferon-related factors modulating the effect of interferon therapy for hepaptitis C virus infection. Journal of Viral Hepatitis, 2001, vol. 8, p. 1-18.

Iglesias, et al., "Complete and Regioselective Deacetylation of Peracetylated Uridines Using a Lipase." Biotechnology Letters 22: 361-365, 2000.

Iimori. et al., "2'-C-, 3'-C-, and 5'-C-Methylsangivamyeins: conformational lock with the methyl group." Tetrahedron Letters (1991), 32(49), 7273-6.

Iimori, et al., "A study on conformationally restricted sangivamycins and their inhibitory abilities of protein kinases." Nucleic Acids Symposium Series (1992), 27(Nineteenth Symposium on Nucleic Acids Chemistry, 1992), 169-70.

Iino, T., et al., "Nucleosides and nucleotides 139. Stereoselective synthesis of (2'S)-2'-C-alkyl-2'-deoxyuridines," Nucleosides & Nucleotides, 15(1-3): 169-181 (1996).

Ikegashira, K., et al., "Discovery of conformationally constrained tetracylic compounds as potent hepatitis C virus NS5B RNA polymerase inhibitors," Journal of Medicinal Chemistry, (Nov. 30, 2006) vol. 449, No. 24, pp. 6950-6953.

Imai, K., et al., "Studies on Phosphorylation. IV. Selective Phosphorylation of the Primary Hydroxyl Group in Nucleosides." J. Org. Chem., 34(6): 1547-1550 (Jun. 1969).

Itoh, et al., "Divergent and Sterocontrolled Approach to the Synthesis of Uracil Nucleosides Branched at the Anomeric Position," J Org Chem, 60(3): 656-662 (1995).

Kakefuda, et al., "Nucleosides and nucleotides. 120. Stereoselective radical deoxygenation of tert-alcohols in the sugar moiety of nucleosides: synthesis of 2',3'-dideoxy-2'-C-methyl- and -2'-C-ethynyl-b-D-threo-pentofuranosyl pyrimidines and adenine as potential antiviral and antitumor agents." Tetrahedron (1993), 49(38), 8513-28.

Kamaike, K., et al., "An efficient method for the synthesis of [4-15N]cytidine, 2'-deoxy[4-15N]cytidine, ]6-15N]adenosine, and 2'-deoxy[6-15N]adenosine derivatives," Nucleosodies and Nucleotides, 15(1-3_: 749-769 (1996).

Kaneko, M., et al., "A convenient synthesis of cytosine nucleosides," Chem. Pharm. Bull., 20:1050-1053 (1972).

Kawana, et al, "The Deoxygenatio of Tosylated Adenosine Derivatives with Grignard Reagents," Nucleic Acids Symp Ser, 17:37-40 (1986).

Kempe, T., et al., "Selective 2'-Benzoylation at the Cis 2', 3'-diols of Protected Ribonucleosides. New Solid Phase Synthesis of RNA and DNA-RNA Mixtures," Nucleic Acids Res., 10(21):6695-6714 (Nov. 11, 1982).

Kerr, S.G., et al., "N-(Dialkylamino)Methylene Derivatives of 2'-Deoxycytidine and Arabinocytidine: Physicochemical Studies for Potential Prodrug Applications," J. Pharm. Sci., 83(4): 582-586 (Apr. 1994).

Kim, et al., "A Novel Nucleoside Prodrug-Activating Enzyme: Substrate Specificity of Biphenyl Hydrolase-like Protein," Molecular Pharmaceutics (2004), 1(2), 117-127.

Klumpp, et al., "The Novel Nucleoside Analog R1479 (4'-Azidocytidine) is a Potent Inhibitor of NS5B-dpendent RNA Synthesis and Hepatits C Virus Replication in Cell Culture." The Journal of Biological Chemistry, vol. 281, No. 7, pp. 3793-3799, Feb. 17, 2006.

Kohn, et al., "A new method for the synthesis of furanose derivatives of aldohexoses," J Am. Chem. Soc., 1965, 87(23): 5475-80.

Kotra, L., et al., "Structure-Activity Relationships of 2'-Deoxy-2',2'-difluoro-L-erythro-pentofuranosyl Nucleosdes." J. Med. Chem. 1997, 40, 3635-3644.

Kuhn, R., et al., "Uber eine molekulare Umlagerung von N-Glucosiden." Jahrg. 69, 1936, p. 1745-1754.

Lai, V.C.H., et al., "Mutational analysis of bovine viral diarrhea virus RNA-dependant RNA polymerase," J. Virol., 73(12):10129-101136 (Dec. 1999).

Landowski, "Nucleoside ester prodrug substrate specificity of liver carboxylesterase," Journal of Pharmacology and Experimental Therapeutics (2006), 316(2), 572-580.

Lavaire, S., et al., "3'-deoxy-3'-C-trifluoromethyl nucleosides: Synthesis and antiviral evaluation," Nucleosides & Nucleotides, 17(12): 2267-2280 (1998).

Le Pogam, et al., "In Vitro Selected Con1 Subgenomic Replicons Resistant to 2'-C-Methyl-Cytidine or to R1479 Show Lack of Cross Resistance." Virology 351 (2006), 349-359.

Le Pogam, et al., "Selection and Characterization of Replicon Variants Dually Resistant to Thumb- and Palm- Binding Nonnucleoside Polymeras Inhibitors of the Hepatitis C Virus." Journal of Virology, vol. 80, No. 12, Jun. 2006, p. 6146-6154.

Leyssen, P., et al., "Perspectives for the treatment of infections with Flaviviridae," Clinical Microbiology Reviews (Washington D.C.) 13(1): 67-82 (Jan. 2000).

Lin, T.S., et al., "Synthesis of Several Pyrimidine L-Nucleoside Analogues as Potential Antiviral Agents," Tethrahedron Letters, 51(4): 1055-1068 (1995).

Lopez Aparicio, F.J., et al., "Synthesis of Saccarinic Acid Derivatives," Carbohydrate Res., 129:99 (1984).

Lopez-Herrera, F.J., et al., "A New Synthesis of 2-C Methyl-D-Ribono-1, 4-Lactone and the C-(/C-13 Fragment of Methynolide," J. Carbohydrate Chemistry, 13(5): 767-775 (1994).

Maga, Giovanni, et al., Lack of stereospecificity of suid pseudorabies virus thymidine kinase, Biochem. J., 294(2): 381-385 (1993).

Mansour, T.S., et al., "Editorial," Anti-Ineffective Agents in Medicinal Chemistry, (2007) vol. 6, No. 1, pp. 1.

Markland W., et al., "Broad-spectrum antiviral activity of the IMP dehydrogenase inhibitor VX-497: a comparison with ribavirin and demonstration of antiviral additivity with alpha interferon." Antimicrobial Agents and Chemotherapy, Apr. 2000, vol. 44, No. 4, pp. 859-866.

Martin, J., et al., Synthesis and Antiviral Activity of Monofluoro and Difluoro Analogues of Pyrimidine Deoxyribonucleosides Against Human Immnodeficiency Virus (HIV-1). J. Med. Chem. 1990, 33, 2137-2145.

Martin, X., et al., "Intramolecular hydrogen bonding in primary hydroxyl of thymine 1-(1-deoxy-β-D-piscofuranosyl)nucleoside," Tetrahedron, 50(22): 6689-6694 (1994).

Matsuda, et al., "Alkyl Addition Reaction of Pyrimidine 2'-Ketaonucleosides: Synthesis of 2'-Branched-Chain Sugar Pyrimidne Nucleosides (Nucleosides and Nucleotides. LXXXI)" Chem Pharm Bull, vol. 36(3):945-53 (1988).

Matsuda, et al., "Nucleosides and Nucleotides 104. Radical and Palladium-Catalyzed Deoxygenation of the Allylic Alcohol Systems in the Sugar Moiety of Pyrimidine Nucleosides." Nucleosides & Nucleotides, Dekker, New York, NY, U.S., vol. 11, No. 2/4, 1992, pp. 197-226.

McFarlin, et al., J. Am. Chem. Soc. 1958, 80, 5372-76.

Mikhailov, S.N., et al., "Hydrolysis of 2'- and 3'-C-methyluridine 2'-, 3'-monophosphates and Interconversion and dephosphorylation of the resulting 2'- and 3'-monophosphates: Comparison with the reactions of Uridine monophosphates," J. Org. Chem., vol. 57: 4122-26 (1992).

Mikhailov, S.N., et al., "Substrate properties of C'-methylnucleoside and C'-methyl-2'-deoxynucleoside 5'-triphosphates in RNA and DNA synthesis reactions catalysed by RNA and DNA polymerases," Nucleosides & Nucleotides, 10(1-3): 339-343 (1991).

Miles, et al., "Circular Dichroism of Nucleoside Derivatives. IX. Vicinal Effects on the Circular Dichrosim of Pyrimidine Nucleosides." J. Am. Chem. Soc. 92(13): 3872-3881 (1970).

Moiseyev, et al., "Determination of the nucleotide conformation in the productive enzyme-substrate complexes of RNA-depolymerases." FEBS Letters (1997), 404(2,3), 169-172.

Moore, et al., "Synthesis of Nucleotide Analogues That Potently and Selectively Inhibit Human DNA Primase." Biochemistry (2002). 41(47), 14066-14075.

Nishiguchi, S., et al., "Methods to Detect Substitutions in the Interferon-Sensitivity-Determining Region of Hepatitis C virus 1b for Prediction of Response to Interferon Therapy," Hepatology. Jan. 2001, vol. 33, No. 1, pp. 241-247.

Nishimura, T. et al. "Studies on Sythetic Nuclesides. Trimethylsilyl Derivatives of Pyrmidine and Purines," Chemical & Pharmaceutical Bulletin (1964), vol. 12, pp. 352-356.

Novak, J.J.K. & Sorm, F., "Nucleic Acid Components and Their Analogues. CXX. 2-C-Methyl-D-Ribose and Its Derivatives," Collection Czechoslav. Chem. Commun., 34:857-866 (1969).

Novak, J.J.K., "Chiroptical Properties of 2-Methyl-1,4-Lactones: Revised Absolute Configuration of 2-Deoxy-2-C-Methyl-Erythro-D-Pentono-1, 4-Lactones," Collection Czechoslav. Chem. Commun., 39:869-882 (1974).

Nutt, R. F., et al. "Branched-chain sugar nucleosides. III. 3'-C-methyladenine," J. Org. Chem. 33:1789-95 (1968).

Oivanen, M., et al., "Additional evidence for the exceptional mechanism of the acid-catalyzed hydrolysis of 4-oxopyrimidine nucleosides: Hydrolysis of 1-(1-alkoxyalkyl)uracils, seconucleosides. 3'-C-alkyl nucleosides and nucleoside 3', 5'-cyclic monophosphates," J. Chem. Soc. Perkin Trans. 2, 1994: 309-314 (1994).

Pagliaro, L., et al., "[Hepatology: Old, recent and (maybe) future stories. A narrative review]. Epatologia: IERI, OGGI E (FORSE) Domani," Recenti Progressi in Medicina, (2006) vol. 97, No. 12, pp. 741-750.

Pierra, C., et al., "Comparative Studies of Selected Potential Prodrugs of B-L-dC, A Potent and Selective Anti-HBV Agent," Antiviral Res., 50:A79 (2001), Abstract No. 138.

Pierra, C., et al., "NM 283, and efficient prodrug of the potent anti-HCV agent 2'-C-methylcytidine," Nucleosides, Nucleotides and Nucleic Acids (2005), 24(5-7), 767-770.

Pierra, C., et al., "Synthesis and Pharmacokinetics of Valopicitabine (NM283), and Efficient Prodrug of the Potent Anti-HCV Agent 2'-C-Methylcytidine," Journal of Medicinal Chemistry (2006), 49(22), 6614-6620.

Reist, et al., "Potential anticancer agents. LXXVII. Synthesis of nucleosides of purine-6-thiol(6-mercaptopurine) containing "fraudulent" sugars." Journal of Organic Chemistry (1962), 27 3279-83.

Robins, et al., "Purine Nucleosides. XXIX. The Synthesis of 2'-Deoxy-L-adenosine and 2'-Deoxy-L-guanosine and Their [alpha] Anomers," Journal of Organic Chemistry, 35(3), 636-639 (Mar. 1970).

Rong, et al., "The Synthesis and Conformation of 2'-and 3'-Hypermodified Tricyclic Nucleosides and Their Use in the Synthesis of Novel 2'- or 3'-Isomeric 4(7)-Substituted Isoxazolidine-nucleosides," Tetrahedron vol. 50, No. 16, pp. 4921-4936. (1994).

Roque-Afonso, AM, et al., "Performance of Trugene hepatitis C virus5' noncoding genotyping kit, a new Clip sequencing-based assay for hepatitis C virus genotype determination," Journal of Viral Hepatitis. Sep. 2002, vol. 9, Issue 5, pp. 385-389.

Sakthivel, et al. "Electrophilic fluorination of 5-(cyanomethyl)imidazole-4-carboxylate nucleosides: Facile entry to 3-fluoro-3- deazaguanosine analogues." Synlett (2005), (10), 1586-1590.

Sakthivel, et al., "Direct SNAr amination of fluorinated imidazo[4,5-c]pyridine nucleosides: efficient syntheses of 3-fluoro-3deazaadenosine analogs." Tetrahedron Letters (2005), 46(22), 3883-3887.

Salidino, R., et al., "A new and efficient synthesis of cytidine and adenosine derivatives by dimethyldioxirane oxidation of thiopyrimidine and thiopurine nucleosides," J. chem. Soc., Perkin Trans. I., 21: 3053-3054 (1994).

Samano, et al., "Nucleic Acid Related Compounds. 77. 2',3'-Didehydro-2', 3'-Dideoxy-2' (and 3')-Methylnucleosides Via [3,3]-Sigmatropic Rearrangements of 2'(and 3')-Methylene-3'(and 2')-O-Thiocarbonyl Derivatives and Radical Reuction of a 2'-Chloro-3'Methylene Analogue," Can. J. Chem., 71: 186-191 (1993).

Samano, et al., "Synthesis and Radical-Induced Ring-Opening Reactions of 2'-Deoxyadenosine-2'-Spirocyclopropane and its Uridine analogue. Mechanistic Probe for Ribonucleotide Reductases," J Am Chem Soc, 114: 4007-08 (1992).

Sandhu, et al., "Evaluation of microdosing strategies for studies in preclinical drug development: Demonstration of linear pharmacokinetics in dogs of a nucleoside analog over a 50-fold dose range." Drug Metabolism and Disposition (2004), 32(11), 1254-1259.

Sato, et al., "C-Nucleoside synthesis. 10. Synthesis of 2'-methylated pyrimidine C-nucleosides." Tetrahedron Letters (1980), 21(20), 1971-4.

Sato, et al., "C-Nucleoside synthesis. 19. Stereocontrolled general synthesis of pyrimidine C-nucleosides having branched-chain sugar moieties." Bulletin of the Chemical Society of Japan (1983), 56(9), 2680-99.

Savochkina, et al., "Substrate properties of c—methylnucleoside triphosphates in RNA syntheses catalyzed by *e. coli* RNA polymeruse" Molecular Biology, 1989, v. 23, No. 6.

Scheibler, C., "Ueber das Saccharin und die Saccharinsaure," Chemische Berichte, 13:2212-2217 (1880). In German.

Schiff, E.R., "Emerging strategies for pegylated interferon combination therapy," Nature Clinical Practice Gastoenterology and Hepatology, (2007) vol. 4, No. SUPPL. I. pp. S17-S21.

Schmit, C., et al., "The effects of 2'- and 3'-alkyl substituents on oligonucleotide hybridization and stability," Bioorg. & Med. Chem. Lett., 4(16): 1969-1974 (1994).

Serafinowski, P.J., et al., "New method for the preparation of some 2'- and 3'-trifluoromethyl-2',3'-dideoxyuridine derivatives," Tetrahedron, 56(2):333-339 (1999).

Shalaby, et al., "Conformations and Structure Studies of Sugar Lactones in the Solid State. Part 11. The Molecular Structure of a-D-Glucosaccharino-Y-Lactone: 2-C-Mehtyl-D-Ribo-Pentono-1,4-lactone." Carbohydrate Research (1994), 264(2), 191-8.

Shi, et al., Synthesis and in vitro Anti-HCV Activity of β-d- and 1-2'-Deoxy-2'-Fluororibonucleosides, Nucleosides, Nucleotides & Nucleic Acids 2005, vol. 23, Nos. 5-7, pp. 875-879.

Shim, Jae H., "Recent patents on nucleoside and nucleotide inhibitors for HCV," Recetn Patents on Anti-Infective Drug Discovery (2006), 1(3), 323-331.

Sinko, et al., Carrier-Mediated Intestinal Absorption of Valacyclovir, the L-Valyl Ester Prodrug of Acyclovir. Biopharmaceutics & Drug Disposition 1998, vol. 19, pp. 209-217.

Sinkula et al., "Rationale for design of biologically reversible drug derivatives: prodrugs," *J. Pharm. Set.*, 1975,64: 181-210.

Smith, et al., "Synthesis of new 2'-b-C-methyl related triciribine analogues as anti-HCV agents." Valeant Pharmaceuticals International, Costa Mesa, CA, USA. Bioorganic & Medicinal Chemistry Letters (2004), 14(13), 3517-3520.

Song, et al., Amino Acid Ester Prodrugs of the Anticancer Agent Gemcitabine: Synthesis, Bioconversion, Metabolic Bioevasion, and hPEPT1-Medicated Transport, Moleculare Pharmaceutics (2005), 2(2), 157-167.

Sorbera, L.A., et al., "Valopicitabine: anti-hepatitis C virus drug RNA—directed RNA polymerase (NS5B) inhibitor," Drugs of the Future (2006), 31(4), 320-324.

Sowden, J., "The Saccharinic Acids," Adv. Carbohydrate Chem., 12:43-46 (1957).

Spardari, et al., "L-Thmidine is Phosphorylated by Herpes Simplex Virus Type 1 Thymidine Kinase and Inhibits Viral Growth," Journal of Medicinal Chemistry, 35(22), 4214-4220 (1992).

Standring, D.N., et al., "Antiviral Beta-L-Nucleosides Specific for Hepatitis B Virus Infection," Antiviral Chem. & Chemother., 12 (Suppl. 1): 119-129 (2001).

Stuyver, et al., "Ribonucleoside Analogue That Block Replication of Bovine Viral Diarrhea and Hepatits C Viruses in Culture." Antimicrobial Agents and Chemotherapy, vol. 47, No. 1, Jan. 2003, p. 244-254.

Sundberg, et al., Advanced Organic Chemistry, Part b, 1990, pp. 232 and 236.

Takenuki, et al., "Nucleosides and nucleotides. XLIII. On the stereoselectivity of alkyl addition reaction of pyrimidine 2'-ketonucleosides." Chemical & Pharmaceutical Bulletin (1990), 38(11), 2947-52.

Tang. X.-Q., et al., "2'-C-Branched Ribonucleosides: Synthesis of the Phophoramidite Derivatives of 2'-C-B-Methylcytidine and Their Incorporation into Oligonucleotides," J. Org. Chem., 64(3): 747-754 (1999).

The Merck Index, 12th edition, 1996, p. 275.

Tritsch, D., et al., "3'-β-ethynyl and 2'-deoxy-3'-β-ethynyl adenosines: First 3'-β-branched adenosine substrates of adenosine deaminase," Bioorg. & Med. Chem. Lett., 10: 139-141 (2000).

Tunitskaya, V.L., et al., "Substrate properties of C'-methyl UTP derivatives in T7 RNA polymerase reactions. Evidence for N-type NTP conformation," FEBS Letters, 400: 263-266 (1997).

Tyrsted, G., et al., "Inhibition of the synthesis of 5-phosphoribosyl-1-pyrophosphate by 3'-deoxyadenosine and structurally related nucleoside analogs," Biochem. Biophys. Acta., 155(2): 619-622 (Feb. 26, 1968).

Usui, H., et al., "Synthesis of 2'-deoxy-8,2'-ethanoadenosine and 3'-deoxy-8,3'-ethanoadenosine (Nucleotides & Nucleosides. LXIV)," Chem. Pharm. Bull., 34(1):15-23 (1986).

Verri, A., et al., "Lack of enantiospecificity of human 2'-deoxycytidine kinase: relevance for the activetion of B-L-deoxyctidine analogs as antineolastic and antiviral agents," Molecular Pharmacology, 51(1): 132-138 (Jan. 1997).

Verri, a., et al., "Relaxed Enantioselectivity of Human Mitochondrial Thymidine Knase and Chemotherapeutic Uses of L-Nucleoside Analogues," Biochem. J., 328(1): 317-320 (Nov. 15, 1997).

Von Buren, et al., "Branched oligodeoxynucleotides: automated synthesis and triple helical hybridization studies." Tetrahedron (1995), 51(31), 8491-506.

Von Janta-Lipinski, M., et al., "Newly Synthesized L-Enantiomers of 3'-Fluoro-Modified B-2'-Deoxyribonucleoside 5'-Triphosphates Inhibit Hepatitis B DNA Polymerase but not the Five Cellular SNA Polymerases a, B, y, d and E Nor HIV-1 Reverse Transciptase," J. Medicinal Chemistry, 41(12): 2040-2046 (May 21, 1998).

Wagner, D., et al., "Preparation and Synthetic Utility of Some Organotin Derivatives of Nucleosides," J. Org. Chem., 39(1):24-30 (1974).

Walczak, K., et al., "Synthesis of 1-(3-alkyl-2,3-dideoxy-D-pentofuranosyl)uracils with potential anti-HIV activity," Acta Chemica Scand., 45: 930-934 (1991).

Walton et al., "Branched-chain sugar nucleosides. A new type of biologically active nucleoside," *J. Am. Chem. Soc.*, 88(19): 4524-25 (1966).

Walton, et al., "Branched-Chain Sugar Nucleosides: V. Synthesis and Antiviral Properties of Several Branched-Chain Sugar Nucleosides," Antiviral Nucleosides, vol. 12: 306-309 (1969).

Whistler, R. L., and BeMiller, J.N., "[118] 'a'-D-Glucosaccharino-1,4-Lactone," Methods in Carbohydrate Chemistry, 2:484-485 (1963).

Wohnsland, A., et al., "Viral determinants of resistance to treatment in patients with hepatitis C," Clinical Microbiology reviews, (2007) vol. 20, No. 1, pp. 23-38.

Wolfe, et al., Tetrahedron Letters, vol. 36(42): 7611-14 (1995).

Wu, et al., Targeting NS5B RNA-dependent RNA polymerase for anti-HCV chemotherapy. Current Drug Targets—Infectious Disorders 2003, vol. 3, p. 207-219.

Wu, et al., "A New Stereospecific Synthesis of [3.1.0] Cicyclic Cyclopropano Analog of 2',3'-Dideoxyuridine." Tetrahedron, vol. 46, 1990, pp. 2587-2592.

Zedeck et al., "Inhibition of the steroid induced synthesis of Δ5-3-ketosteroid isomerase in *Pseudomonas testosteroni* by a new purine deoxyribonucleoside analog: 6-chloro-8aza-9-cyclopentylpurinc," Mol. Phys., 3(4):386-95 (1967).

Zemlicka, J., et al. "Aminoacyl Derivatives of Nucleosides, Nucleotides, and polynucleotides. VIII. The Preparation of 2'(3)—O-L-Phenylalanyluridine, -cytidenie,—Adensonine, -inosine, -guanosine and 2'-Deoxy-3'O-L-Phenylalanyladenosine," Collection Czecoslov, Chem. Commun. 1969, vol. 43, No. 13, 3755-3767.

Zemlicka, J., et al., "Substrate Specificity of Ribosomal Peptidyltransferase. Peditidyltranferase. Effect of Modifications in the Heterocyclic, Carbohydrate and Amino Acid Moiety of 2'(3)-O-L-Phenyladenosine." Biochemistry. Dec. 2, 1975, vol. 14, No. 24, 5239-5249.

Zhou, et al., Pharmacokinetics and pharmacodynamics of valopicitabine. Journal of Hepatology 2005, vol. 42 (Suppl. 2), p. 229.

Zinchenko, et al., "2', 3' & .5'—uridine methyl derivatives in microbiological transelicozilation." Doklady Akad Nauk v.297(3), pp. 731-734 (1987).

Zinchenko, et al., "Substrate specificity of uridine and purine nucleoside phosporlases in whole cells of *e. coli*" Bioplymers & a cell, 1988, v. 4, No. 6.

Zinichenko, et al., "Substrate Specificity of Uridine and Purine Nucleoside Phosphorylascs of the Whole Cells of *Escherichia Coli*." Nucleic Acids Research. Symposium Series No. 18., 1987. pp. 137-140.

Office Action dated Oct. 1, 2003 from U.S. Appl. No. 09/863,816.
Notice of Allowance dated Jun. 23, 2004 from U.S. Appl. No. 09/863,816.
Office Action dated Aug. 27, 2003 from U.S. Appl. No. 09/864,078.
Notice of Allowance dated Feb. 19, 2004 from U.S. Appl. No. 09/864,078.
Notice of Allowance dated May 17, 2005 from U.S. Appl. No. 10/602,135.
Office Action dated Apr. 5, 2005 from U.S. Appl. No. 10/602,135.
Notice of Allowance dated Mar. 9, 2006 from U.S. Appl. No. 10/602,136.
Office Action dated Jul. 28, 2006 from U.S. Appl. No. 10/602,142.
Office Action dated Sep. 20, 2007 from U.S. Appl. No. 10/602,142.
Office Action dated Dec. 10, 2008 from U.S. Appl. No. 10/602,142.
Office Action dated Nov. 15, 2005 from U.S. Appl. No. 10/602,142.
Office Action dated Mar. 29, 2007 from U.S. Appl. No. 10/602,142.
Office Action dated Feb. 26, 2008 from U.S. Appl. No. 10/602,142.
Office Action dated May 30, 2006 from U.S. Appl. No. 10/602,691.
Office Action dated Aug. 22, 2007 from U.S. Appl. No. 10/602,691.
Office Action dated Oct. 7, 2008 from U.S. Appl. No. 10/602,691.
Office Action dated Dec. 29. 2006 from U.S. Appl. No. 10/602,691.
Office Action dated Nov. 7, 2005 from U.S. Appl. No. 10/602,691.
Office Action dated Feb. 26, 2008 from U.S. Appl. No. 10/602,691.
Notice of Allowance dated Dec. 28, 2005 from U.S. Appl. No. 10/602,692.
Office Action dated Apr. 5, 2005 from U.S. Appl. No. 10/602,692.
Notice of Allowance dated Dec. 27, 2005 from U.S. Appl. No. 10/602,693.
Office Action dated Apr. 6, 2005 from U.S. Appl. No. 10/602,693.
Notice of Allowance dated Dec. 27, 2005 from U.S. Appl. No. 10/602,694.
Office Action dated Apr. 6, 2005 from U.S. Appl. No. 10/602,694.
Office Action dated Sep. 10, 2004 from U.S. Appl. No. 10/602,976.
Office Action dated May 19, 2005 from U.S. Appl. No. 10/602,976.
Notice of Allowance dated Oct. 13, 2005 from U.S. Appl. No. 10/602,976.
Office Action dated Aug. 15, 2006 from U.S. Appl. No. 10/608,907.
Office Action dated May 31, 2007 from U.S. Appl. No. 10/608,907.
Office Action dated Jan. 28, 2008 from U.S. Appl. No. 10/608,907.
Office Action dated Nov. 26, 2008 from U.S. Appl. No. 10/608,907.
Office Action dated Aug. 2, 2006 from U.S. Appl. No. 10/609,298.
Office Action dated Jul. 10, 2008 from U.S. Appl. No. 10/609,298.
Office Action dated Oct. 5, 2005 from U.S. Appl. No. 11/005,440.
Office Action dated Dec. 5, 2006 from U.S. Appl. No. 11/005,440.
Office Action dated Jun. 13, 2007 from U.S. Appl. No. 11/005,440.
Office Action dated Oct. 16, 2007 from U.S. Appl. No. 11/005,440.
Office Action dated Aug. 21, 2006 from U.S. Appl. No. 11/005,441.
Notice of Allowance dated Jun. 22, 2007 from U.S. Appl. No. 11/005,441.
Notice of Allowance dated Jan. 8, 2008 from U.S. Appl. No. 11/005,441.
Office Action dated Aug. 7, 2006 from U.S. Appl. No. 11/005,442.
Office Action dated May 16, 2007 from U.S. Appl. No. 11/005,442.
Office Action dated Nov. 28, 2007 from U.S. Appl. No. 11/005,442.

* cited by examiner where: R = H

| Lane # | template | → |
|---|---|---|
| 1-2 | (-21) | 3' CAUAU<u>G</u>CUCUUAAUCUUUUCC |
| 3-4 | (-21)-7G | 3' CAUAU<u>GG</u>UCUUAAUCUUUUCC |
| 5-6 | (-21)-9G | 3' CAUAU<u>G</u>CU<u>G</u>UUAAUCUUUUCC |
| 7-8 | (-21)-6C/7G | 3' CAUAUC<u>G</u>UCUUAAUCUUUUCC |
| 9-10 | (-21)-6C/9G | 3' CAUAUCCU<u>G</u>UUAAUCUUUUCC |
| 11-12 | (-21)-6C/15G | 3' CAUAUCCUCUUAAU<u>G</u>UUUUCC |

Figure 9
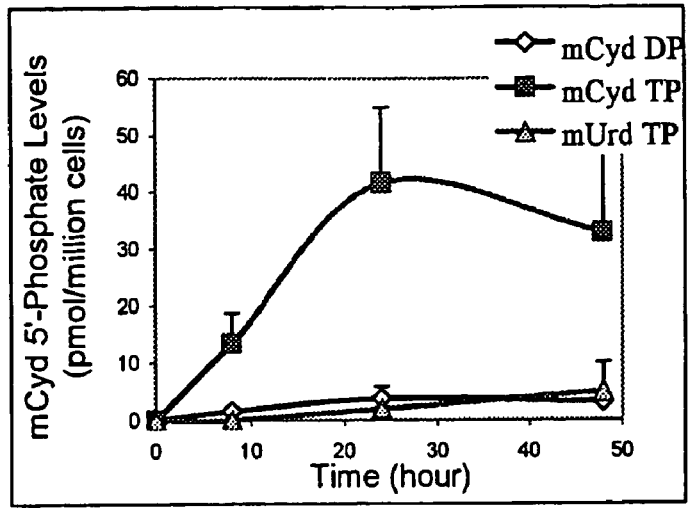
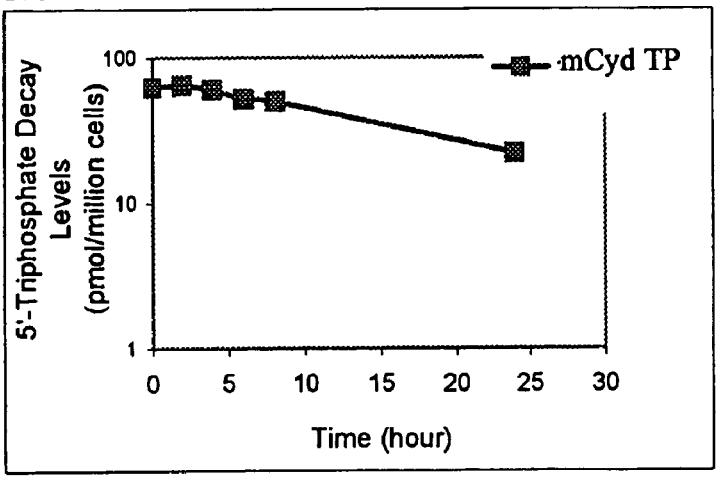
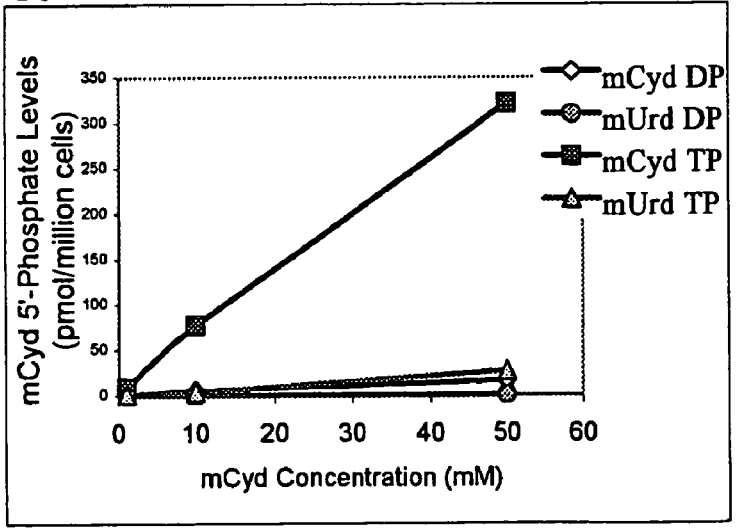

2'-C-METHYL-3'-O-L-VALINE ESTER RIBOFURANOSYL CYTIDINE FOR TREATMENT OF FLAVIVIRIDAE INFECTIONS

CROSS-REFERENCE TO RELATED APPLICATIONS

This application is a continuation of U.S. patent application Ser. No. 10/607,909, filed Jun. 27, 2003, now U.S. Pat. No. 7,456,155, which claims the benefit of priority to U.S. Provisional application No. 60/392,351, filed Jun. 28, 2002, the disclosure of which is incorporated herein by reference.

PARTIES TO A JOINT RESEARCH AGREEMENT

The subject matter of this application arises in part from a joint research agreement between Idenix Pharmaceuticals, Inc., Universita Degli Studi di Cagliari, Centre National de la Recherche Scientifique, and L'Université Montpellier II.

FIELD OF THE INVENTION

This invention is in the area of pharmaceutical chemistry and, in particular, is 2'-C-methyl-ribofuranosyl cytidine-3'-O-L-valine ester and pharmaceutically acceptable salts, derivatives and prodrugs thereof, their syntheses and their uses as anti-Flaviviridae agents in the treatment of hosts, notably humans, infected with a Flaviviridae, and in particular, hepatitis C, virus.

BACKGROUND OF THE INVENTION

Flaviviridae Viruses

The Flaviviridae family of viruses comprises at least three distinct genera: pestiviruses, which cause disease in cattle and pigs; flaviviruses, which are the primary cause of diseases such as dengue fever and yellow fever; and hepaciviruses, whose sole member is HCV. The flavivirus genus includes more than 68 members separated into groups on the basis of serological relatedness (Calisher et al., *J. Gen. Virol*, 1993, 70, 37-43). Clinical symptoms vary and include fever, encephalitis and hemorrhagic fever (*Fields Virology*, Editors: Fields, B. N., Knipe, D. M., and Howley, P. M., Lippincott-Raven Publishers, Philadelphia, Pa., 1996, Chapter 31, 931-959). Flaviviruses of global concern that are associated with human disease include the dengue hemorrhagic fever viruses (DHF), yellow fever virus, shock syndrome and Japanese encephalitis virus (Halstead, S. B., *Rev. Infect. Dis.*, 1984, 6, 251-264; Halstead, S. B., *Science*, 239:476-481, 1988; Monath, T. P., *New Eng. J. Med*, 1988, 319, 641-643).

The pestivirus genus includes bovine viral diarrhea virus (BVDV), classical swine fever virus (CSFV, also called hog cholera virus) and border disease virus (BDV) of sheep (Moennig, V. et al. *Adv. Vir. Res.* 1992, 41, 53-98). Pestivirus infections of domesticated livestock (cattle, pigs and sheep) cause significant economic losses worldwide. BVDV causes mucosal disease in cattle and is of significant economic importance to the livestock industry (Meyers, G. and Thiel, H.-J., *Advances in Virus Research*, 1996, 47, 53-118; Moennig V., et al, *Adv. Vir. Res.* 1992, 41, 53-98). Human pestiviruses have not been as extensively characterized as the animal pestiviruses. However, serological surveys indicate considerable pestivirus exposure in humans.

Pestiviruses and hepaciviruses are closely related virus groups within the Flaviviridae family. Other closely related viruses in this family include the GB virus A, GB virus A-like agents, GB virus-B and GB virus-C (also called hepatitis G virus, HGV). The hepacivirus group (hepatitis C virus; HCV) consists of a number of closely related but genotypically distinguishable viruses that infect humans. There are approximately 6 HCV genotypes and more than 50 subtypes. Due to the similarities between pestiviruses and hepaciviruses, combined with the poor ability of hepaciviruses to grow efficiently in cell culture, bovine viral diarrhea virus (BVDV) is often used as a surrogate to study the HCV virus.

The genetic organization of pestiviruses and hepaciviruses is very similar. These positive stranded RNA viruses possess a single large open reading frame (ORF) encoding all the viral proteins necessary for virus replication. These proteins are expressed as a polyprotein that is co- and post-translationally processed by both cellular and virus-encoded proteinases to yield the mature viral proteins. The viral proteins responsible for the replication of the viral genome RNA are located within approximately the carboxy-terminal. Two-thirds of the ORF are termed nonstructural (NS) proteins. The genetic organization and polyprotein processing of the nonstructural protein portion of the ORF for pestiviruses and hepaciviruses is very similar. For both the pestiviruses and hepaciviruses, the mature nonstructural (NS) proteins, in sequential order from the amino-terminus of the nonstructural protein coding region to the carboxy-terminus of the ORF, consist of p7, NS2, NS3, NS4A, NS4B, NS5A, and NS5B.

The NS proteins of pestiviruses and hepaciviruses share sequence domains that are characteristic of specific protein functions. For example, the NS3 proteins of viruses in both groups possess amino acid sequence motifs characteristic of serine proteinases and of helicases (Gorbalenya et al. (1988) Nature 333:22; Bazan and Fletterick (1989) Virology 171: 637-639; Gorbalenya et al. (1989) Nucleic Acid Res. 17.3889-3897). Similarly, the NS5B proteins of pestiviruses and hepaciviruses have the motifs characteristic of RNA-directed RNA polymerases (Koonin, E. V. and Doija, V. V. (1993) Crit. Rev. Biochem. Molec. Biol. 28:375-430).

The actual roles and functions of the NS proteins of pestiviruses and hepaciviruses in the lifecycle of the viruses are directly analogous. In both cases, the NS3 serine proteinase is responsible for all proteolytic processing of polyprotein precursors downstream of its position in the ORF (Wiskerchen and Collett (1991) Virology 184:341-350; Bartenschlager et al. (1993) J. Virol. 67:3835-3844; Eckart et al. (1993) Biochem. Biophys. Res. Comm. 192:399-406; Grakoui et al. (1993) J. Virol. 67:2832-2843; Grakoui et al. (1993) *Proc. Natl. Acad. Sci. USA* 90:10583-10587; Hijikata et al. (1993) J. Virol. 67:4665-4675; Tome et al. (1993) J. Virol. 67:4017-4026). The NS4A protein, in both cases, acts as a cofactor with the NS3 serine protease (Bartenschlager et al. (1994) J. Virol. 68:5045-5055; Failla et al. (1994) J. Virol. 68: 3753-3760; Lin et al. (1994) 68:8147-8157; Xu et al. (1997) J. Virol. 71:5312-5322). The NS3 protein of both viruses also functions as a helicase (Kim et al. (1995) Biochem. Biophys. Res. Comm. 215: 160-166; Jin and Peterson (1995) Arch. Biochem. Biophys., 323:47-53; Warrener and Collett (1995) J. Virol. 69:1720-1726). Finally, the NS5B proteins of pestiviruses and hepaciviruses have the predicted RNA-directed RNA polymerases activity (Behrens et al. (1996) EMBO J. 15:12-22; Lchmann et al. (1997) J. Virol. 71:8416-8428; Yuan et al. (1997) Biochem. Biophys. Res. Comm. 232:231-235; Hagedom, PCT WO 97/12033; Zhong et al. (1998) J. Virol. 72.9365-9369).

Hepatitis C Virus

The hepatitis C virus (HCV) is the leading cause of chronic liver disease worldwide. (Boyer, N. et al. *J. Hepatol.* 32:98-112, 2000). HCV causes a slow growing viral infection and is the major cause of cirrhosis and hepatocellular carcinoma (Di Besceglie, A. M. and Bacon, B. R., *Scientific American*, Oct.: 80-85, (1999); Boyer, N. et al. *J. Hepatol.* 32:98-112, 2000). An estimated 170 million persons are infected with HCV worldwide. (Boyer, N. et al. *J. Hepatol.* 32:98-112, 2000). Cirrhosis caused by chronic hepatitis C infection accounts for 8,000-12,000 deaths per year in the United States, and HCV infection is the leading indication for liver transplantation.

HCV is known to cause at least 80% of posttransfusion hepatitis and a substantial proportion of sporadic acute hepatitis. Preliminary evidence also implicates HCV in many cases of "idiopathic" chronic hepatitis, "cryptogenic" cirrhosis, and probably hepatocellular carcinoma unrelated to other hepatitis viruses, such as Hepatitis B Virus (HBV). A small proportion of healthy persons appear to be chronic HCV carriers, varying with geography and other epidemiological factors. The numbers may substantially exceed those for HBV, though information is still preliminary; how many of these persons have subclinical chronic liver disease is unclear. (The Merck Manual, ch. 69, p. 901, 16th ed., (1992)).

HCV is an enveloped virus containing a positive-sense single-stranded RNA genome of approximately 9.4 kb. The viral genome consists of a 5' untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation. Translation of the HCV genome is initiated by a cap-independent mechanism known as internal ribosome entry. This mechanism involves the binding of ribosomes to an RNA sequence known as the internal ribosome entry site (IRES). An RNA pseudoknot structure has recently been determined to be an essential structural element of the HCV IRES. Viral structural proteins include a nucleocapsid core protein (C) and two envelope glycoproteins, E1 and E2. HCV also encodes two proteinases, a zinc-dependent metalloproteinase encoded by the NS2-NS3 region and a serine proteinase encoded in the NS3 region. These proteinases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown.

A significant focus of current antiviral research is directed to the development of improved methods of treatment of chronic HCV infections in humans (Di Besceglie, A. M. and Bacon, B. R., *Scientific American, October:* 80-85, (1999)).

Treatment of HCV Infection with Interferon

Interferons (IFNs) have been commercially available for the treatment of chronic hepatitis for nearly a decade. IFNs are glycoproteins produced by immune cells in response to viral infection. IFNs inhibit replication of a number of viruses, including HCV, and when used as the sole treatment for hepatitis C infection, IFN can in certain cases suppress serum HCV-RNA to undetectable levels. Additionally, IFN can normalize serum amino transferase levels. Unfortunately, the effect of IFN is temporary and a sustained response occurs in only 8%-9% of patients chronically infected with HCV (Gary L. Davis. *Gastroenterology* 118:S104-S114, 2000). Most patients, however, have difficulty tolerating interferon treatment, which causes severe flu-like symptoms, weight loss, and lack of energy and stamina.

A number of patents disclose Flaviviridae, including HCV, treatments, using interferon-based therapies. For example, U.S. Pat. No. 5,980,884 to Blatt et al. discloses methods for retreatment of patients afflicted with HCV using consensus interferon. U.S. Pat. No. 5,942,223 to Bazer et al. discloses an anti-HCV therapy using ovine or bovine interferon-tau. U.S. Pat. No. 5,928,636 to Alber et al. discloses the combination therapy of interleukin-12 and interferon alpha for the treatment of infectious diseases including HCV. U.S. Pat. No. 5,849,696 to Chretien et al. discloses the use of thymosins, alone or in combination with interferon, for treating HCV. U.S. Pat. No. 5,830,455 to Valtuena et al. discloses a combination HCV therapy employing interferon and a free radical scavenger. U.S. Pat. No. 5,738,845 to Imakawa discloses the use of human interferon tau proteins for treating HCV. Other interferon-based treatments for HCV are disclosed in U.S. Pat. No. 5,676,942 to Testa et al., U.S. Pat. No. 5,372,808 to Blatt et al., and U.S. Pat. No. 5,849,696. A number of patents also disclose pegylated forms of interferon, such as, U.S. Pat. Nos. 5,747,646, 5,792,834 and 5,834,594 to Hoffmann-La Roche Inc; PCT Publication No. WO 99/32139 and WO 99/32140 to Enzon; WO 95/13090 and U.S. Pat. Nos. 5,738, 846 and 5,711,944 to Schering; and U.S. Pat. No. 5,908,621 to Glue et al.

Interferon alpha-2a and interferon alpha-2b are currently approved as monotherapy for the treatment of HCV. ROFERON®-A (Roche) is the recombinant form of interferon alpha-2a. PEGASYS® (Roche) is the pegylated (i.e. polyethylene glycol modified) form of interferon alpha-2a. INTRON®A (Schering Corporation) is the recombinant form of Interferon alpha-2b, and PEG-INTRON® (Schering Corporation) is the pegylated form of interferon alpha-2b.

Other forms of interferon alpha, as well as interferon beta, gamma, tau and omega are currently in clinical development for the treatment of HCV. For example, INFERGEN (interferon alphacon-1) by InterMune, OMNIFERON (natural interferon) by Viragen, ALBUFERON by Human Genome Sciences, REBIF (interferon beta-1a) by Ares-Serono, Omega Interferon by BioMedicine, Oral Interferon Alpha by Amarillo Biosciences, and interferon gamma, interferon tau, and interferon gamma-1b by InterMune are in development.

Ribivarin

Ribavirin (1-β-D-ribofuranosyl-1-1,2,4-triazole-3-carboxamide) is a synthetic, non-interferon-inducing, broad spectrum antiviral nucleoside analog sold under the trade name, Virazole (The Merck Index, 11th edition, Editor: Budavari, S., Merck & Co., Inc., Rahway, N.J., p 1304, 1989). U.S. Pat. No. 3,798,209 and RE29,835 disclose and claim ribavirin. Ribavirin is structurally similar to guanosine, and has in vitro activity against several DNA and RNA viruses including Flaviviridae (Gary L. Davis. *Gastroenterology* 118:S104-S114, 2000).

Ribavirin reduces serum amino transferase levels to normal in 40% of patients, but it does not lower serum levels of HCV-RNA (Gary L. Davis. *Gastroenterology* 118:S104-S114, 2000). Thus, ribavirin alone is not effective in reducing viral RNA levels. Additionally, ribavirin has significant toxicity and is known to induce anemia.

Ribavirin is not approved fro monotherapy against HCV. It has been approved in combination with interferon alpha-2a or interferon alpha-2b for the treatment of HCV.

Combination of Interferon and Ribavirin

The current standard of care for chronic hepatitis C is combination therapy with an alpha interferon and ribavirin.

The combination of interferon and ribavirin for the treatment of HCV infection has been reported to be effective in the treatment of interferon naïve patients (Battaglia, A. M. et al., *Ann. Pharmacother.* 34:487-494, 2000), as well as for treatment of patients when histological disease is present (Berenguer, M. et al. *Antivir. Ther.* 3(Suppl. 3):125-136, 1998). Studies have show that more patients with hepatitis C respond to pegylated interferon-alpha/ribavirin combination therapy than to combination therapy with unpegylated interferon alpha. However, as with monotherapy, significant side effects develop during combination therapy, including hemolysis, flu-like symptoms, anemia, and fatigue. (Gary L. Davis. *Gastroenterology* 118:S104-S114, 2000).

Combination therapy with PEG-INTRON® (peginterferon alpha-2b) and REBETOL® (Ribavirin, USP) Capsules is available from Schering Corporation. REBETOL® (Schering Corporation) has also been approved in combination with INTRON® A (Interferon alpha-2b, recombinant, Schering Corporation). Roche's PEGASYS® (pegylated interferon alpha-2a) and COPEGUS® (ribavirin) are also approved for the treatment of HCV.

PCT Publication Nos. WO 99/59621, WO 00/37110, WO 01/81359, WO 02/32414 and WO 03/024461 by Schering Corporation disclose the use of pegylated interferon alpha and ribavirin combination therapy for the treatment of HCV. PCT Publication Nos. WO 99/15194, WO 99/64016, and WO 00/24355 by Hoffmann-La Roche Inc also disclose the use of pegylated interferon alpha and ribavirin combination therapy for the treatment of HCV.

Additional Methods to Treat Flaviviridae Infections

The development of new antiviral agents for flaviviridae infections, especially hepatitis C, is currently underway. Specific inhibitors of HCV-derived enzymes such as protease, helicase, and polymerase inhibitors are being developed. Drugs that inhibit other steps in HCV replication are also in development, for example, drugs that block production of HCV antigens from the RNA (IRES inhibitors), drugs that prevent the normal processing of HCV proteins (inhibitors of glycosylation), drugs that block entry of HCV into cells (by blocking its receptor) and nonspecific cytoprotective agents that block cell injury caused by the virus infection. Further, molecular approaches are also being developed to treat hepatitis C, for example, ribozymes, which are enzymes that break down specific viral RNA molecules, and antisense oligonucleotides, which are small complementary segments of DNA that bind to viral RNA and inhibit viral replication, are under investigation. A number of HCV treatments are reviewed by Bymock et al. in *Antiviral Chemistry & Chemotherapy*, 11:2; 79-95 (2000) and De Francesco et al. in *Antiviral Research*, 58: 1-16 (2003).

Examples of classes of drugs that are being developed to treat Flaviviridae infections include:

(1) Protease Inhibitors

Substrate-based NS3 protease inhibitors (Attwood et al, Antiviral peptide derivatives, PCT WO 98/22496, 1998; Attwood et al., *Antiviral Chemistry and Chemotherapy* 1999, 10, 259-273; Attwood et al, Preparation and use of amino acid derivatives as anti-viral agents, German Patent Pub. DE 19914474; Tung et al. Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate (Llinas-Brunet et al, Hepatitis C inhibitor peptide analogues, PCT WO 99/07734) are being investigated.

Non-substrate-based NS3 protease inhibitors such as 2,4,6-trihydroxy-3-nitro-benzamide derivatives (Sudo K. et al, *Biochemical and Biophysical Research Communications*, 1997, 238, 643-647; Sudo K. et al. *Antiviral Chemistry and Chemotherapy*, 1998, 9, 186), including RD3-4082 and RD3-4078, the former substituted on the amide with a 14 carbon chain and the latter processing a para-phenoxyphenyl group are also being investigated.

Sch 68631, a phenanthrenequinone, is an HCV protease inhibitor (Chu M. et al., *Tetrahedron Letters* 37:7229-7232, 1996). In another example by the same authors, Sch 351633, isolated from the fungus *Penicillium griseofulvum*, was identified as a protease inhibitor (Chu M. et al., *Bioorganic and Medicinal Chemistry Letters* 9:1949-1952). Nanomolar potency against the HCV NS3 protease enzyme has been achieved by the design of selective inhibitors based on the macromolecule eglin c. Eglin c, isolated from leech, is a potent inhibitor of several serine proteases such as *S. griseus* proteases A and B, α-chymotrypsin, chymase and subtilisin. Qasim M. A. et al., *Biochemistry* 36:1598-1607, 1997.

Several U.S. patents disclose protease inhibitors for the treatment of HCV. For example, U.S. Pat. No. 6,004,933 to Spruce et al. discloses a class of cysteine protease inhibitors for inhibiting HCV endopeptidase 2. U.S. Pat. No. 5,990,276 to Zhang et al. discloses synthetic inhibitors of hepatitis C virus NS3 protease. The inhibitor is a subsequence of a substrate of the NS3 protease or a substrate of the NS4A cofactor. The use of restriction enzymes to treat HCV is disclosed in U.S. Pat. No. 5,538,865 to Reyes et al. Peptides as NS3 serine protease inhibitors of HCV are disclosed in WO 02/008251 to Corvas International, Inc, and WO 02/08187 and WO 02/008256 to Schering Corporation. HCV inhibitor tripeptides are disclosed in U.S. Pat. Nos. 6,534,523, 6,410,531, and 6,420,380 to Boehringer Ingelheim and WO 02/060926 to Bristol Myers Squibb. Diaryl peptides as NS3 serine protease inhibitors of HCV are disclosed in WO 02/48172 to Schering Corporation. Imidazoleidinones as NS3 serine protease inhibitors of HCV are disclosed in WO 02/08198 to Schering Corporation and WO 02/48157 to Bristol Myers Squibb. WO 98/17679 to Vertex Pharmaceuticals and WO 02/48116 to Bristol Myers Squibb also disclose HCV protease inhibitors.

(2) Thiazolidine derivatives which show relevant inhibition in a reverse-phase HPLC assay with an NS3/4A fusion protein and NS5A/5B substrate (Sudo K. et al., *Antiviral Research*, 1996, 32, 9-18), especially compound RD-1-6250, possessing a fused cinnamoyl moiety substituted with a long alkyl chain, RD4 6205 and RD4 6193;

(3) Thiazolidines and benzanilides identified in Kakiuchi N. et al. *J. EBS Letters* 421, 217-220; Takeshita N. et al. *Analytical Biochemistry*, 1997, 247, 242-246;

(4) A phenan-threnequinone possessing activity against protease in a SDS-PAGE and autoradiography assay isolated from the fermentation culture broth of *Streptomyces* sp., Sch 68631 (Chu M. et al., *Tetrahedron Letters*, 1996, 37, 7229-7232), and Sch 351633, isolated from the fungus *Penicillium griseofulvum*, which demonstrates activity in a scintillation proximity assay (Chu M. et al., *Bioorganic and Medicinal Chemistry Letters* 9, 1949-1952);

(5) Helicase inhibitors (Diana G. D. et al, Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554);

(6) Nucleotide polymerase inhibitors and gliotoxin (Ferrari R. et al. *Journal of Virology*, 1999, 73, 1649-1654), and the natural product cerulenin (Lohmann V. et al., *Virology*, 1998, 249, 108-118);

(7) Antisense phosphorothioate oligodeoxynucleotides (S-ODN) complementary to sequence stretches in the 5' non-coding region (NCR) of the virus (Alt M. et al, *Hepatology*, 1995, 22, 707-717), or nucleotides 326-348 comprising the 3' end of the NCR and nucleotides 371-388 located in the core coding region of the HCV RNA (Alt M. et al., *Archives of Virology*, 1997, 142, 589-599; Galderisi U. et al., *Journal of Cellular Physiology*, 1999, 181, 251-257);

(8) Inhibitors of IRES-dependent translation (Ikeda N et al., Agent for the prevention and treatment of hepatitis C, Japanese Patent Pub. JP-08268890; Kai Y. et al. Prevention and treatment of viral diseases, Japanese Patent Pub. JP-10101591);

(9) Ribozymes, such as nuclease-resistant ribozymes (Maccjak, D. J. et al., *Hepatology* 1999, 30, abstract 995) and those disclosed in U.S. Pat. No. 6,043,077 to Barber et al., and U.S. Pat. Nos. 5,869,253 and 5,610,054 to Draper et al.; and

(10) Nucleoside analogs have also been developed for the treatment of Flaviviridae infections.

Idenix Pharmaceuticals disclosed the use of branched nucleosides in the treatment of flaviviruses (including HCV) and pestiviruses in International Publication Nos. WO 01/90121 and WO 01/92282. Specifically, a method for the treatment of hepatitis C infection (and flaviviruses and pestiviruses) in humans and other host animals is disclosed in the Idenix publications that includes administering an effective amount of a biologically active 1', 2', 3' or 4'-branched β-D or β-L nucleosides or a pharmaceutically acceptable salt or derivative thereof, administered either alone or in combination with another antiviral agent, optionally in a pharmaceutically acceptable carrier.

Other patent applications disclosing the use of certain nucleoside analogs to treat hepatitis C virus include: PCT/CA00/01316 (WO 01/32153; filed Nov. 3, 2000) and PCT/CA01/00197 (WO 01/60315; filed Feb. 19, 2001) filed by BioChem Pharma, Inc. (now Shire Biochem, Inc.); PCT/US02/01531 (WO 02/057425; filed Jan. 18, 2002) and PCT/US02/03086 (WO 02/057287; filed Jan. 18, 2002) filed by Merck & Co., Inc., PCT/EP01/09633 (WO 02/18404; published Aug. 21, 2001) filed by Roche, and PCT Publication Nos. WO 01/79246 (filed Apr. 13, 2001), WO 02/32920 (filed Oct. 18, 2001) and WO 02/48165 by Pharmasset, Ltd.

PCT Publication No. WO 99/43691 to Emory University, entitled "2'-Fluoronucleosides" discloses the use of certain 2'-fluoronucleosides to treat HCV.

Eldrup et al. (Oral Session V, Hepatitis C Virus, Flaviviridae; 16th International Conference on Antiviral Research (Apr. 27, 2003, Savannah, Ga.)) described the structure activity relationship of 2'-modified nucleosides for inhibition of HCV.

Bhat et al. (Oral Session V, Hepatitis C Virus, Flaviviridae, 2003 (Oral Session V, Hepatitis C Virus, Flaviviridae; 16th International Conference on Antiviral Research (Apr. 27, 2003, Savannah, Ga.); p A75) described the synthesis and pharmacokinetic properties of nucleoside analogues as possible inhibitors of HCV RNA replication. The authors report that 2'-modified nucleosides demonstrate potent inhibitory activity in cell-based replicon assays.

Olsen et al. (Oral Session V, Hepatitis C Virus, Flaviviridae; 16th International Conference on Antiviral Research (Apr. 27, 2003, Savannah, Ga.) p A76) also described the effects of the 2'-modified nucleosides on HCV RNA replication.

(11) Other miscellaneous compounds including 1-aminoalkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), benzimidazoles (U.S. Pat. No. 5,891,874 to Colacino et al.), plant extracts (U.S. Pat. No. 5,837,257 to Tsai et al., U.S. Pat. No. 5,725,859 to Omer et al., and U.S. Pat. No. 6,056,961), and piperidenes (U.S. Pat. No. 5,830,905 to Diana et al.).

(12) Other compounds currently in preclinical or clinical development for treatment of hepatitis C virus include: Interleukin-10 by Schering-Plough, IP-501 by Interneuron, Merimebodib (VX-497) by Vertex, AMANTADINE® (Symmetrel) by Endo Labs Solvay, HEP-TAZYME® by RPI, IDN-6556 by Idun Pharma., XTL-002 by XTL., HCV/MF59 by Chiron, CIVACIR® (Hepatitis C Immune Globulin) by NABI, LEVOVIRINS by ICN/Ribapharm, VIRAMIDINE® by ICN/Ribapharm, ZADAXIN® (thymosin alpha-1) by Sci Clone, thymosin plus pegylated interferon by Sci Clone, CEPLENE® (histamine dihydrochloride) by Maxim, VX 950/LY 570310 by Vertex/Eli Lilly, ISIS 14803 by Isis Pharmaceutical/Elan, IDN-6556 by Idun Pharmaceuticals, Inc., JTK 003 by AKROS Pharma, BILN-2061 by Boehringer Ingelheim, CellCept (mycophenolate mofetil) by Roche, T67, a β-tubulin inhibitor, by Tularik, a therapeutic vaccine directed to E2 by Innogenetics, FK788 by Fujisawa Healthcare, Inc., 1 dB 1016 (Siliphos, oral silybin-phosphatdylcholine phytosome), RNA replication inhibitors (VP50406) by ViroPharma/Wyeth, therapeutic vaccine by Intercell, therapeutic vaccine by Epimmune/Genencor, IRES inhibitor by Anadys, ANA 245 and ANA 246 by Anadys, immunotherapy (Therapore) by Avant, protease inhibitor by Corvas/SChering, helicase inhibitor by Vertex, fusion inhibitor by Trimeris, T cell therapy by CellExSys, polymerase inhibitor by Biocryst, targeted RNA chemistry by PTC Therapeutics, Dication by Immtech, Int., protease inhibitor by Agouron, protease inhibitor by Chiron/Medivir, antisense therapy by AVI BioPharma, antisense therapy by Hybridon, hemopurifier by Aethlon Medical, therapeutic vaccine by Merix, protease inhibitor by Bristol-Myers Squibb/Axys, Chron-VacC, a therapeutic vaccine, by Tripep, UT 231B by United Therapeutics, protease, helicase and polymerase inhibitors by Genelabs Technologies, IRES inhibitors by Immusol, R803 by Rigel Pharmaceuticals, INFERGEN® (interferon alphacon-1) by InterMune, OMNIFERON® (natural interferon) by Viragen, ALBUFERON® by Human Genome Sciences, REBIF (interferon beta-1a) by Ares-Serono, Omega Interferon by BioMedicine, Oral Interferon Alpha by Amarillo Biosciences, interferon gamma, interferon tau, and Interferon gamma-1b by InterMune.

Nucleoside prodrugs have been previously described for the treatment of other forms of hepatitis. WO 01/96353 (filed Jun. 15, 2001) to Idenix Pharmaceuticals, discloses 2'-deoxy- β-L-nucleosides and their 3'-prodrugs for the treatment of HBV. U.S. Pat. No. 4,957,924 to Beauchamp discloses various therapeutic esters of acyclovir.

In light of the fact that HCV infection has reached epidemic levels worldwide, and has tragic effects on the infected patient, there remains a strong need to provide new effective pharmaceutical agents to treat hepatitis C that have low toxicity to the host.

Further, given the rising threat of other flaviviridae infections, there remains a strong need to provide new effective pharmaceutical agents that have low toxicity to the host.

Therefore, it is an object of the present invention to provide a compound, method and composition for the treatment of a host infected with hepatitis C virus.

It is another object of the present invention to provide a method and composition generally for the treatment of patients infected with pestiviruses, flaviviruses, or hepaciviruses.

SUMMARY OF THE INVENTION

It has been discovered that the 3'-L-valine ester of β-D-2'-C-methyl-ribofuranosyl cytidine (referred to alternatively below as val-mCyd) provides superior results against flaviviruses and pestiviruses, including hepatitis C virus. Based on this discovery, compounds, compositions, methods and uses are provided for the treatment of flaviviridae, including HCV, that include the administration of an effective amount of val-mCyd or its salt, ester, prodrug or derivative, optionally in a pharmaceutically acceptable carrier. In an alternative embodiment, val-mCyd is used to treat any virus that replicates through an RNA-dependent RNA polymerase.

Therefore, a first embodiment provides a compound of Formula (I), β-D-2'-C-methyl-ribofuranosyl cytidine or a pharmaceutically acceptable salt thereof, and its uses in medical therapy and in the manufacture of a medicant to treat hosts, particularly humans, infected with a flavivirus or pestivirus, including HCV.

The compound val-mCyd is converted to the parent MCyd through de-esterification in the gastrointestinal mucosa, blood or liver, and is actively transported from the gastrointestinal lumen after oral delivery into the bloodstream by an amino acid transporter function in the mucosa of the gastrointestinal tract. This accounts for the increase in oral bioavailability compared to the parent 2'-branched nucleoside that is transported primarily by a nucleoside transporter function. There is also reduced competition with other nucleosides or nucleoside analogs that are transported by the nucleoside transporter function and not the amino acid transporter function. As partial de-esterification occurs prior to complete absorption, the mono or divaline ester continues to be absorbed using the amino acid transporter function. Therefore, the superior outcome of better absorption, bioavailability, and reduced competition with other nucleosides or nucleoside analogs for uptake into the bloodstream is achieved.

In hepatitis C infected chimpanzees, val-mCyd reduced the mean HCV RNA level by 0.83 $\log_{10}$ copies/ml (8.3 mg/kg/day) and 1.05 $\log_{10}$ copies/ml (16.6 mg/kg/day) in seven days. The chimps exhibited no drug-related safety issues.

The parent nucleoside (mCyd) framework can exist as a β-D or β-L nucleoside. In a preferred embodiment, the pharmaceutically acceptable compound is administered in a form that is at least 90% of the β-D enantiomer. In another embodiment, val-mCyd is at least 95% of the β-D enantiomer. The valine ester also has enantiomeric forms. In a preferred embodiment, the valine moiety is at least 90% of the L-enantiomer. In another embodiment, the valine moiety is at least 95% of the L-enantiomer. In alternative embodiments, the compounds are used as racemic mixtures or as any combination of β-D or β-L parent nucleoside and L or D amino acid.

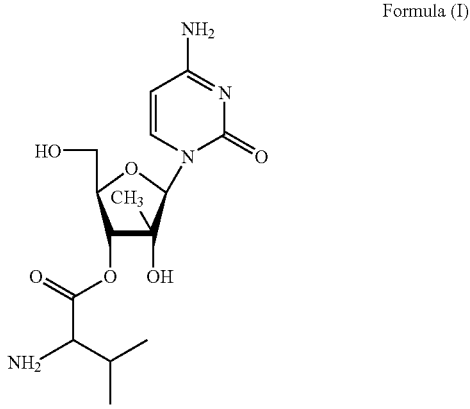

Formula (I)

In one specific embodiment, the compound of Formula (I) is β-D-2'-C-methyl-ribofuranosyl cytidine-3'-O-L-valine ester.HCl salt. In another specific embodiment, the compound of Formula (II), the β-D-2'-C-methyl-ribofuranosyl cytidine dihydrochloride salt, is provided for administration to a host, particularly a human, infected with a flavivirus or pestivirus infection. In other embodiments, tosylate, methanesulfonate, acetate, citrate, malonate, tartarate, succinate, benzoate, ascorbate, α-ketoglutarate, and α-glycerophosphate, formate, fumarate, propionate, glycolate, lactate, pyruvate, oxalate, maleate, salicyate, sulfate, sulfonate, nitrate, bicarbonate, hydrobromate, hydrobromide, hydroiodide, carbonate, and phosphoric acid salts are provided. A particularly preferred embodiment is the mono or dihydrochloride salt.

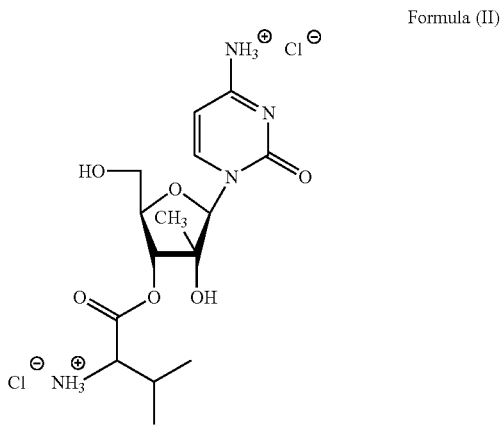

Formula (II)

In another embodiment, a pharmaceutical composition comprising 2'-C-methyl-cytidine-3'-O-L-valine ester or its pharmaceutically acceptable salt, including a mono or di HCl salt, ester, prodrug or derivative thereof together with a pharmaceutically acceptable carrier, excipient or diluent is provided.

In an alternative embodiment, the 5'-hydroxyl group is replaced with a 5'-OR, wherein R is phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipids; an amino acid; a carbohydrate; a peptide; cholesterol; or other pharmaceutically acceptable leaving group which when administered in vivo is capable of providing a compound wherein R is independently H or phosphate.

The active compounds of the present invention can be administered in combination or alternation with another agent that is active against a flavivirus or pestivirus, including HCV (including any described or referred to in the Background of the Invention), or other useful biological agent. Thus another principal embodiment is a pharmaceutical composition that includes β-D-2'-C-methyl-ribofuranosyl cytidine-3'-O-L-valine ester- or a pharmaceutically acceptable salt (including a mono- or di-HCl salt), ester, prodrug or pharmaceutically acceptable derivative thereof, together with one or more other effective antiviral agents, optionally with a pharmaceutically acceptable carrier or diluent. In another embodiment, a method is provided that includes administering β-D-2'-C-methyl-ribofuranosyl cytidine-3'-O-L-valine ester or a salt, ester, prodrug or derivative thereof, in combination or in alternation with one or more second antiviral agents, optionally with a pharmaceutically acceptable carrier or diluent.

Any second antiviral agent may be selected that imparts the desired biological effect. Nonlimiting examples include interferon, ribavirin, an interleukin, an NS3 protease inhibitor, a cysteine protease inhibitor, phenanthrenequinone, a thiazolidine derivative, thiazolidine, benzanilide, a helicase inhibitor, a polymerase inhibitor, a nucleotide analogue, gliotoxin, cerulenin, antisense phosphorothioate oligodeoxynucleotides, inhibitor of IRES-dependent translation, or ribozyme. In one particular embodiment, the second antiviral agent is selected from natural interferon, interferon alpha (including interferon-alpha-2a and interferon-alpha-2b), interferon beta (including interferon beta-1a), omega interferon, interferon gamma (including interferon gamma-1b), interferon tau, and consensus interferon. Any of these interferons can be stabilized or otherwise modified to improve the tolerance and biological stability or other biological properties. One common modification is pegylation (modification with polyethylene glycol). In one particular embodiment, the second antiviral agent is pegylated or unpegylated interferon 2-alpha.

In an alternative embodiment, the active compound is a 3'-amino acid ester of β-D-2'-C-methyl-ribofuranosyl cytidine, wherein the amino acid can be natural or synthetic and can be in a D or L stereoconfiguration. In another embodiment, the active compound is a 3'-acyl ester of β-D-2'-C-methyl-ribofuranosyl cytidine.

BRIEF DESCRIPTION OF THE FIGURES

FIG. 4a is a graph of the effect of β-D-2'-C-methyl-ribofuranosyl cytidine and IntronA on BVDV (strain NY-1) titers in persistently infected MDBK cells over time. FIG. 4b is a graph of the effect of β-D-2'-C-methyl-ribofuranosyl cytidine in combination with IntronA on BVDV (strain I-N-dIns) titers in persistently-infected MDBK cells.

FIG. 5a is a graph of a representative experiment showing the effect over twenty eight days of β-D-2'-C-methyl-ribofuranosyl cytidine or IntronA treatment on BVDV (strain I-N-dIns) titers in persistently infected MDBK cells. FIG. 5b is a photocopy of a dish plated with infected MDBK cells that illustrates the size of the foci formed by phenotypes of the wild-type BVDV (strain I-N-dIns), versus the β-D-2'-C-methyl-ribofuranosyl cytidine-resistant BVDV (I-N-dIns 107R), indicating that the resistant virus formed much smaller foci than the wild-type, I-N-dIns strain. FIG. 5c is a graph of the titer of BVDV strains I-N-dIns or I-N-dIns-107R over hours post-infection in infected MDBK cells. FIG. 5d is a graph of the effect of Intron A on the BVDV viral titer yield in de novo-infected MDBK cells treated with IntronA.

FIG. 9a is a graph showing the relative levels of the di- and tri-phosphate derivatives of β-D-2'-C-methyl-ribofuranosyl cytidine and β-D-2'-C-methyl-ribofuranosyl uridine (mUrd) after incubation of HepG2 cells with 10 μM β-D-2'-C-methyl-ribofuranosyl cytidine over time, as described in Example 14. FIG. 9b is a graph of the decay of the tri-phosphate derivative of β-D-2'-C-methyl-ribofuranosyl cytidine after incubation of HepG2 cells with 10 μM β-D-2'-C-methyl-ribofuranosyl cytidine over time. FIG. 9c is a graph of the concentration of the di- and tri-phosphate derivatives of β-D-2'-C-methyl-ribofuranosyl cytidine and β-D-2'-C-methyl-ribofuranosyl uridine (mUrd) after incubation of HepG2 cells with 10 μM β-D-2'-C-methyl-ribofuranosyl cytidine at increasing concentrations of the drug (μM).

DETAILED DESCRIPTION OF THE INVENTION

Figure 1A:
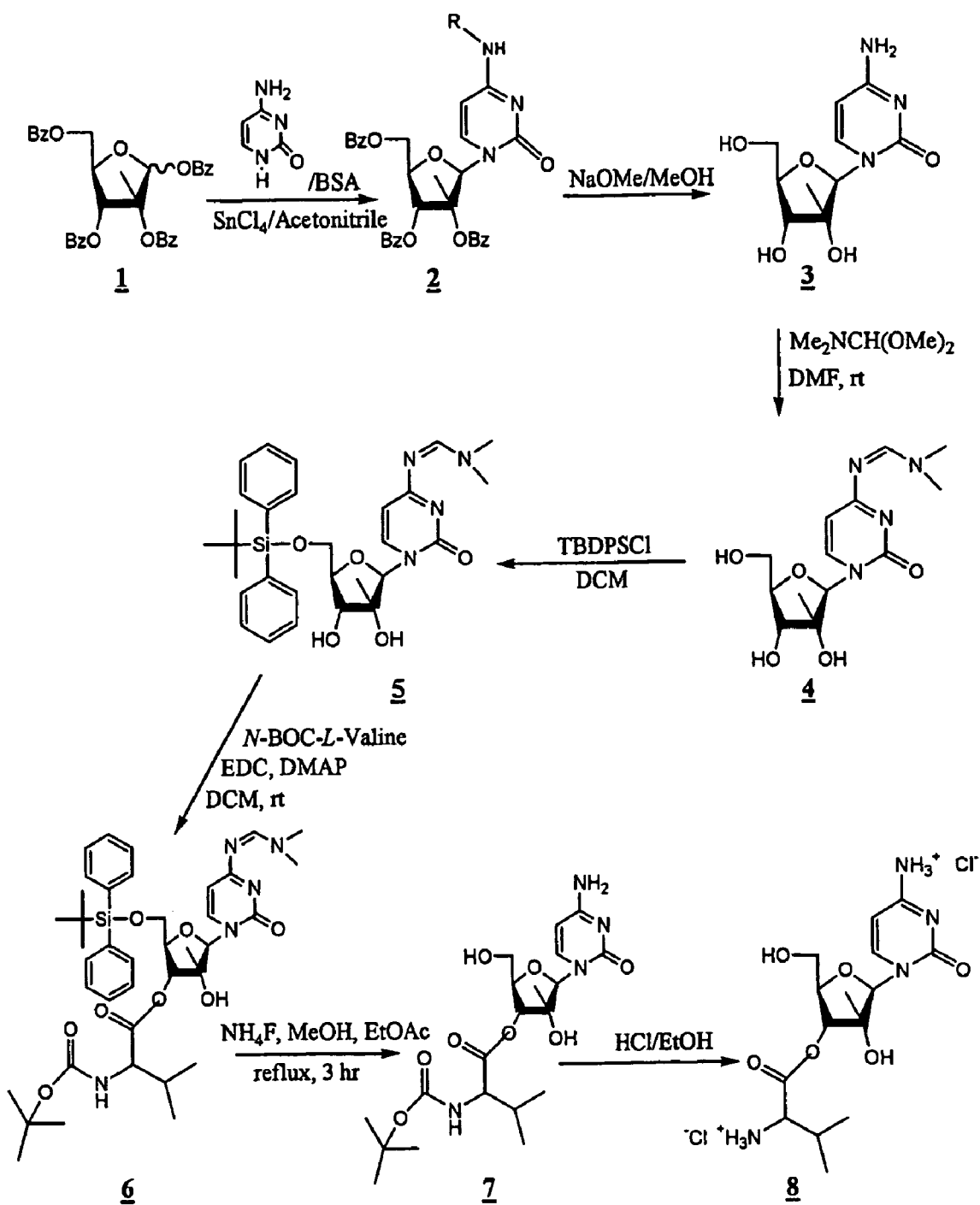
FIGS. 1a and 1b are illustration of two processes for the preparation of β-D-2'-C-methyl-ribofuranosyl cytidine-3'-O-L-valine ester dihydrochloride, as described in Example 1.

It has been discovered that the 3'-L-valine ester of β-D-2'-C-methyl-ribofuranosyl cytidine (referred to alternatively below as val-mCyd) provides superior results against flaviviruses and pestiviruses, including hepatitis C virus. Based on this discovery, compounds, compositions, methods and uses are provided for the treatment of flaviviridae, including HCV, that include the administration of an effective amount of val-mCyd or its salt, ester, prodrug or derivative, optionally in a pharmaceutically acceptable carrier. In an alternative embodiment, val-mCyd is used to treat any virus that replicates through an RNA-dependent RNA polymerase.

The disclosed compounds or their pharmaceutically acceptable derivatives or salts or pharmaceutically acceptable formulations containing these compounds are useful in the prevention and treatment of flaviviridae (including HCV) infections and other related conditions such as anti-HCV antibody positive and HCV-positive conditions, and hepatitis C related hepatic cancer (e.g., hepatocellular carcinoma) and hepatic tumors. In addition, these compounds or formulations can be used prophylactically to prevent or retard the progression of clinical illness in individuals who are anti-HCV (or more generally anti-flaviviridae) antibody or HCV-antigen or flaviviridae-antigen positive, or who have been exposed to HCV or another flaviviridae virus.

In summary, the present invention includes the following features:

(a) 3'-L-valine ester of β-D-2-C-methyl-ribofuranosyl cytidine, and pharmaceutically acceptable prodrugs, derivatives and salts thereof, including specifically the mono- and di-hydrochloride salts;

(b) 3'-L-valine ester of β-D-2'-C-methyl-ribofuranosyl cytidine, and pharmaceutically acceptable prodrugs, derivatives and salts thereof for use in medical therapy, for example for the treatment or prophylaxis of an flaviridae (including HCV) infection;

(c) use of the 3'-L-valine ester of β-D-2'-C-methyl-ribofuranosyl cytidine, and pharmaceutically acceptable prodrugs, derivatives and salts thereof in the manufacture of a medicament for treatment of a flaviviridae (including HCV) infection;

(d) pharmaceutical formulations comprising the 3'-L-valine ester of β-D-2'-C-methyl-ribofuranosyl cytidine, and pharmaceutically acceptable prodrugs, derivatives and salts thereof together with a pharmaceutically acceptable carrier or diluent;

(e) processes for the preparation of the 3'-L-valine ester of β-D-2'-C-methyl-ribofuranosyl cytidine;

(f) use of the 3'-L-valine ester of β-D-2'-C-methyl-ribofuranosyl in the treatment of infections caused by viruses that replicate through an RNA dependent RNA polymerase; and (g) use of the 3'-L-valine ester of β-D-2'-C-methyl-ribofuranosyl in the treatment of viral infections by administration in combination or alternation with another antiviral agent.

In an alternative embodiment, the active compound is a 3'-amino acid ester of β-D-2'-C-methyl-ribofuranosyl cytidine, wherein the amino acid can be natural or synthetic and can be in a D or L stereoconfiguration. In another embodiment, the active compound is a 3'-acyl ester of β-D or β-L 2'-C-methyl-ribofuranosyl cytidine. The compounds of this invention either possess antiviral activity, or are metabolized to a compound that exhibits such activity.

Although not to be bound by theory, in vitro mechanism-of-action studies suggest that mCyd is a specific inhibitor of genomic RNA replication. Moreover, the intracellular 5'-triphosphate moiety, mCyd-TP, appears to directly inhibit the NS5B RNA-dependent-RNA polymerase. Analysis of RNA synthesis in the presence of mCyd-TP suggests that mCyd-TP acts as a specific chain terminator of viral RNA synthesis through as yet unidentified mechanisms. Antiviral nucleosides and nucleoside analogs are generally converted into the active metabolite, the 5'-triphosphate (TP) derivatives by intracellular kinases. The nucleoside-TPs then exert their antiviral effect by inhibiting the viral polymerase during virus replication. In cultured cells, intracellular phosphorylation converts mCyd predominantly into the active species, mCyd-triphosphate (mCyd-TP), along with low levels of mCyd-diphosphate. Additionally, a second TP product, 2'-C-methyl-uridine TP (mUrd-TP), is found and is thought to arise via intracellular deamination of mCyd or mCyd-5'-phosphate species.

Flaviviruses included within the scope of this invention are discussed generally in *Fields Virology*, Editors: Fields, N., Knipe, D. M. and Howley, P. M.; Lippincott-Raven Pulishers, Philadelphia, Pa.; Chapter 31 (1996). Specific flaviviruses include, without limitation: Absettarov; Alfiy; Apoi; Aroa; Bagaza; Banzi; Bououi; Bussuquara; Cacipacore; Carey Island; Dakar bat; Dengue viruses 1, 2, 3 and 4; Edge Hill; Entebbe bat; Gadgets Gully; Hanzalova; Hypr; Ilheus; Israel turkey meningoencephalitis; Japanese encephalitis; Jugra; Jutiapa; Kadam; Karshi; Kedougou; Kokoera; Koutango; Kumlinge; Kunjin; Kyasanur Forest disease; Langat; Louping ill; Meaban; Modoc; Montana myotis leukoencephalitis; Murray valley encephalitis; Naranjal; Negishi; Ntaya; Omsk hemorrhagic fever; Phnom-Penh bat; Powassan; Rio Bravo; Rocio; Royal Farm; Russian spring-summer encephalitis; Saboya; St. Louis encephalitis; Sal Vieja; San Perlita; Saumarez Reef; Sepik; Sokuluk; Spondweni; Stratford; Temusu; Tyuleniy; Uganda S, Usutu, Wesselsbron; West Nile; Yaounde; Yellow fever; and Zika.

Pestiviruses included within the scope of this invention are also discussed generally in *Fields Virology* (Id.). Specific pestiviruses include, without limitation: bovine viral diarrhea virus ("VDV"); classical swine fever virus ("CSFV") also known as hog cholera virus); and border disease virus ("DV").

DEFINITIONS

The term alkyl, as used herein, unless otherwise specified, refers to a saturated straight, branched, or cyclic, primary, secondary, or tertiary hydrocarbon of typically $C_1$ to $C_{10}$, and specifically includes $CF_3$, $CCl_3$, $CFCl_2$, $CF_2Cl$, $CH_2CF_3$, $CF_2CF_3$, methyl, ethyl, propyl, isopropyl, cyclopropyl, butyl, isobutyl, secbutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups, and particularly includes halogenated alkyl groups, and even more particularly fluorinated alkyl groups. Non-limiting examples of moieties with which the alkyl group can be substituted are selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al.,

*Protective Groups in Organic Synthesis*, John Wiley and Sons, Second Edition, 1991, hereby incorporated by reference.

The term lower alkyl, as used herein, and unless otherwise specified, refers to a $C_1$ to $C_4$ saturated straight, branched, or a cyclic (for example, cyclopropyl)alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term alkylamino or arylamino refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term aryl, as used herein, and unless otherwise specified, refers to phenyl, biphenyl, or naphthyl, and preferably phenyl. The term includes both substituted and unsubstituted moieties. The aryl group can be substituted with any desired moiety, including, but not limited to, one or more moieties selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term alkaryl or alkylaryl refers to an alkyl group with an aryl substituent. The term aralkyl or arylalkyl refers to an aryl group with an alkyl substituent.

The term halo, as used herein, includes a specific description of chloro, bromo, iodo, and fluoro individually.

The term purine or pyrimidine base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-alkylaminopurine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, 5-iodo-pyrimidine, 6-iodo-pyrimidine, 2-Br-vinyl-5-pyrimidine, 2-Br-vinyl-6-pyrimidine, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-amino-pyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term acyl or O-linked ester refers to a group of the formula C(O)R', wherein R' is an straight, branched, or cyclic alkyl (including lower alkyl), carboxylate residue of an amino acid, aryl including phenyl, heteroaryl, alkaryl, aralkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxy-trityl, substituted benzyl, alkaryl, aralkyl including benzyl, alkoxyalkyl including methoxymethyl, aryloxyalkyl such as phenoxymethyl. Aryl groups in the esters optimally comprise a phenyl group. In nonlimiting embodiments, acyl groups include acetyl, trifluoroacetyl, methylacetyl, cyclopropylacetyl, cyclopropyl-carboxy, propionyl, butyryl, isobutyryl, hexanoyl, heptanoyloctanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoro-heptanoyl, 7H-dodeca-fluoroheptanoyl, 7-chlorododecafluoro-heptanoyl, 7-chloro-dodecafluoro-heptanoyl, 7H-dodecafluoro-heptanoyl, 7H-dodeca-fluoroheptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxy-benzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl.

The term amino acid includes naturally occurring and synthetic α, β, γ, or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration, but can also be used in the D-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl.

As used herein, the term "substantially free of" or "substantially in the absence of" refers to a nucleoside composition that includes at least 85 or 90% by weight, preferably 95%, 98, 99% or 100% by weight, of the designated enantiomer of that nucleoside.

Similarly, the term "isolated" refers to a nucleoside composition that includes at least 85 or 90% by weight, preferably 95%, 98%, 99% or 100% by weight, of the nucleoside.

The term host, as used herein, refers to an unicellular or multicellular organism in which the virus can replicate, including cell lines and animals, and preferably a human. Alternatively, the host can be carrying a part of the Flaviviridae viral genome, whose replication or function can be altered by the compounds of the present invention. The term host specifically refers to infected cells, cells transfected with all or part of the Flaviviridae genome and animals, in particular, primates (including chimpanzees) and humans. In most animal applications of the present invention, the host is a human patient. Veterinary applications, in certain indications, however, are clearly anticipated by the present invention (such as chimpanzees).

The term "pharmaceutically acceptable salt or prodrug" is used throughout the specification to describe any pharmaceutically acceptable form (such as an ester, phosphate ester, salt of an ester or a related group) of a nucleoside compound which, upon administration to a patient, provides the nucleoside compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess antiviral activity against a Flaviviridae, or are metabolized to a compound that exhibits such activity.

I. Active Compounds, Physiologically Acceptable Salts and Prodrugs Thereof

Methods and compositions for the treatment of pestivirus, flavivirus and hepatitis C virus infection are described that include administering an effective amount of 2-C-methyl-cytidine-3'-O-L-valine, or a pharmaceutically acceptable salt, ester or prodrug thereof to a host in need thereof.

In one embodiment, a hydrochloride salt of the compound of Formula (I) is used. In another embodiment, a dihydrochloride salt of the compound of Formula (I) is preferred. However, the active compound can be administered as any salt or prodrug that upon administration to the recipient is capable of providing directly or indirectly the parent compound, or that exhibits activity itself. Nonlimiting examples are the pharmaceutically acceptable salts, which are alternatively referred to as "physiologically acceptable salts", and a compound that has been alkylated, acylated or otherwise modified at the 5'-position or on the purine or pyrimidine base, thereby forming a type of "pharmaceutically acceptable prodrug". Further, the modifications can affect the biological activity of the compound, in some cases increasing the activity over the parent compound. This can easily be assessed by preparing the salt or prodrug and testing its antiviral activity according to the methods described herein, or other methods known to those skilled in the art.

In a first principal embodiment a compound of the Formula (I), or a pharmaceutically acceptable salt or prodrug thereof, is provided:

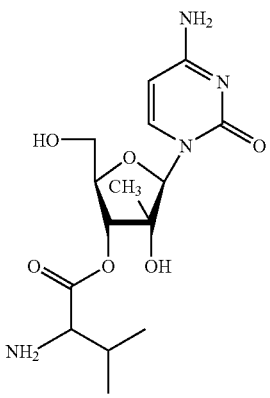

Formula (I)

It is to be understood that all stereoisomeric, tautomeric and polymorphic forms of the compounds are included herein. The 2'-methyl substitution also may be other alkyl groups such as ethyl, propyl, or, alternatively, ethenyl.

In an alternative embodiment, the active compound is a 3'-amino acid ester of β-D-2'-C-methyl-ribofuranosyl cytidine, wherein the amino acid can be natural or synthetic and can be in a D or L stereoconfiguration. In another embodiment, the active compound is a 3'-acyl ester of β-D-2'-C-methyl-ribofuranosyl cytidine.

In another alternative embodiment, the 5'-hydroxyl group is replaced with a 5'-OR, wherein R is phosphate (including monophosphate, diphosphate, triphosphate, or a stabilized phosphate prodrug); a stabilized phosphate prodrugi acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipids; an amino acid; a carbohydrate; a peptide; cholesterol; or other pharmaceutically acceptable leaving group which when administered in vivo is capable of providing a compound wherein R is independently H or phosphate.

II. Synthesis of Active Compounds

The compound of the present invention can be synthesized by means known in the art. For example, in one embodiment, a nucleoside, nucleoside analog, or a salt, prodrug, stereoisomer or tautomer thereof, that is disubstituted at the 2° C. is prepared. In another embodiment, β-D-2'-C-methyl-cytidine (4-amino-1-(3,4-dihydroxy-5-hydroxymethyl-3-C-methyl-tetrahydro-furan-2-yl)-1H-pyrimidine-2-one), which has value as an active nucleoside or is used as a process intermediate is prepared. In yet another embodiment, 3'-O-valinyl ester of β-D-2'-C-methyl-cytidine (2-amino-3-methyl-butyric acid 5-(4-amino-2-oxo-2H-pyrimidin-1-yl)-4-hydroxy-4-C-methyl-2-hydroxymethyl-tetrahydro-furan-3-yl ester) or a hydrochloride salt form is prepared. Nucleosides, nucleoside analogs, salts or ester prodrugs prepared may be used as intermediates in the preparation of a wide variety of other nucleoside analogues, or may be used directly as antiviral and/or antineoplastic agents.

EXAMPLE 1

Synthesis of β-D-2'-C-methyl-ribofuranosyl cytidine-3'-O-L-valine ester

In one synthesis method, depicted in FIG. 1a, the synthesis comprises reacting cytosine, BSA and SnCl$_4$/acetonitrile with 1,2,3,5-tetra-O-benzoyl-2-C-methyl-β-D-ribofuranose (1) to form 4-amino-1-(3,4-dibenzoyloxy-5-benzoyloxymethyl-3-methyl-tetrahydro-furan-2-yl)-1H-pyrimidin-2-one (2; and reacting (2) with NaOMe/MeOH to provide 4-amino-1 (3,4-dihydroxy-5-hydroxymethyl-3-methyl-tetrahydro-furan-2-yl)-1H-pyrimidin-2-one (3), also known as 2-C-methyl-β-D-ribofuranose. The use of cytosine as a starting material rather than benzoyl-cytosine improves the "atom economy" of the process and simplifies purification at later steps.

The next steps in this process comprise reacting (3) with Me$_2$NCH(OMe)$_2$ in DMF to form (4), N-[1-(3,4-dihydroxy-5-hydroxymethyl-3-methyl-tetrahydro-furan-2-yl)-2-oxo-1,2-dihydro-pyrimidin-4-yl]-N,N-dimethyl-formamidine, which is the amino-protected form of (3); reacting (4) with TBDPSCl and imidazole in DCM to provide the 5'-silyl-protected form of (4) as N'-{1-[5-(tert-butyl-diphenyl-silanyloxymethyl)-3,4-dihydroxy-3-methyl-tetrahydro-furan-2-yl]-2-oxo-1,2-dihydro-pyrimidin-4-yl}-N,N-dimethyl-formamidine (5), where the use of DCM provides the advantage of having greater control over disilyl by-product formation; reacting (5) with N-Boc-L-valine, EDC and DMAP in DCM at room temperature to form 2-tert-butoxy-carbonylamino-3-methyl-butyric acid 2-(tert-butyl-diphenyl-silanyloxy-methyl)-5-[4-(dimethylamino-methyleneamino)-2-oxo-2H-pyrimidin-1-yl]-4-hydroxy-4-methyl-tetrahydro-furan-3-yl ester (6); removing the silyl and amino-protecting groups by reacting (6) with NH$_4$F in MeOH in the presence of approximately 10 mole equivalents of ethyl acetate to prevent cleavage of the 3'-O-valinyl ester by liberated ammonia, and refluxing the mixture to provide 2-tert-butoxycarbonylamino-3-methyl-butyric acid 5-(4-amino-2-oxo-2H-pyrimidin-1-yl)-4-hydroxy-2-hydroxymethyl-4-methyl-tetrahydro-furan-3-yl ester to provide (7); and finally, reacting (7) with HCl in EtOH to provide 2-amino-3-methyl-butyric acid 5-(4-amino-2-oxo-2H-pyrimidin-1-yl)-4-hydroxy-2-hydroxymethyl-4-methyl-tetrahydro-furan-3-yl ester, dihydrochloride salt (8) as a final product.

Alternative Synthesis

Figure 1B:
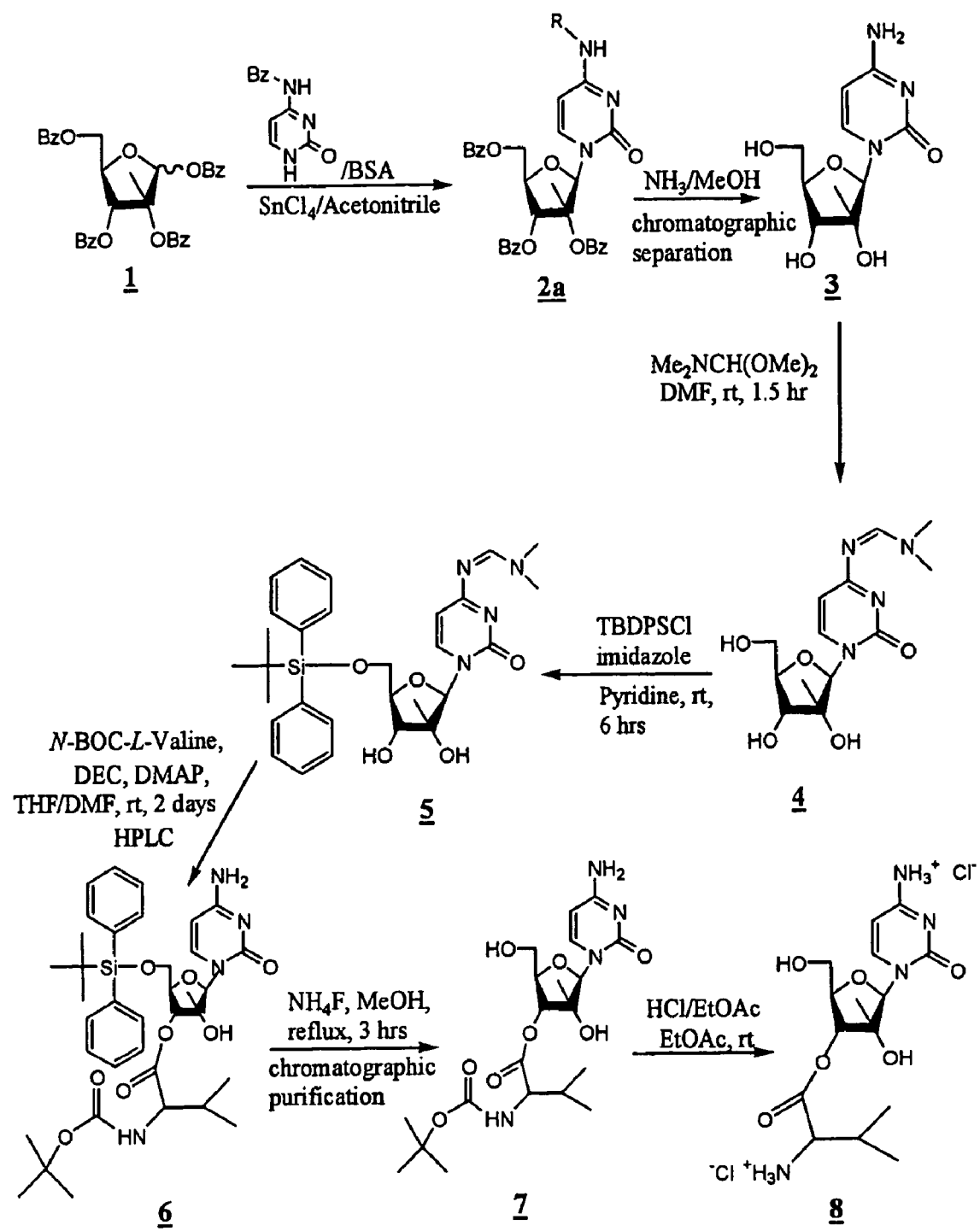

In another method to synthesize the compounds of the invention, shown in FIG. 1b, benzoylcytosine, BSA and SnCl$_4$/acetonitrile are reacted with 1,2,3,5-tetra-O-benzoyl-2-C-methyl-β-D-ribofuranose (1) to form 4-benzoylamino-1-(3,4-dibenzoyloxy-5-benzoyloxymethyl-3-methyl-tetrahydro-furan-2-yl)-1H-pyrimidin-2-one (2a); reacting (2a) with NH$_3$ in methanol and chromatographically separating the product, 4-amino-1-(3,4-dihydroxy-5-hydroxymethyl-3-methyl-tetrahydro-furan-2-yl)-1H-pyrimidin-2-one (3), also known as β-D-2'-C-methyl-cytidine; reacting (3) with Me$_2$NCH(OMe)$_2$ in DMF at room temperature for 1.5 hours to form N-[1-(3,4-dihydroxy-5-hydroxymethyl-3-methyl-tetrahydro-furan-2-yl)-2-oxo-1,2-dihydro-pyrimidin-4-yl]-N,N-dimethyl-formamidine (4); reacting (4) with TBDPSCl and pyridine at room temperature for 6 hours to provide N'-{1-[5-(tert-butyl-diphenyl-silanyloxymethyl)-3,4-dihydroxy-3-methyl-tetrahydro-furan-2-yl]-2-oxo-1,2-dihydro-pyrimidin-4-yl}-N,N-dimethyl-formamidine (5); reacting (5) with N-Boc-L-valine, DEC and DMAP in THF/DMF at room temperature for 2 days and subjecting the product formed from this reaction to HPLC in order to provide 2-tert-butoxycarbonylamino-3-methyl-butyric acid 2-(tert-butyl-diphenyl-silanyloxy-methyl)-5-[4-dimethylaminomethyl-eneamino)-2-oxo-2H-pyrimidin-1-yl]-4-hydroxy-4-methyl-tetrahydro-furan-3-yl ester (6); refluxing (6) with NH$_4$F in MeOH for about 3 hours to remove the silyl and amino-protecting groups, and subjecting the product to chromatographic purification to provide 2-tert-butoxycarbonylamino-3-methyl-butyric acid 5-(4-amino-2-oxo-2H-pyrimidin-1-yl)-4-hydroxy-2-hydroxymethyl-4-methyl-tetrahydro-furan-3-yl ester (7); and finally reacting (7) with HCl in EtOAc at room temperature to provide 2-amino-3-methyl-butyric acid 5-(4-amino-2-oxo-2H-pyrimidin-1-yl)-4-hydroxy-2-hydroxymethyl-4-methyl-tetrahydro-furan-3-yl ester, dihydrochloride salt (8) as a final product.

EXAMPLE 2

Synthesis of 2'-C-methyl-cytidine-3'-O-L-valine ester (val-mCyd)

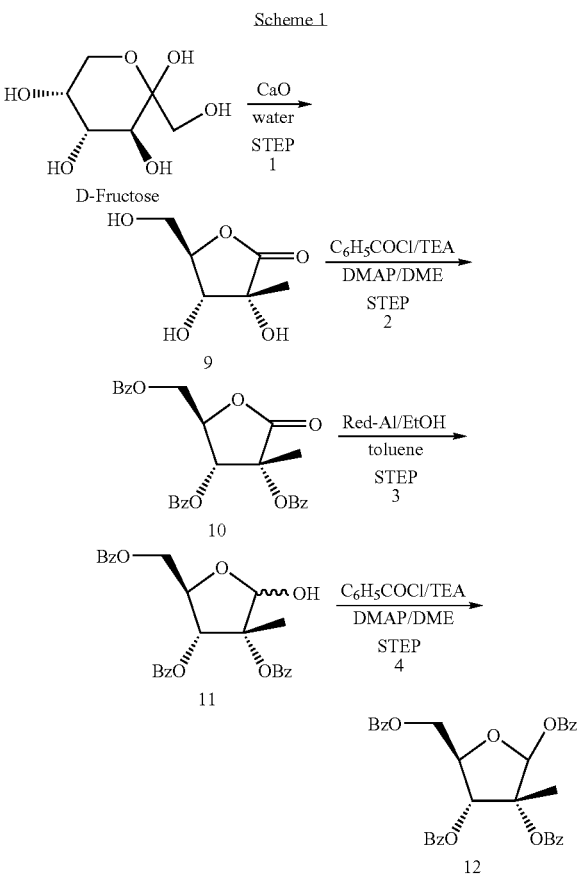

Step 1: Synthesis of Compound 9

2-C-Methyl-D-ribonic-γ-lactone

De-ionized water (100 mL) was stirred in a 250 mL 3-necked round bottom flask, equipped with an overhead stirrer, a stirring shaft, a digital temperature read-out device and an argon line. Argon was bubbled into water for thirty minutes and D-fructose (20.0 g, 0.111 mole) was added and the solution became clear in a few minutes. Calcium oxide (12.5 g, 0.223 mole) was added in portions over a period of five minutes and the mixture was vigorously stirred. An exotherm was observed and reaction temperature reached 39.6° C. after 10 minutes from the start of the calcium oxide addition. After about fifteen minutes, the reaction mixture developed a yellow color that deepened with time. After three hours, an aliquot was withdrawn for TLC analysis. The aliquot was acidified to pH 2 using saturated aqueous solution of oxalic acid. The resulting white suspension was evaporated under reduced pressure to remove the water. Toluene (2 mL) was added to the residue and the mixture was evaporated under reduced pressure (at 45-50° C.) to remove any trace of water. The residual solid was reconstituted in 2 mL of 1:1 tetrahydrofluran:methanol mixture. After thorough mixing, the suspension was allowed to settle and the supernatant clear solution was spotted for TLC (silica plate was developed in 2% methanol in ethyl acetate and stained in 1% alkaline potassium permanganate dip. The plate was then heated, using a heat gun, until the appearance of yellowish spots on the pink background). The desired lactone typically appears at an $R_f$ value of 0.33 under the above conditions. More polar by-products and unreacted material are detected in the $R_f$ value range of 0.0 to 0.2.

Although product formation was observed after 3 hours, the reaction was allowed to continue for 22 hours during which time the reaction mixture was stirred at 25° C. At the end of this period, pH of the mixture was 13.06. Carbon dioxide gas was bubbled into the reaction mixture for about 2.5 hours (pH was 7.25). The formed calcium carbonate solid was removed by vacuum filtration, filter cake washed with 50 mL of de-ionized water. The aqueous layers were combined and treated with oxalic acid (5.0 g, 0.056 mole) and the mixture was vigorously stirred at 25° C. for 30 minutes (The initial dark color largely disappeared and the mixture turned into a milky white slurry). The pH of the mixture at this stage is typically 2-3. The slurry mixture was stirred at 45-50° C. overnight. The mixture was then evaporated under reduced pressure and at 45-50° C. to remove 75 mL of water. Sodium chloride (30 g) and tetrahydrofuran (100 mL) were added to the aqueous slurry (about 75 mL) and the mixture was vigorously stirred at 25° C. for 30 minutes. The layers were separated and the aqueous layer was stirred for 10 minutes with 75 mL of fresh tetrahydrofuran. This process was repeated for three times and the tetrahydrofuran solutions were combined and stirred with 10 g of anhydrous magnesium sulfate for 30 minutes. The mixture was filtered and the magnesium sulfate filter cake was washed with 60 mL of tetrahydrofuran. The filtrate was evaporated under reduced pressure and at 40° C. to give 10.86 g of crude product as a dark orange semisolid. (For scale up runs tetrahydrofuran will be replaced with acetone instead of evaporation of crude product to dryness). Crude product was stirred with acetone (20 mL) at 20° C. for 3 hours. Product was collected by vacuum filtration and the filter cake washed with 12 mL of acetone to give the desired product 9 as white crystalline solid. Product was dried in vacuum to give 2.45 g (13.6% yield). Melting point of compound 9: 158-162° C. (literature melting point: 160-161° C.). $^1$H NMR (DMSO-$d_6$) δ ppm 5.69 (s, 1H, exch. With $D_2O$), 5.41 (d, 1H, exch. With $D_2O$), 5.00 (t, 1H, exch. With $D_2O$), 4.15 (m, 1H), 3.73 (m, 2H), 3.52 (m, 1H), 1.22 (s, 3H). $^{13}$C NMR (DMSO-$d_6$) δ ppm 176.44, 82.95, 72.17, 72.02, 59.63, 20.95. ($C_6H_{10}O_5$: calcd C, 44.45; H, 6.22. Found: C, 44.34; H, 6.30).

Step 2: Synthesis of Compound 10

2,3,5-Tri-O-benzoyl-2-C-methyl-D-ribonic-γ-lactone

A mixture of lactone 1 (3.0 g, 18.50 mmol.), 4-dimethylaminopyridine (0.45 g, 3.72 mmol.) and triethylamine (25.27 g, 249.72 mmol.) in 1,2-dimethoxy ethane (50 mL) was stirred at 25° C. under argon atmosphere for thirty minutes. This white suspension was cooled to 5° C. and benzoyl chloride (11.7 g, 83.23 mmol.) was added over a period of fifteen minutes. The mixture was stirred at 25° C. for two hours. TLC analysis (silica, 2% methanol in ethyl acetate) indicated complete consumption of starting material. Ice cold water (100 g) was added to the reaction mixture and stirring was continued for thirty minutes. The formed white solids were collected by vacuum filtration and filter cake washed with cold water (50 mL). This crude product was stirred with tert-butyl methyl ether (60 mL) at 20° C. for thirty minutes, then filtered, filter cake washed with tert-butyl methyl ether (25 mL) and dried in vacuum to give 7.33 g (83.4% yield) of compound 10 as a white solid in 97.74% purity (HPLC/AUC). Melting point of compound 10: 137-140° C. (literature melting point: 141-142° C.). $^1$H NMR (CDCl$_3$) δ ppm 8.04 (d, 2H), 7.92 (d, 2H), 7.73 (d, 2H), 7.59 (t, 1H), 7.45 (m, 4H), 7.32 (t, 2H), 7.17 (t, 2H), 5.51 (d, 1H), 5.17 (m, 1H), 4.82-4.66 (d of an AB quartet, 2H) 1.95, (s, 3H). $^{13}$C NMR (CDCl$_3$) δ ppm 172.87, 166.17, 166.08, 165.58, 134.06, 133.91, 133.72, 130.09, 129.85, 129.80, 129.37, 128.78, 128.60, 128.49, 127.96, 127.89, 79.67, 75.49, 72.60, 63.29, 23.80. TOF MS ES+ (M+1: 475).

Step 3: Synthesis of Compound 11

2,3,5-Tri-O-benzoyl-2-C-methyl-β-D-ribofuranose

A solution of Red-Al (65 wt. % in toluene, 2.0 mL, 6.56 mmol.) in anhydrous toluene (2.0 mL) was stirred at 0° C. under argon atmosphere. A solution of anhydrous ethanol (0.38 mL, 6.56 mmol.) in anhydrous toluene (1.6 mL) was added to the toluene solution over a period of five minutes. The resulting mixture was stirred at 0° C. for fifteen minutes and 2 mL (2.18 mmol.) of this Red-Al/ethanol reagent was added to a cold (−5° C.) solution of 2,3,5-tri-O-benzoyl-2-C-methyl-D-ribonolactone 2 (475 mg, 1.0 mmol.) in anhydrous toluene (10 mL) over a period of 10 minutes. The reaction mixture was stirred at −5° C. for forty minutes. TLC analysis (silica plates, 35% ethyl acetate in heptane) indicated complete consumption of starting material. HPLC analysis indicated only 0.1% of starting material remaining. The reaction was quenched with acetone (0.2 mL), water (15 mL) and 1 N HCl (15 mL) at 0° C. and allowed to warm to room temperature. 1 N HCl (5 mL) was added to dissolve the inorganic salts (pH: 2-3). The mixture was extracted with ethyl acetate (3×25 mL) and the organic solution washed with brine (25 mL), dried (anhydrous sodium sulfate, 10 g) and solvent removed under reduced pressure and at temperature of 40° C. to give the desired product 11 in quantitative yield (480 mg). This material was used as is for the subsequent step.

Step 4: Synthesis of Compound 12

1,2,3,5-tetra-O-benzoyl-2-C-methyl-β-D-ribofuranose

Benzoyl chloride (283 mg, 2.0 mmol.) was added, over a period of five minutes, to a cold solution (5° C.) of compound II (480 mg, 1.0 mmol.), 4-dimethylaminopyridine (12.3 mg, 0.1 mmol.) and triethylamine (506 mg, 5.0 mmol.) in anhydrous tetrahydrofuran (5 mL). The reaction mixture was stirred at room temperature and under argon atmosphere overnight. HPLC analysis indicated 0.25% of un-reacted starting material. The reaction was quenched by adding ice-cold water (10 g) and saturated aqueous solution of sodium bicarbonate. Tetrahydrofuran was removed under reduced pressure and the mixture was extracted with ethyl acetate (50 mL). The organic solution was washed with water (25 mL), brine (25 mL), dried (anhydrous sodium sulfate, 12 g) and solvent removed under reduced pressure to give 650 mg of thick oily product. This crude product was stirred with 5 mL of tert-butyl methyl ether for 5 minutes and heptane (5 mL) and water (0.1 mL) were added and stirring was continued for an additional period of two hours at 20° C. Solids were collected by vacuum filtration and filter caked washed with 1:1 heptane:tert-butyl methyl ether solution (6 mL) and tert-butyl methyl ether (2 mL). Drying the solid in vacuum gave 300 mg (52%) of desired product 12 (98.43% pure by HPLC/AUC) as a white solid that melted at 154-156.3° C. (literature melting point: 155-156° C.). $^1$H NMR (CDCl$_3$) δ ppm 8.13 (m, 4H), 8.07 (d, 2H), 7.89 (d, 2H), 7.63 (m, 3H), 7.48 (m, 6H), 7.15 (m, 3H), 7.06 (s, 1H), 5.86 (dd, 1H), 4.79 (m, 1H), 4.70-4.52 (d of an AB quartet, 2H), 1.95, (s, 3H). $^{13}$C NMR (CDCl$_3$) δ ppm 166.31, 165.83, 165.01, 164.77, 134.01, 133.86, 133.70, 133.17, 130.44, 130.13, 129.97, 129.81, 129.59, 129.39, 129.07, 128.84, 128.76, 128.37, 98.01, 86.87, 78.77, 76.35, 64.05, 17.07. (C$_{34}$H$_{28}$O$_9$: calcd C, 70.34; H, 4.86. Found: C, 70.20; H, 4.95).

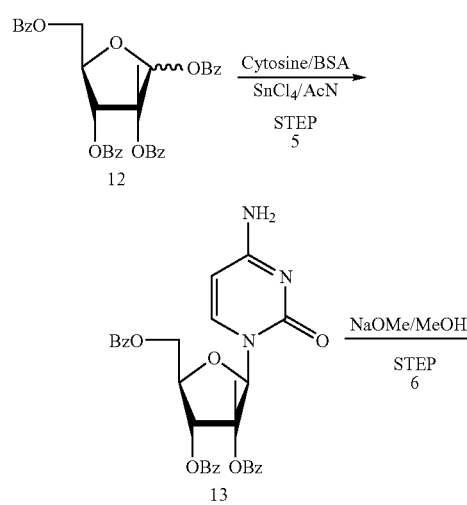

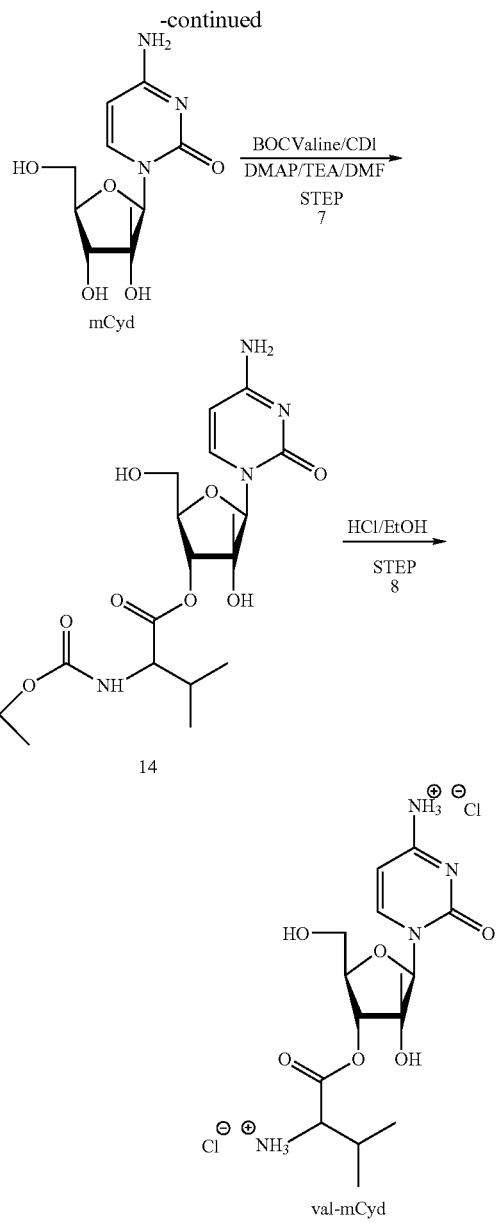

Step 5: Synthesis of Compound 13

4-Amino-1-(3,4-dibenzoyloxy-5-benzyloxymethyl-3-methyl-tetrahydro-furan-2-yl)-1H-pyrimidine-2-one Cytosine (89 g, 0.80 mol) was suspended in acetonitrile (900 ml) in a 12 L round bottomed flask equipped with a reflux condenser, overhead stirrer and an argon inlet adapter. The suspension was stirred at 20° C. under argon atmosphere and N,O-bis(trimethylsilyl)acetamide (537 ml, 2.2 mol) was added in one portion. The resulting solution was heated to 80° C. and stirred for an additional hour at the same temperature. 1,2,3,5-tetra-O-benzoyl-2-C-methyl-β-D-ribofuranose (425.0 g, 0.73 mol) was suspended in acetonitrile (4000 ml) and added to the reaction mixture. The reaction mixture became clear after a few minutes and the temperature dropped to ca. 50° C. Tin(IV) chloride (154 ml, 1.31 mol) was added over a period of 15 minutes and stirring was continued at 80°. After one hour, an aliquot of reaction mixture was quenched by adding aqueous sodium bicarbonate solution and extracting the aqueous layer with ethyl acetate. The ethyl acetate layer was examined by TLC (silica gel, 20% ethyl acetate in heptane, $R_f$ for sugar derivative: 0.40). TLC analysis indicated the complete consumption of the sugar derivative. Desired product was detected by TLC using 10% methanol in dichloromethane ($R_f$: 0.37). The reaction was also monitored by HPLC (Method # 2). Reaction mixture was cooled to 20° C. and quenched by adding saturated aqueous sodium bicarbonate solution (3000 ml) over a period of 30 minutes (observed an exotherm when added the first few drops of the sodium bicarbonate solution). Solid sodium bicarbonate (1350 g) was added in portions to avoid foaming. The mixture was checked to make sure that its pH is $\geq 7$. Agitation was stopped and layers were allowed to separate for 20 minutes. The aqueous layer was drained and stirred with ethyl acetate (1500 ml) and the mixture was allowed to separate (30 minutes). The organic layer was isolated and combined with the acetonitrile solution. The organic solution was washed with brine (500 ml) and then solvent stripped to a volume of ca. 750 ml. Product can be used as is in the subsequent reaction. It may also be further stripped to white foamy solid, in quantitative yield. Structure of compound 10 was confirmed by $^1$H NMR analysis.

Step 6: Synthesis of Compound mCyd

4-Amino-1-(3,4-dihydroxy-5-hydroxymethyl-3-methyl-tetrahydro-furan-2-yl)-1H-pyrimidine-2-one Sodium methoxide (13.8 g, 0.26 mol) was added to a solution of compound 10 (416 g, 0.73 mol) in methanol (2000 ml). The reaction mixture was stirred at room temperature and monitored by TLC (silica gel, 10% methanol in dichloromethane, $R_f$ of compound 9: 0.53) and (silica gel, 30% methanol in dichloromethane, $R_f$ of compound 11: 0.21). Product started to precipitate after 30 minutes and TLC indicated reaction completion after two hours. The reaction was also monitored by HPLC (Method # 2). Methanol was removed under reduced pressure to a volume of ca. 500 ml chased with ethanol (2×500 ml) to a volume of ca. 500 ml. The residual thick slurry was diluted with 750 ml of ethanol and the mixture was stirred at 20° C. for one hour. Product was collected by filtration, filter cake washed with ethanol (100 ml) and tert-butyl-methyl ether (100 ml) and dried to give 168 g (90% yield for the two steps) of product 11 in purity of >97% (HPLC/AUC). Product was also analyzed by $^1$H and $^{13}$C NMR.

Step 7: Synthesis of Compound 14

2-Tert-butoxycarbonylamino-3-methyl-butyric acid 5-(4-amino-2-oxo-2H-pyrimidin-1-yl-4-hydroxy-2-hydroxymethyl-4-methyl-tetrahydro-furan-3-yl ester A solution of N-(tert-butoxycarbonyl)-L-valine (46.50 g, 214 mmol.), carbonyldiimidazole (34.70 g, 214 mmol.), and anhydrous tetrahydrofuran (1000 mL) in a 2 L round bottom flask, was stirred at 25° C. under argon for 1.5 hours and then at 40-50° C. for 20 minutes. In a separate 5 L 5-necked round bottom flask, equipped with an overhead stirrer, cooling tower, temperature probe, addition funnel, and an argon line was added 4-amino-1-(3,4-dihydroxy-5-hydroxymethyl-3-methyl-tetrahydro-furan-2-yl)-1H-pyrimidine-2-one (50.0 g, 195 mmol.) and anhydrous N,N-dimethylformamide (1000 mL). This mixture was heated at 100° C. for 20 minutes until all of the pyrimidine-2-one derivative compound went into solution, and then triethyl amine (500 mL) and 4-dimethylaminopyridine (2.38 g, 19 mmol) were added to the solution. The mixture was next heated at 97° C. for 20 minutes and the tetrahydrofuran solution was added slowly through an addition funnel over a period of 2 hours, maintaining the temperature no lower than 82° C. The reaction mixture was heated at 82° C. for 1 hour and monitored by HPLC (product=68%, SM=11%, and impurity at about 12 min=17%, excluding dimethylaminopyridine). The reaction mixture was cooled to room temperature and then triethylamine and tetrahydrofuran were removed under vacuum at 30° C. The solution was then neutralized with acetic acid to a pH of 7.69. N,N-dimethylformamidine was removed under vacuum at 35° C. and chased with ethyl acetate (2×200 mL). The crude product was stirred with ethyl acetate (500 mL) and water (300 mL). The two layers were separated and the aqueous layer was extracted with ethyl acetate (500 mL). The combined organic layers were washed with an aqueous saturated brine solution (500 mL). Next the organic layer was extracted with an aqueous solution of malonic acid (4×400 mL, 10 wt. %). The organic layer was checked by TLC (silica, 20% methanol in dichloromethane) to make sure that all the desired product was removed from the organic layer. The acidic aqueous extracts were combined and cooled in an ice bath and neutralized with triethylamine to a pH of 7.40 so that the solids fell out of solution. Ethyl acetate then was added to the aqueous layer. The white solids were collected by vacuum filtration. Drying the obtained solids in vacuum gave 81.08 g of 99.01 pure (HPLC) first crop.

Step 8: Synthesis of val-mCyd-2-Amino-3-methyl-butyric acid 5-(4-amino-2-oxo-2H-pyrimidine-1-yl)-4-hydroxy-2 hydroxy-methyl-4-methyl-tetrahydro-furan-3-yl ester (dihydrochloride salt)

A solution of compound 14 (21.0 g, 0.046 mol) in ethanol (168 ml) was stirred in a round bottomed flask equipped with an overhead stirrer, temperature probe, argon line and hydrogen chloride gas bubbler. Hydrogen chloride gas (22 g) was bubbled into the clear solution over a period of one hour. The reaction temperature was kept below 30° C. using an ice-water bath. Solid formation started after a few minutes of introducing the hydrogen chloride gas. After 4 hours, HPLC (method # 3) showed only 0.8% of starting material. Solids were collected by filtration and filter cake washed with ethanol (20 ml) and di-ethyl ether (100 ml). After drying product under vacuum for 16 hours, 19.06 g (96.5%) of val-mCyd was obtained in 97.26% purity (HPLC, method # 3); m.p. 210° C. (brown), 248-250° C. (melted); $^1$H NMR (DMSO-$d_6$) δ ppm 10.0 (s, 1H, ½NH$_2$, D$_2$O exchangeable), 8.9-8.6 (2 br s, 4H, ½NH$_2$, NH$_3$, D$_2$O exchangeable), 8.42 (d, 1H, H-6, J$_{5-6}$=7.9 Hz), 6.24 (d, 1H, H-5, J$_{5-6}$=7.9 Hz), 5.84 (s, 1H, H-1'), 5.12 (d, 1H, H-3', J$_{3'-4'}$=8.8 Hz), 4.22 (d, 1H, H-4, J$_{3'-4'}$=8.7 Hz), 4.0-3.9 (m, 1H, CH), 3.8-3.5 (m, 2H, H-5', H-5"), 2.3-2.1 (m, 1H, CH), 1.16 (s, 3H, CH$_3$), 1.0 (m, 6H, (CH$_3$)$_2$CH); FAB>0 (GT) 713 (2M+H)$^+$, 449 (M+G+H)$^+$, 357 (M+H)$^+$, 246 (S)$^+$, 112 (B+2H)$^+$; FAB<0 (GT) 747 (2M+Cl)$^-$, 483 (M+G+Cl)$^-$, 391 (M+Cl)$^-$, 355 (M−H)$^-$, 116 (Val)$^-$, 110 (B)$^-$, 35 (Cl).

Two different HPLC methods were used to analyze the above compounds. Both methods use the following reverse phase column:

Method 1

254 nm. 1.00 ml/min flow rate of an acetonitrile/water linear gradient as described below. 20 minute run time. Five-minute equilibration between runs.

TABLE 1

Retention time of key intermediates:

| Compound | Retention Time |
| --- | --- |
| Compound 10 | 10.2 min |
| Compound 11 | 9.4 min |
| Compound 12 | 12.9 min |

Method 2

Identification is determined at 272 nm. The column used is a Waters Novapak® C18, 3.9×150 mm ID, 4 µm particle size, 60 Å pore size or equivalent. The chromatographic conditions are as follows: injection volume=10 µl, column temperature=25° C., flow rate=1.00 ml/min, ultraviolet detector at 272 nm, run time is 35 minutes. The system suitability requirement for the percent relative standard deviation for the reference standard is not more than 1.0%.

TABLE 2a

Purity and impurities are determined at 272 nm:

| Time (minutes) | Solvent A - 20 nM triethylammonium acetate buffer | Solvent B - Acetonitrile, HPLC grade. |
| --- | --- | --- |
| 0.00 | 100.0 | 0.0 |
| 10.00 | 85.0 | 15.0 |
| 25.00 | 5.0 | 95.0 |
| 35.0 | 5.0 | 95.0 |

TABLE 2b

Retention times of key intermediates and final drug substance:

| Compound | Retention Time (minutes) |
| --- | --- |
| Compound mCyd | 2.7-2.8 |
| Compound 14 | 15.5 |
| val-mCyd | 9.1 |

Stereochemistry

It is appreciated that nucleosides of the present invention have several chiral centers and may exist in and be isolated in optically active and racemic forms. Some compounds may exhibit polymorphism. It is to be understood that the present invention encompasses any racemic, optically-active, diastereomeric, polymorphic, or stereoisomeric form, or mixtures thereof, of a compound of the invention, which possess the useful properties described herein. It being well known in the art how to prepare optically active forms (for example, by resolution of the racemic form by recrystallization techniques, by synthesis from optically-active starting materials, by chiral synthesis, or by chromatographic separation using a chiral stationary phase).

In particular, since the 1' and 4' carbons of the nucleoside are chiral, their nonhydrogen substituents (the base and the CHOR groups, respectively) can be either cis (on the same side) or trans (on opposite sides) with respect to the sugar ring system. The four optical isomers therefore are represented by the following configurations (when orienting the sugar moiety in a horizontal plane such that the oxygen atom is in the back): cis (with both groups "up", which corresponds to the configuration of naturally occurring β-D nucleosides), cis (with both groups "down", which is a normaturally occurring β-L configuration), trans (with the C2' substituent "up" and the C4' substituent "down"), and trans (with the C2' substituent "down" and the C4' substituent "up"). The "D-nucleosides" are cis nucleosides in a natural configuration and the "L-nucleosides" are cis nucleosides in the normaturally occurring configuration.

Likewise, most amino acids are chiral (designated as L or D, wherein the L enantiomer is the naturally occurring configuration) and can exist as separate enantiomers.

Examples of methods to obtain optically active materials are known in the art, and include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme exists;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

III. Pharmaceutical Compositions

Hosts, including humans, infected with pestivirus, flavivirus, HCV or another organism replicating through a RNA-dependent RNA viral polymerase, or for treating any other disorder described herein, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound for pestivirus, flavivirus or HCV will be in the range from about 1 to 50 mg/kg, preferably 1 to 20 mg/kg, of body weight per day, more generally 0.1 to about 100 mg per kilogram body weight of the recipient per day. Lower doses may be preferable, for example doses of 0.5-100 mg, 0.5-50 mg, 0.5-10 mg, or 0.5-5 mg per kilogram body weight per day. Even lower doses may be useful, and thus ranges can include from 0.1-0.5 mg per kilogram body weight per day. The effective dosage range of the pharmaceutically acceptable salts and prodrugs can be calculated based on the weight of the parent nucleoside to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to one containing 7 to 3000 mg, preferably 70 to 1400 mg of active ingredient per unit dosage form. An oral dosage of 50-1000 mg is usually convenient, including in one or multiple dosage forms of 50, 100, 200, 250, 300, 400, 500, 600, 700, 800, 900 or 1000 mgs. Lower doses may be preferable, for example from 10-100 or 1-50 mg. Also contemplated are doses of 0.1-50 mg, or 0.1-20 mg or 0.1-10.0 mg. Furthermore, lower doses may be utilized in the case of administration by a non-oral route, as, for example, by injection or inhalation.

Ideally the active ingredient should be administered to achieve peak plasma concentrations of the active compound of from about 0.2 to 70 $\mu$M, preferably about 1.0 to 10 $\mu$M. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time, with or without other anti-viral agents.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salt thereof can also be mixed with other active materials that do not impair the desired action, or with materials that supplement the desired action, such as antibiotics, antifungals, anti-inflammatories, or other antivirals, including other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems, biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation.

Liposomal suspensions (including liposome's targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s), such as sterol phosphatidyl ethanolamine, stearoyl phosphatidyl choline, arachadoyl phosphatidyl choline, and cholesterol, in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

IV. Prodrugs and Derivatives

Salt Formulations

Administration of the nucleoside as a pharmaceutically acceptable salt is within the scope of the invention. Examples of pharmaceutically acceptable salts are organic acid addition salts formed with acids, which provide a physiological acceptable anion. These include, for example, tosylate, methanesulfonate, acetate, citrate, malonate, tartarate, succinate, benzoate, ascorbate, α-ketoglutarate, and α-glycerophosphate, formate, fumarate, propionate, glycolate, lactate, pyruvate, oxalate, maleate, and salicyate. Suitable inorganic salts may also be formed, including, sulfate, nitrate, bicarbonate, hydrobromate, carbonate salts, and phosphoric acid. A particularly preferred embodiment is the mono or dihydrochloride salt.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made. In one embodiment, the salt is a hydrochloride salt of the compound. In a further embodiment, the pharmaceutically acceptable salt is a dihydrochloride salt of the compound of Formula (I). The compounds of this invention possess antiviral activity against flavivirus, pestivirus or HCV, or are metabolized to a compound that exhibits such activity.

Nucleotide Prodrugs

The nucleosides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono-, di- or triphosphate of the nucleoside reduces polarity and allows passage into cells. Examples of substituent groups that can replace one or more hydrogens on the phosphate moiety are alkyl, aryl, steroids, carbohydrates, including sugars, and alcohols, such as 1,2-diacylglycerol. Many are described in R. Jones and N. Bischoferger, *Antiviral Research,* 1995, 27:1-17. Any of these can be used in combination with the disclosed nucleosides to achieve a desired effect.

The active nucleoside can also be provided as a 5'-phosphoether lipid or a 5'-ether lipid. Non-limiting examples are disclosed in the following references, which are incorporated by reference herein: Kucera, L. S., N. Iyer, E. Leake, A. Raen, Modest E. K., D. L. W., and C. Piantadosi. 1990. "Novel membrane-interactive ether lipid analogs that inhibit infectious HIV-1 production and induce defective virus formation." *AIDS Res. Hum. Retro Viruses.* 6:491-501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hostetler, K. Y., D. D. Richman, D. A. Carson, L. M. Stuhmiller, G. M. T. van Wijk, and H. van den Bosch., 1992. "Greatly enhanced inhibition of human immunodeficiency virus type I replication in CEM and HT4-6C cells by 3'-deoxythymidine diphosphate dimyristoylglycerol, a lipid prodrug of 3-deoxythymidine." *Antimicro. Agents Chemother.* 36:2025.2029; Hosetler, K. Y., L. M. Stuhmiller, H. Lenting, H. van den Bosch, and D. D. Richman, 1990. "Synthesis and antiretroviral activity of phospholipid analogs of azidothymidine and other antiviral nucleosides." *J. Biol. Chem.* 265:61127.

Nonlimiting examples of U.S. patents that disclose suitable lipophilic substituents that can be covalently incorporated into the nucleoside, preferably at the 5'-OH position of the nucleoside or lipophilic preparations thereof, include U.S. Pat. Nos. 5,149,794 (Sep. 22, 1992, Yatvin et al.); 5,194,654 (Mar. 16, 1993, Hostetler et al., 5,223,263 (Jun. 29, 1993, Hostetler et al.); 5,256,641 (Oct. 26, 1993, Yatvin et al.); 5,411,947 (May 2, 1995, Hostetler et al.); 5,463,092 (Oct. 31, 1995, Hostetler et al.); 5,543,389 (Aug. 6, 1996, Yatvin et al.); 5,543,390 (Aug. 6, 1996, Yatvin et al.); 5,543,391 (Aug. 6, 1996, Yatvin et al.); and 5,554,728 (Sep. 10, 1996; Basava et al.), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

V. Combination or Alternation Therapy

The active compounds of the present invention can be administered in combination or alternation with another anti-flavivirus or pestivirus agent, or in particular an anti-HCV agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. In preferred embodiments, an anti-HCV (or anti-pestivirus or anti-flavivirus) compound that exhibits an $EC_{50}$ of 10-15 μM, or preferably less than 1-5 μM, is desirable.

It has been recognized that drug-resistant variants of flaviviruses, pestiviruses or HCV can emerge after prolonged treatment with an antiviral agent. Drug resistance most typically occurs by mutation of a gene that encodes for an enzyme used in viral replication. The efficacy of a drug against the viral infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameters of the drug can be altered by such combination or alternation therapy. In general, combination therapy is typically preferred over alternation therapy because it induces multiple simultaneous stresses on the virus.

Any of the viral treatments described in the Background of the Invention can be used in combination or alternation with the compounds described in this specification. Nonlimiting examples include:

(1) Protease inhibitors

Examples include substrate-based NS3 protease inhibitors (Attwood et al., Antiviral peptide derivatives, PCT WO 98/22496, 1998; Attwood et al., *Antiviral Chemistry and Chemotherapy* 1999, 10, 259-273; Attwood et al, Preparation and use of amino acid derivatives as anti-viral agents, German Patent Pub. DE 19914474; Tung et al. Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate (Llinas-Brunet et al, Hepatitis C inhibitor peptide analogues, PCT WO 99/07734); Non-substrate-based NS3 protease inhibitors such as 2,4,6-trihydroxy-3-nitro-benzamide derivatives (Sudo K. et al., *Biochemical and Biophysical Research Communications*, 1997, 238, 643-647; Sudo K. et al. *Antiviral Chemistry and Chemotherapy*, 1998, 9, 186), including RD3-4082 and RD3-4078, the former substituted on the amide with a 14 carbon chain and the latter processing a para-phenoxyphenyl group; and Sch 68631, a phenanthrenequinone, an HCV protease inhibitor (Chu M. et al., *Tetrahedron Letters* 37:7229-7232, 1996).

Sch 351633, isolated from the fungus *Penicillium griseofulvum*, was identified as a protease inhibitor (Chu M. et al., *Bioorganic and Medicinal Chemistry Letters* 9:1949-1952). Eglin c, isolated from leech, is a potent inhibitor of several serine proteases such as *S. griseus* proteases A and B, α-chymotrypsin, chymase and subtilisin. Qasim M. A. et al., *Biochemistry* 36:1598-1607, 1997.

U.S. patents disclosing protease inhibitors for the treatment of HCV include, for example, U.S. Pat. No. 6,004,933 to Spruce et al. which discloses a class of cysteine protease inhibitors for inhibiting HCV endopeptidase 2; U.S. Pat. No. 5,990,276 to Zhang et al. which discloses synthetic inhibitors of hepatitis C virus NS3 protease; U.S. Pat. No. 5,538,865 to Reyes et a; WO 02/008251 to Corvas International, Inc, and WO 02/08187 and WO 02/008256 to Schering Corporation. HCV inhibitor tripeptides are disclosed in U.S. Pat. Nos. 6,534,523, 6,410,531, and 6,420,380 to Boehringer Ingelheim and WO 02/060926 to Bristol Myers Squibb. Diaryl peptides as NS3 serine protease inhibitors of HCV are disclosed in WO 02/48172 to Schering Corporation. Imidazolidindiones as NS3 serine protease inhibitors of HCV are disclosed in WO 02/08198 to Schering Corporation and WO 02/48157 to Bristol Myers Squibb. WO 98/17679 to Vertex Pharmaceuticals and WO 02/48116 to Bristol Myers Squibb also disclose HCV protease inhibitors.

(2) Thiazolidine derivatives which show relevant inhibition in a reverse-phase HPLC assay with an NS3/4A fusion protein and NS5A/5B substrate (Sudo K. et al., *Antiviral Research*, 1996, 32, 9-18), especially compound RD-1-6250, possessing a fused cinnamoyl moiety substituted with a long alkyl chain, RD4 6205 and RD4 6193;

(3) Thiazolidines and benzanilides identified in Kakiuchi N. et al. *J. EBS Letters* 421, 217-220; Takeshita N. et al. *Analytical Biochemistry*, 1997, 247, 242-246;

(4) A phenan-threnequinone possessing activity against protease in a SDS-PAGE and autoradiography assay isolated from the fermentation culture broth of *Streptomyces* sp., Sch 68631 (Chu M. et al., *Tetrahedron Letters*, 1996, 37, 7229-7232), and Sch 351633, isolated from the fungus *Penicillium griseofulvum*, which demonstrates activity in a scintillation proximity assay (Chu M. et al., *Bioorganic and Medicinal Chemistry Letters* 9, 1949-1952);

(5) Helicase inhibitors (Diana G. D. et al., Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554);

(6) Nucleotide polymerase inhibitors and gliotoxin (Ferrari R. et al. *Journal of Virology*, 1999, 73, 1649-1654), and the natural product cerulenin (Lohmann V. et al., *Virology*, 1998, 249, 108-118);

(7) Antisense phosphorothioate oligodeoxynucleotides (S-ODN) complementary to sequence stretches in the 5' non-coding region (NCR) of the virus (Alt M. et al, *Hepatology*, 1995, 22, 707-717), or nucleotides 326-348 comprising the 3' end of the NCR and nucleotides 371-388 located in the core coding region of the HCV RNA (Alt M. et al., *Archives of Virology*, 1997, 142, 589-599; Galderisi U. et al., *Journal of Cellular Physiology*, 1999, 181, 251-257);

(8) Inhibitors of IRES-dependent translation (Ikeda N et al., Agent for the prevention and treatment of hepatitis C, Japanese Patent Pub. JP-08268890; Kai Y. et al. Prevention and treatment of viral diseases, Japanese Patent Pub. JP-10101591);

(9) Ribozymes, such as nuclease-resistant ribozymes (Maccjak, D. J. et al., *Hepatology* 1999, 30, abstract 995) and those disclosed in U.S. Pat. No. 6,043,077 to Barber et al., and U.S. Pat. Nos. 5,869,253 and 5,610,054 to Draper et al.; and

(10) Nucleoside analogs have also been developed for the treatment of Flaviviridae infections.

(11) Any of the compounds described by Idenix Pharmaceuticals in International Publication Nos. WO 01/90121 and WO 01/92282;

(12) Other patent applications disclosing the use of certain nucleoside analogs to treat hepatitis C virus include: PCT/CA00/01316 (WO 01/32153; filed Nov. 3, 2000) and PCT/CA01/00197 (WO 01/60315; filed Feb. 19, 2001) filed by BioChem Pharma, Inc. (now Shire Biochem, Inc.); PCT/US02/01531 (WO 02/057425; filed Jan. 18, 2002) and PCT/US02/03086 (WO 02/057287; filed Jan. 18, 2002) filed by Merck & Co., Inc., PCT/EP01/09633 (WO 02/18404; published Aug. 21, 2001) filed by Roche, and PCT Publication Nos. WO 01/79246 (filed Apr. 13, 2001), WO 02/32920 (filed Oct. 18, 2001) and WO 02/48165 by Pharmasset, Ltd.

(13) PCT Publication No. WO 99/43691 to Emory University, entitled "2'-Fluoronucleosides" discloses the use of certain 2'-fluoronucleosides to treat HCV.

(14) Other miscellaneous compounds including 1-aminoalkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), benzimidazoles (U.S. Pat. No. 5,891,874 to Colacino et al), plant extracts (U.S. Pat. No. 5,837,257 to Tsai et al., U.S. Pat. No. 5,725,859 to Omer et al., and U.S. Pat. No. 6,056,961), and piperadines (U.S. Pat. No. 5,830,905 to Diana et al.).

(15) Any other compound currently in preclinical or clinical development for treatment of hepatitis C virus including: Interleukin-10 by Schering-Plough, IP-501 by Interneuron, Merimebodib (VX-497) by Vertex, AMANTADINE® (Symmetrel) by Endo Labs Solvay, HEPTAZYME® by RPI, IDN-6556 by Idun Pharma., XTL-002 by XTL., HCV/MF59 by Chiron, CIVACIR (Hepatitis C Immune Globulin) by NABI, LEVOVIRIN® by ICN/Ribapharm, VIRAMIDINE® by ICN/Ribaphamm, ZADAXIN® (thymosin alpha-1) by Sci Clone, thymosin plus pegylated interferon by Sci Clone, CEPLENE® (histamine dihydrochloride) by Maxim, VX 950/LY 570310 by Vertex/Eli Lilly, ISIS 14803 by Isis Pharmaceutical/Elan, IDN-6556 by Idun Pharmaceuticals, Inc., JTK 003 by AKROS Pharma, BILN-2061 by Boehringer Ingelheim, CellCept (mycophenolate mofetil) by Roche, T67, a β-tubulin inhibitor, by Tularik, a therapeutic vaccine directed to E2 by Innogenetics, FK788 by Fujisawa Healthcare, Inc., 1 dB 1016 (Siliphos, oral silybin-phosphatdylcholine phytosome), RNA replication inhibitors (VP50406) by ViroPharma/Wyeth, therapeutic vaccine by Intercell, therapeutic vaccine by Epimmune/Genencor, IRES inhibitor by Anadys, ANA 245 and ANA 246 by Anadys, immunotherapy (Therapore) by Avant, protease inhibitor by Corvas/SChering, helicase inhibitor by Vertex, fusion inhibitor by Trimeris, T cell therapy by CellExSys, polymerase inhibitor by Biocryst, targeted RNA chemistry by PTC Therapeutics, Dication by Immtech, Int., protease inhibitor by Agouron, protease inhibitor by Chiron/Medivir, antisense therapy by AVI BioPharma, antisense therapy by Hybridon, hemopurifier by Aethlon Medical, therapeutic vaccine by Merix, protease inhibitor by Bristol-Myers Squibb/Axys, Chron-VacC, a therapeutic vaccine, by Tripep, UT 231B by United Therapeutics, protease, helicase and polymerase inhibitors by Genelabs Technologies, IRES inhibitors by Immusol, R803 by Rigel Pharmaceuticals, INFERGEN® (interferon alphacon-1) by InterMune, OMNIFERON® (natural interferon) by Viragen, ALBUFERON® by Human Genome Sciences, REBIF (interferon beta-1a) by Ares-Serono, Omega Interferon by BioMedicine, Oral Interferon Alpha by Amarillo Biosciences, interferon gamma, interferon tau, and Interferon gamma-1b by InterMune.

V. Biological Data

Cell Culture Systems for Determining Antiviral Activities

A useful cell-based assay to detect HCV and its inhibition assesses the levels of replicon RNA from Huh7 cells harboring the HCV replicon. These cells can be cultivated in standard media, for example DMEM medium (high glucose, no pyruvate), supplemented with 10% fetal bovine serum, 1× non-essential amino acids, Pen-Strep-Glu (100 units/liter, 100 microgram/liter, and 2.92 mg/liter, respectively), and G418 ($C_{20}H_{40}N_4O_{10}$; 500 to 1000 microgram/milliliter). Antiviral screening assays can be done in the same medium without G418. To keep the cells in the logarithmic growth phase, cells are seeded in 96-well plates at low density (for example, 1000 cells per well). The test compound is then added immediately after seeding the cells and they are incubated for 3 to 7 days at 37° C. in an incubator. The medium is then removed, and the cells prepared for total RNA extraction (replicon RNA+host RNA). Replicon RNA can then be amplified in a real-time RT-PCR (Q-RT-PCR) protocol, and quantified.

The observed differences in quantification of replicon RNA are one way to express the antiviral potency of the test compound. In a typical experiment, a comparable amount of replicon is produced in the negative control and with non-active compounds. This can be concluded if the measured threshold-cycle for HCV RT-PCR in both setting is approximately the same. In such experiments, a way to express the antiviral effectiveness of a compound is to subtract the average threshold RT-PCR cycle of the negative control ($Ct_{negative}$) from the threshold RT-PCR cycle of the test compound ($Ct_{testcompound}$). This value is called ΔCt ($\Delta Ct = Ct_{testcompound} - Ct_{negative}$). A ΔCt value of 3.3 represents a 1-log reduction in replicon production. As a positive control, recombinant interferon alpha-2a (for example, Roferon-A, Hoffmann-Roche, N.J., USA) can be used alongside the test compound. Furthermore, the compounds can be tested in dilution series (typically at 100, 33, 10, 3 and 1 μM). The ΔCt values for each concentration allow the calculation of the 50% effective concentration ($EC_{50}$).

The assay described above can be adapted to the other members of the Flaviviridae by changing the cell system and the viral pathogen. Methodologies to determine the efficacy of these antiviral compounds include modifications of the standard techniques as described by Holbrook M R et al. *Virus Res.* 2000, 69, 31; Markland W et al. *Antimicrob. Agents. Chemother.* 2000, 44, 859; Diamond M S et al., *J. Virol.* 2000, 74, 7814; Jordan I et al. *J. Infect. Dis.* 2000, 182, 1214; Sreenivasan V et al. *J. Virol. Methods* 1993, 45 (1), 1; or Baginski S G et al. *Proc. Natl. Acad. Sci. U.S.A.* 2000, 97 (14), 7981 or the real-time RT-PCR technology. As an example, an HCV replicon system in HuH7 cells (Lohmann V et al. *Science.* 1999, 285 (5424), 110) or modifications thereof (Blight et al. 2000) can be used.

Non-Cell Based Assays Adapted for Detecting HCV

Nucleic acid amplification technology is now the method of choice for identification of a large and still growing number of microorganisms such as *Mycobacterium tuberculosis*, human immunodeficiency virus (HIV), and hepatitis C virus (HCV) in biological samples. Nucleic acid amplification techniques include the polymerase chain reaction (PCR), ligase chain reaction (LCR), nucleic acid sequence-based amplification (NASBA), strand-displacement amplification (SDA), and transcription-mediated amplification (TMA). Several FDA-approved diagnostic products incorporate these molecular diagnostic methods (see Table below). Nucleic acid amplification technology tests involve not only amplification, but detection methodologies as well. The promise of molecular diagnostics lies in the improvement of its specimen-processing, amplification, and target-detection steps, and in the integration of these steps into an automated format.

| FDA- Approved Assays | Amplification Product: Detection Method | Nucleic Acid Amplification Method | Commercial Source |
|---|---|---|---|
| C. trachomatis, N. gonorrhoeae, M. tuberculosis, HIV-1 | Heterogeneous: Colorimetric | PCR | Roche Diagnostics |
| C. trachomatis, N. gonorrhoeae | Heterogeneous: Chemiluminescence | LCR | Abbott Laboratories |
| C. trachomatis, N. gonorrhoeae | Homogeneous: Fluorescence | SDA | Becton Dickinson |
| C. trachomatis, M. tuberculosis | Homogeneous: Chemiluminescence (HPA) | TMA | Gen-Probe |

Amplified-Product Detection Schemes

Amplified-product detection schemes are of two basic types: heterogeneous and homogeneous. Heterogeneous detection is characterized by a distinct step, such as washing, designed to remove unhybridized probes from hybridized probes, whereas in homogeneous detection there is no physical separation step to remove free probe from bound probe. Multiple heterogeneous and homogeneous detection methods exist. Any of these heterogeneous or homogeneous assays can be utilized to assess the effectiveness of the compounds of the present invention versus an RNA-dependent RNA polymerase virus, such as HCV.

Heterogeneous Detection: Southern blotting, for example, is a heterogeneous detection technique. In Southern blotting, electrophoresis is used to separate amplification products by size and charge. The size-fractionated products are transferred to a membrane or filter by diffusion, vacuuming, or electroblotting. Labeled detection probes are then hybridized to the membrane-bound targets in solution, the filters are washed to remove any unhybridized probe, and the hybridized probe on the membrane is detected by any of a variety of methods.

Other types of heterogeneous detection are based on specific capture of the amplification products by means of enzyme-linked immunosorbent assays (ELISAs). One method used with PCR involves labeling one primer with a hapten or a ligand, such as biotin, and, after amplification, capturing it with an antibody- or streptavidin-coated microplate. The other primer is labeled with a reporter such as fluorescein, and detection is achieved by adding an antifluorescein antibody, horseradish peroxidase (HRP) conjugate. This type of method is not as specific as using detection probes that hybridize to defined amplification products of interest.

The LCx probe system (Abbott Laboratories; Abbott Park, Ill.) and the Amplicor HIV-1 test (Roche Molecular Systems Inc.; Pleasanton, Calif.) are systems that use heterogeneous detection methods. In the LCx system, hapten-labeled oligonucleotide probes thermocycle in the ligase chain reaction. Either a capture hapten or a detection hapten is covalently attached to each of the four primer oligonucleotides. Upon amplification, each amplified product (amplicon) has one capture hapten and one detection hapten. When amplification is complete, the LCx system instrument transfers the reaction to a new well where antibody-coated microparticles bind the capture haptens. Each microparticle is then irreversibly bound to a glass-fiber matrix. A wash step removes from the microparticle any probe that contains only the detection hapten. The LCx instrument adds an alkaline phosphatase (AP)- antibody conjugate that binds to the detection hapten. A fluorigenic substrate for AP is 4-methylumbelliferyl. Dephosphorylation of 4-methylumbelliferyl by AP converts it to 4-methylumbelliferone, which is fluorescent.

The Amplicor HIV-1 test uses an ELISA format. After amplification by PCR, the amplicon is chemically denatured. Amplicon-specific oligonucleotide probes capture the denatured strands onto a coated microplate. The operator washes away any unincorporated primers and unhybridized material in a wash step and then adds an avidin-HRP conjugate to each well. The conjugate binds to the biotin-labeled amplicon captured on the plate. The operator then adds 3,3',5,5'-tetramethylbenzidine (TMB), a chromogenic HRP substrate. When hydrogen peroxide is present, HRP oxidizes TMB. The signal is determined colorimetrically.

Homogeneous Detection: Because hybridized and nonhybridized detection probes are not physically separated in homogeneous detection systems, these methods require fewer steps than heterogeneous methods and thus are less prone to contamination. Among the commercially available kits that use homogeneous detection of fluorescent and chemiluminescent labels are the TaqMan system (Applied Biosystems; Foster City, Calif.), BDProbeTecET system (Becton Dickinson; Franklin Lakes, N.J.), QPCR System 5000 (Perkin-Elmer Corp.; Norwalk, Conn.), and Hybridization Protection Assay (Gen-Probe Inc.; San Diego).

The TaqMan system detects amplicon in real time. The detection probe, which hybridizes to a region inside the amplicon, contains a donor fluorophore such as fluoroscein at its 5' end and a quencher moiety, for example, rhodamine, at its 3' end. When both quencher and fluorophore are on the same oligonucleotide, donor fluorescence is inhibited. During amplification the probe is bound to the target. Taq polymerase displaces and cleaves the detection probe as it synthesizes the replacement strand. Cleavage of the detection probe results in separation of the fluorophore from the quencher, leading to an increase in the donor fluorescence signal. During each cycle of amplification the process is repeated. The amount of fluorescent signal increases as the amount of amplicon increases.

Molecular beacons use quenchers and fluorophores also. Beacons are probes that are complementary to the target amplicon, but contain short stretches (approximately 5 nucleotides) of complementary oligonucleotides at each end. The 5' and 3' ends of the beacons are labeled with a fluorophore and a quencher, respectively. A hairpin structure is formed when the beacon is not hybridized to a target, bringing into contact the fluorophore and the quencher and resulting in fluorescent quenching. The loop region contains the region complementary to the amplicon. Upon hybridization to a target, the hairpin structure opens and the quencher and fluorophore separate, allowing development of a fluorescent signal.[14] A fluorometer measures the signal in real time.

The BDProbeTecET system uses a real-time detection method that combines aspects of TaqMan and molecular beacons. The probe has a hairpin loop structure and contains fluorescein and rhodamine labels. In this system, however, the region complementary to the target molecule is not within the loop but rather in the region 3' to the rhodamine label. Instead of containing the sequence complementary to the target, the single-stranded loop contains a restriction site for the restriction enzyme BsoBI. The single-stranded sequence is not a substrate for the enzyme. The fluorescein and rhodamine labels are near each other before amplification, which quenches the fluorescein fluorescence. Strand-displacement amplification converts the probe into a double-stranded molecule. The BsoBI restriction enzyme can then cleave the molecule, resulting in separation of the labels and an increase in the fluorescent signal.

The QPCR System 5000 employs electrochemiluminescence with ruthenium labels. A biotinylated primer is used. After amplification, the biotin products are captured on streptavidin-coated paramagnetic beads. The beads are transferred into an electrochemical flow cell by aspiration and magnetically held to the surface of the electrode. Upon electrical stimulation, the ruthenium-labeled probe emits light.

The Hybridization Protection Assay is used in Gen-Probe's nonamplified PACE assays as well as in amplified *Mycobacterium tuberculosis* and *Chlamydia trachomatis* assays. The detection oligonucleotide probes in HPA are labeled with chemiluminescent acridinium ester (AE) by means of a linker arm. Hybridization takes place for 15 minutes at 60° C. in the same tube in which the amplification occurred. The selection reagent, a mildly basic buffered solution added after hybridization, hydrolyzes the AE on any unhybridized probe, rendering it nonchemiluminescent. The AE on hybridized probes folds inside the minor groove of the double helix, thereby protecting itself from hydrolysis by the selection reagent. The AE emits a chemiluminescent signal upon hydrolysis by hydrogen peroxide followed by sodium hydroxide. A luminometer records the chemiluminescent signal for 2 seconds (a period termed a light-off) and reports the photons emitted in terms of relative light units (RLU).

Detection-probe design is critical in all methodologies that use probes to detect amplification products. Good detection probes hybridize only to specified amplification product and do not hybridize to nonspecific products. Other key issues in optimizing detection methodologies involve the labeling of probes and the maximization of sample throughput.

Labeling Methods and Reporter Molecules. Detection probes can be labeled several different ways. Enzymatic incorporation of $^{32}P$ or $^{35}S$ into the probes is the most common method for isotopic labeling. Following hybridization and washing, the signal is detected on autoradiographic film.

To perform nonradioactive detection, probes can be enzymatically labeled with a variety of molecules. Biotin can be incorporated enzymatically and then detected with streptavidin-conjugated alkaline phosphatase, using AP substrates like 5-bromo-4-chloro-3-indolyl phosphate (BCIP) and nitroblue tetrazolium (NBT). Chemiluminescent substrates such as Lumi-Phos 530 or Lumi-Phos Plus (Lumigen, Southfield, Mich.) can also be used with AP. In addition, digoxigenin-11-dUTP can be incorporated enzymatically into DNA or RNA, and antidigoxigenin AP conjugates can be used with calorimetric or chemiluminescent detection.

There are numerous other types of reporter molecules, including chemiluminescent moieties such as acridinium esters. Many fluorescent moieties are available as well. Electrochemiluminescent compounds such as tris(2,2'-bipyridine) ruthenium (II) can be used also. Further discussions of these and similar techniques can be found in: Schiff E R, de Medina M, Kahn R S. *Semin Liver Dis.* 1999; 19(Suppl 1:3-15).

EXAMPLE 3

Cellular Pharmacology of 2'-C-methyl-cytidine-3'-O-L-valine ester (val-mCyd)

Phosphorylation Assay of Nucleoside to Active Triphosphate

To determine the cellular metabolism of the compounds, HepG2 cells are obtained from the American Type Culture Collection (Rockville, Md.), and are grown in 225 cm² tissue culture flasks in minimal essential medium supplemented with non-essential amino acids, 1% penicillin-streptomycin. The medium is renewed every three days, and the cells are subcultured once a week. After detachment of the adherent monolayer with a 10 minute exposure to 30 mL of trypsin-EDTA and three consecutive washes with medium, confluent HepG2 cells are seeded at a density of $2.5 \times 10^6$ cells per well in a 6-well plate and exposed to 10 µM of [$^3$H] labeled active compound (500 dpm/pmol) for the specified time periods. The cells are maintained at 37° C. under a 5% $CO_2$ atmosphere. At the selected time points, the cells are washed three times with ice-cold phosphate-buffered saline (PBS). Intracellular active compound and its respective metabolites are extracted by incubating the cell pellet overnight at -20° C. with 60% methanol followed by extraction with an additional 20 µL of cold methanol for one hour in an ice bath. The extracts are then combined, dried under gentle filtered air flow and stored at -20° C. until HPLC analysis.

Antiviral nucleosides and nucleoside analogs are generally converted into the active metabolite, the 5'-triphosphate (TP) derivatives by intracellular kinases. The nucleoside-TPs then exert their antiviral effect by inhibiting the viral polymerase during virus replication. In primary human hepatocyte cultures, in a human hepatoma cell line (HepG2), and in a bovine kidney cell line (MDBK), mCyd was converted into a major metabolite, 2'-C-methyl-cytidine-5'-triphosphate (mCyd-TP), along with smaller amounts of a uridine 5'-triphosphate derivative, 2'-C-methyl-uridine-5'-triphosphate (mUrd-TP). mCyd-TP is inhibitory when tested in vitro against the BVDV replication enzyme, the NS5B RNA dependent RNA polymerase, and was thought to be responsible for the antiviral activity of mCyd.

The cellular metabolism of mCyd was examined using MDBK cells, HepG2 cells and human primary hepatocytes exposed to 10 µM [$^3$H]-mCyd. High-pressure liquid chromatography (HPLC) analysis demonstrated that mCyd was phosphorylated in all three cell types, with mCyd-TP being the predominant metabolite after 24 h. The metabolic profile obtained over a 48-hour exposure of human hepatoma HepG2 cells to 10 µM [$^3$H]-mCyd was tested. In HepG2 cells, levels of mCyd-TP peaked at 41.5±13.4 µM after 24 hours (see Table 3) and fell slowly thereafter. In primary human hepatocytes, the peak mCyd-TP concentration at 24 hours was 4 fold lower at 10.7±6.7 µM. MDBK bovine kidney cells yielded intermediate levels of mCyd-TP (30.1±6.9 µM at 24 hours).

Exposure of hepatocytes to mCyd led to production of a second 5'-triphosphate derivative, mUrd-TP. In HepG2 cells exposed to 10 µM [$^3$H]-mCyd, the mUrd-TP level reached 1.9±1.6 µM at 24 hours, compared to 8.1±3.4 µM in MDBK cells and 3.2±2.0 µM in primary human hepatocytes. While MDBK and HepG2 cells produced comparable total amounts of phosphorylated species (approximately 43 versus 47 µM, respectively) at 24 h, mUrd-TP comprised 19% of the total product in MDBK cells versus only 4% in HepG2 cells. mUrd-TP concentration increased steadily over time, however reached a plateau or declined after 24 hours.

cell lines, respectively. The $CC_{50}$ for mCyd in HepG2 cells increased to 200 μM when the cells were grown on collagen-coated plates for 4 or 10 days. For comparison, $CC_{50}$ values of 35-36 μM were derived when ribavirin was tested in HepG2

TABLE 3

Activation of mCyd (10 μM) in Hepatocytes and MDBK Cells

| Cells[a] | n | Metabolite (μM) | | | | | |
|---|---|---|---|---|---|---|---|
| | | mCyd-MP | mUrd-MP | mCyd-DP | mUrd-DP | mCyd-TP | mUrd-TP |
| HepG2 | 6 | ND | ND | 3.7 ± 2.1 | ND | 41.5 ± 13.4 | 1.9 ± 1.6 |
| Human Primary Hepatocytes | 5 | ND | ND | 1.15 ± 1.1 | 0.26 ± 0.4 C | 10.7 ± 6.7 | 3.2 ± 2.0 |
| MDBK Bovine Kidney Cells | 7 | ND | ND | 4.2 ± 2.7 | 0.76 ± 0.95 | 30.1 ± 6.9 | 8.1 ± 3.4 |

[a]Cells were incubated for 24 hours with [$^3$H]-mCyd, specific activity: HepG2 assay = 0.5 Ci/mmol; human and monkey hepatocyte assay = 1.0 Ci/mmol.
[b]The concentrations of metabolites were determined as pmoles per million cells. One pmole per million cells is roughly equivalent to 1 μM.
ND, not detected.

The apparent intracellular half-life of the mCyd-TP was 13.9±2.2 hours in HepG2 cells and 7.6±0.6 hours in MDBK cells: the data were not suitable for calculating the half life of mUrd-TP. Other than the specific differences noted above, the phosphorylation pattern detected in primary human hepatocytes was qualitatively similar to that obtained using HepG2 or MDBK cells.

EXAMPLE 4

Cell Cytotoxicity

Mitochondria Toxicity Assay

HepG2 cells were cultured in 12-well plates as described above and exposed to various concentrations of drugs as taught by Pan-Zhou X-R, Cui L, Zhou X-J, Sommadossi J-P, Darley-Usmer V M. "Differential effects of antiretroviral nucleoside analogs on mitochondrial function in HepG2 cells" Antimicrob. Agents Chemother. 2000; 44:496-503. Lactic acid levels in the culture medium after 4 day drug exposure were measured using a Boehringer lactic acid assay kit. Lactic acid levels were normalized by cell number as measured by hemocytometer count.

Cytotoxicity Assays

Cells were seeded at a rate of between $5 \times 10^3$ and $5 \times 10^4$/well into 96-well plates in growth medium overnight at 37° C. in a humidified $CO_2$ (5%) atmosphere. New growth medium containing serial dilutions of the drugs was then added. After incubation for 4 days, cultures were fixed in 50% TCA and stained with sulforhodamineB. The optical density was read at 550 nm. The cytotoxic concentration was expressed as the concentration required to reduce the cell number by 50% ($CC_{50}$).

Conventional cell proliferation assays were used to assess the cytotoxicity of mCyd and its cellular metabolites in rapidly dividing cells. The inhibitory effect of mCyd was determined to be cytostatic in nature since mCyd showed no toxicity in confluent cells at concentrations far in excess of the corresponding $CC_{50}$ for a specific cell line. mCyd was not cytotoxic to rapidly growing Huh7 human hepatoma cells or H9c2 rat myocardial cells at the highest concentration tested ($CC_{50}$>250 μM). The mCyd $CC_{50}$ values were 132 and 161 μM in BHK-21 hamster kidney and HepG2 human hepatoma cell lines, respectively.

and Huh7 cells. In the MDBK bovine kidney cells used for BVDV antiviral studies, the $CC_{50}$ of mCyd was 36 μM. A similar $CC_{50}$ value (34 μM) was determined for mCyd against MT-4 human T-lymphocyte cells. In addition, mCyd was mostly either non-cytotoxic or weakly cytotoxic ($CC_{50}$>50 to >200 μM) to numerous other cell lines of human and other mammalian origin, including several human carcinoma cell lines, in testing conducted by the National Institutes of Health (NIH) Antiviral Research and Antimicrobial Chemistry Program. Exceptions to this were rapidly proliferating HFF human foreskin fibroblasts and MEF mouse embryo fibroblasts, where mCyd showed greater cytotoxicity ($CC_{50}$s 16.9 and 2.4 μM, respectively). Again, mCyd was much less toxic to stationary phase fibroblasts.

The cytotoxic effect of increasing amounts of mCyd on cellular DNA or RNA synthesis was examined in HepG2 cells exposed to [$^3$H]-thymidine or [$^3$H]-uridine. In HepG2 cells, the $CC_{50}$s of mCyd required to cause 50% reductions in the incorporation of radiolabeled thymidine and uridine into cellular DNA and RNA, were 112 and 186 μM, respectively. The $CC_{50}$ values determined for ribavirin (RBV) for DNA and RNA synthesis, respectively, were 3.16 and 6.85 μM. These values generally reflect the $CC_{50}$s of 161 and 36 μM determined for mCyd and RBV, respectively, in conventional cell proliferation cytotoxicity assays. To assess the incorporation of mCyd into cellular RNA and DNA, HepG2 cells were exposed to 10 μM [$^3$H]-mCyd or control nucleosides (specific activity 5.6-8.0 Ci/mmole, labeled in the base) for 30 hours. Labeled cellular RNA or DNA species were separately isolated and incorporation was determined by scintillation counting. Exposure of HepG2 cells to mCyd resulted in very low levels of incorporation of the ribonucleoside analog into either cellular DNA or RNA (0.0013-0.0014 pmole/μg of nucleic acid). These levels are similar to the 0.0009 and 0.0013 pmole/1 g values determined for the incorporation of ZDV and ddC, respectively, into RNA: since these deoxynucleosides are not expected to incorporate into RNA, these levels likely reflect the assay background. The incorporation of ZDV and ddC into DNA was significantly higher (0.103 and 0.0055 pmole/μg, respectively). Ribavirin (RBV) incorporated into both DNA and RNA at levels 10-fold higher than mCyd.

TABLE 4a

Cellular Nucleic Acid Synthesis and Incorporation Studies in HepG2 Cells (10 μM Drug and Nucleoside Controls)

| Compound | $CC_{50}$ (μM) DNA ([$^3$H]Thymidine) | $CC_{50}$ (μM) RNA ([$^3$H]Uridine) | Incorporated drug amount pmole/μg DNA | Incorporated drug amount pmole/μg RNA |
|---|---|---|---|---|
| mCyd | 112.3 ± 34.5 | 186.1 ± 28.2 | 0.0013 ± 0.0008$^a$ | 0.0014 ± 0.0008$^a$ |
| ZDV | nd | nd | 0.103 ± 0.0123$^a$ | 0.0009 ± 0.0003$^a$ |
| ddC | nd | nd | 0.0055$^b$ | 0.0013$^b$ |
| Ribavirin | 3.16 ± 0.13 | 6.85 ± 1.83 | 0.0120$^b$ | 0.0132$^c$ |

$^a$Data represent mean of three experiments
$^b$Data represent one experiment
$^c$Data represent mean of two experiments
nd, not determined

TABLE 4b

Cytotoxicity of mCyd in Mammalian Cell Lines

| Cell Line$^a$ | n | $CC_{50}$ (μM) |
|---|---|---|
| Huh 7 | 7 | >250 |
| Hep G2 | 6 | 161 ± 19 |
| Hep G2$^b$ | 2 | >200 |
| MDBK | 7 | 36 ± 7 |
| BHK-21 | 2 | 132 ± 6 |
| H9c2 | 2 | >250 |

$^a$All cytotoxicity testing was done under conditions of rapid cell division
$^b$Cells were grown on collagen coated plates for 4 or 10 d Effect on Human Bone Marrow Progenitor Cells Bone Marrow Toxicity Assay Human bone marrow cells were collected from normal healthy volunteers and the mononuclear population was separated by Ficoll-Hypaque gradient centrifugation as described previously by Sommadossi J-P, Carlisle R. "Toxicity of 3'-azido-3'-deoxythymidine and 9-(1,3-dihydroxy-2-propoxymethyl)guanine for normal human hematopoietic progenitor cells in vitro" *Antimicrobial Agents and Chemotherapy* 1987; 31:452-454; and Sommadossi J-P, Schinazi R F, Chu C K, Xie M-Y. "Comparison of cytotoxicity of the (−)- and (+)-enantiomer of 2',3'-dideoxy-3'-thiacytidine in normal human bone marrow progenitor cells" *Biochemical Pharmacology* 1992; 44:1921-1925. The culture assays for CFU-GM and BFU-E were performed using a bilayer soft agar or methylcellulose method. Drugs were diluted in tissue culture medium and filtered. After 14 to 18 days at 37° C. in a humidified atmosphere of 5% $CO_2$ in air, colonies of greater than 50 cells were counted using an inverted microscope. The results are presented as the percent inhibition of colony formation in the presence of drug compared to solvent control cultures.

Cell Protection Assay (CPA)

The assay was performed essentially as described by Baginski, S. G.; Pevear, D. C.; Seipel, M.; Sun, S. C. C.; Benetatos, C. A.; Chunduru, S. K.; Rice, C. M. and M. S. Collett "Mechanism of action of a pestivirus antiviral compound" *PNAS USA* 2000, 97(14), 7981-7986. MDBK cells (ATCC) were seeded onto 96-well culture plates (4,000 cells per well) 24 hours before use. After infection with BVDV (strain NADL, ATCC) at a multiplicity of infection (MOI) of 0.02 plaque forming units (PFU) per cell, serial dilutions of test compounds were added to both infected and uninfected cells in a final concentration of 0.5% DMSO in growth medium. Each dilution was tested in quadruplicate. Cell densities and virus inocula were adjusted to ensure continuous cell growth throughout the experiment and to achieve more than 90% virus-induced cell destruction in the untreated controls after four days post-infection. After four days, plates were fixed with 50% TCA and stained with sulforhodamine B. The optical density of the wells was read in a microplate reader at 550 nm. The 50% effective concentration ($EC_{50}$) values are defined as the compound concentration that achieved 50% reduction of cytopathic effect of the virus.

The myelosuppressive effects of certain nucleoside analogs have highlighted the need to test for potential effects of investigational drugs on the growth of human bone marrow progenitor cells in clonogenic assays. In particular, anemia and neutropenia are the most common drug-related clinical toxicities associated with the anti-HIV drug zidovudine (ZDV) or the ribavirin (RBV) component of the standard of care combination therapy used for HCV treatment. These toxicities have been modeled in an in vitro assay that employed bone marrow cells obtained from healthy volunteers (Sommadossi J-P, Carlisle R. *Antimicrob. Agents Chemother.* 1987; 31(3): 452-454). ZDV has been previously shown to directly inhibit human granulocyte-macrophage colony-forming (CFU-GM) and erythroid burst-forming (BFU-E) activity at clinically relevant concentrations of 1-2 μM in this model (Berman E, et al. *Blood* 1989; 74(4):1281-1286; Yoshida Y, Yoshida C. *AIDS Res. Hum. Retroviruses* 1990; 6(7):929-932.; Lerza R, et al. *Exp. Hematol.* 1997; 25(3):252-255; Domsife R E, Averett D R. *Antimicrob. Agents Chemother.* 1996; 40(2):514-519; Kurtzberg J, Carter S G. *Exp. Hematol.* 1990; 18(10):1094-1096; Weinberg R S, et al. *Mt. Sinai. J. Med* 1998; 65(1):5-13). Using human bone marrow clonogenic assays, the $CC_{50}$ values of mCyd in CFU-GM and BFU-E were 14.1±4.5 and 13.9±3.2 μM (see Table 5). mCyd was significantly less toxic to bone marrow cells than both ZDV and RBV (Table 5).

TABLE 5

Bone Marrow Toxicity of mCyd in Granulocyte Macrophage Progenitor and Erythrocyte Precursor Cells

| Compound | CFU-GM$^a$ $CC_{50}$ (μM) | BFU-E$^a$ $CC_{50}$ (μM) |
|---|---|---|
| mCyd | 14.1 ± 4.5 μM | 13.9 ± 3.2 |
| ZDV | 0.89 ± 0.47 | 0.35 ± 0.28 |
| RBV | 7.49 ± 2.20 | 0.99 ± 0.24 |

$^a$Data from 3 independent experiments for RBV and 5-8 independent experiments for mCyd and ZDV. All experiments were done in triplicate.

Effect on Mitochondrial Function

Antiviral nucleoside analogs approved for HIV therapy such as ZDV, stavudine (d4T), didanosine (ddI), and zalcitabine (ddC) have been occasionally associated with clinically limiting delayed toxicities such as peripheral neuropathy, myopathy, and pancreatitis (Browne M J, et al. *J. Infect. Dis.* 1993; 167(1):21-29; Fischl M A, et al. *Ann. Intern. Med.* 1993; 18(10):762-769.; Richman D D, et al. *N. Engl. J. Med* 1987; 317(4): 192-197; Yarchoan R, et al. *Lancet* 1990; 336 (8714):526-529). These clinical adverse events have been attributed by some experts to inhibition of mitochondrial function due to reduction in mitochondrial DNA (mtDNA) content and nucleoside analog incorporation into mtDNA. In addition, one particular nucleoside analog, fialuridine (1,-2'-deoxy-2'-fluoro-1-β-D-arabinofuranosyl-5-iodo-uracil; FIAU)—caused hepatic failure, pancreatitis, neuropathy, myopathy and lactic acidosis due to direct mitochondrial toxicity (McKenzie R, et al. *N Engl J Med* 1995; 333(17): 1099-1105). Drug-associated increases in lactic acid production can be considered a marker of impaired mitochondrial function or oxidative phosphorylation. (Colacino, J. M. *Antiviral Res* 1996 29(2-3): 125-39).

To assess the potential of mCyd to produce mitochondrial toxicity, several in vitro studies were conducted using the human hepatoma cell lines HepG2 or Huh7. These studies included analysis of lactic acid production, mtDNA content, and determination of changes in morphology (e.g., loss of cristae, matrix dissolution and swelling, and lipid droplet formation) of mitochondrial ultrastructure.

The effects of mCyd on mitochondria are presented in Table 6. No differences were observed in lactic acid production in mCyd-treated cells versus untreated cells at up to 50 µM mCyd in Huh7 cells or 10 µM mCyd in HepG2 cells. A modest (38%) increase in lactic acid production was seen in HepG2 cells treated with 50 µM mCyd. The significance of this finding is unclear, particularly since mCyd is unlikely to attain a plasma concentration of 50 µM in the clinic. For comparison, lactic acid production increases by 100% over control cells in cells treated with 10 µM FIAU (Cui L, Yoon, et al. *J. Clin. Invest.* 1995; 95:555-563). Exposure of HepG2 cells to mCyd for 6 or 14 days at concentrations up to 50 µM had no negative effect on mitochondrial DNA content compared to a 56 or 80% reduction in ddC-treated cells, respectively.

Following 14 days of exposure to 10 µM mCyd, the ultrastructure of HepG2 cells, and in particular mitochondria, was examined by transmission electron microscopy. No changes in cell architecture, or in mitochondrial number or morphology (including cristae), were observed in the majority of cells. In 17% of the cells, 1 to 2 mitochondria out of an average of 25 per cell appeared enlarged. Such minor changes would be unlikely to have any significant impact on mitochondrial function. ddC-treated cells showed abnormal mitochondrial morphology with loss of cristae, and the accumulation of fat droplets. (Medina, D. J., C. H. Tsai, et al. *Antimicrob. Agents Chemother.* 1994 38(8): 1824-8; Lewis W, et al. *J. Clin. Invest.* 1992; 89(4):1354-1360., Lewis, L. D., F. M. Hamzeh, et al. *Antimicrob. Agents Chemother.* 1992 36(9): 2061-5).

TABLE 6

Effect of mCyd on Hepatocyte Proliferation. Mitochondrial Function, and Morphology in HepG2 Cells

| Agent | Conc (µM) | L-Lactate (% of Control[a]) | | mtDNA/nuclear DNA (% of Control[b]) | | Electron Microscopy[c] | |
|---|---|---|---|---|---|---|---|
| | | HepG2 Cells | Huh7 Cells | 6 day Treatment | 14 day Treatment | Lipid Droplet Form. | Mito. Morphol. |
| Cont. | 0 | 100 | 100 | 100 | 100 | Negative | Normal |
| mCyd | 10 | 98.6 ± 7.3 | 98.0 ± 12.3 | 117.3 ± 17.5 | 99.7 ± 23.9 | Negative | Normal[d] |
| | 50 | 138.0 ± 8.9 | 97.1 ± 10.1 | 158.2 ± 17.5 | 83.0 ± 15.5 | nd | nd |
| ddC | 1 | nd | nd | 44.3 ± 9.3 | 19.6 ± 8.2 | nd | nd |
| | 10 | nd | nd | nd | nd | Positive | Loss of Cristae |

Effect on Human DNA Polymerases α, β, and γ

The cellular DNA polymerases are responsible for normal nuclear and mitochondrial DNA synthesis and repair. Nucleoside analog triphosphates are potential inhibitors of DNA polymerases and hence could disrupt critical cell functions. In particular, the inhibition of human polymerase γ, the enzyme responsible for mitochondrial DNA synthesis, has been linked to defects in mitochondrial function (Lewis, W., E. S. Levine, et al. *Proceedings of the National Academy of Sciences, USA* 1996 93(8): 3592-7). Experiments were undertaken to determine if mCyd-TP inhibited human DNA polymerases. As shown in Table 7 mCyd-TP was not a substrate for human DNA polymerases α, β, or γ. Even 1 mM mCyd-TP failed to inhibit these enzymes by 50% in the majority of replicate assays and $IC_{50}$ values could only be determined to be in excess of 880-1000 µM. In contrast, ddC was a potent inhibitor of all three human DNA polymerases and of polymerases β and γ in particular ($IC_{50}$s of 4.8 and 2.7 µM, respectively). Potent inhibition was also seen for the control drug, actinomycin D, a known inhibitor of DNA-dependent-DNA polymerases.

TABLE 7

Inhibition of Human Polymerases by mCyd-Triphosphate

| | $IC_{50}$ (µM) | | |
|---|---|---|---|
| | mCyd-TP[a] | ddC-TP[b] | Act. D[a] |
| Pol α | >1000 | 78 ± 23.4 | 5.8 ± 3.1 |
| Pol β | >883.3 ± 165 | 4.8 ± 1 | 7.9 ± 3 |
| Pol γ | >929.3 ± 100 | 2.7 ± 1 | 15.5 ± 4 |

[a]Mean ± S.D. from 4 data sets
[b]Mean ± S.D. from 2 data sets a. HepG2 or huh7 cells were treated with compounds for 4 days, data represent at least three independent experiments b. HepG2 cells were treated with compounds for 6 and 14 days, data represents at least three independent experiments c. HepG2 cells were treated with compounds for 14 days d. 17% cell (11 of 64) contained 1 or 2 enlarged mitochondria out of 25 in two independent experiments nd, not determined

EXAMPLE 5

In Vitro Antiviral Activity Against BVDV

Compounds can exhibit anti-flavivirus or pestivirus activity by inhibiting flavivirus or pestivirus polymerase, by inhibiting other enzymes needed in the replication cycle, or by other pathways.

Plaque Reduction Assay

For each compound the effective concentration was determined in duplicate 24-well plates by plaque reduction assays. Cell monolayers were infected with 100 PFU/well of virus. Then, serial dilutions of test compounds in MEM supplemented with 2% inactivated serum and 0.75% of methyl cellulose were added to the monolayers. Cultures were further incubated at 37° C. for 3 days, then fixed with 50% ethanol and 0.8% Crystal Violet, washed and air-dried. Then plaques were counted to determine the concentration to obtain 90% virus suppression.

Yield Reduction Assay

For each compound the concentration to obtain a 6-log reduction in viral load was determined in duplicate 24-well plates by yield reduction assays. The assay was performed as described by Baginski, S. G.; Pevear, D. C.; Seipel, M.; Sun, S. C. C.; Benetatos, C. A.; Chunduru, S. K.; Rice, C. M. and M. S. Collett "Mechanism of action of a pestivirus antiviral compound" *PNAS USA* 2000, 97(14), 7981-7986, with minor modifications. Briefly, MDBK cells were seeded onto 24-well plates (2×105 cells per well) 24 hours before infection with BVDV (NADL strain) at a multiplicity of infection (MOI) of 0.1 PFU per cell. Serial dilutions of test compounds were added to cells in a final concentration of 0.5% DMSO in growth medium. Each dilution was tested in triplicate. After three days, cell cultures (cell monolayers and supernatants) were lysed by three freeze-thaw cycles, and virus yield was quantified by plaque assay. Briefly, MDBK cells were seeded onto 6-well plates (5×105 cells per well) 24 h before use. Cells were inoculated with 0.2 mL of test lysates for 1 hour, washed and overlaid with 0.5% agarose in growth medium. After 3 days, cell monolayers were fixed with 3.5% formaldehyde and stained with 1% crystal violet (w/v in 50% ethanol) to visualize plaques. The plaques were counted to determine the concentration to obtain a 6-log reduction in viral load.

Studies on the antiviral activity of mCyd in cultured cells were conducted. The primary assay used to determine mCyd antiviral potency was a BVDV-based cell-protection assay (CPA). This assay measures the ability of mCyd to protect growing MDBK bovine kidney cells from destruction by a cytopathic NADL strain of BVDV. The cytotoxicity of the test drug on uninfected cells was measured in parallel. The antiviral activities of mCyd and ribavirin in the CPA are compared in Table 8a. mCyd effectively protected de novo-infected MDBK cells in a concentration-dependent manner with an $EC_{50}=0.67\pm0.22$ μM (Table 8a). mCyd afforded complete cytoprotection at concentrations well below the $CC_{50}$ for mCyd in this assay (38±9 μM). In the CPA, as well as in other assays described below, ribavirin showed no clear antiviral effect: significant (50% or more) cell protection was not achieved in most assays as the cytotoxicity of ribavirin overlapped and masked the protective effect. Thus, ribavirin gave a $CC_{50}$ of 4.3±0.6 μM and an $EC_{50}>4.3$ μM in the CPA.

TABLE 8a

In Vitro Activity of mCyd Against BVDV in the Cell Protection Assay

| Compound | n | $EC_{50}$, μM | $CC_{50}$, μM |
|---|---|---|---|
| mCyd | 11 | 0.67 ± 0.22 | 38 ± 9 |
| RBV | 3 | >4.3 | 4.3 ± 0.6 |

TABLE 8b $CC_{50}$ Test Results for β-D-2'-C-methyl-cytidine (Compound G), 3'-O-valinyl ester of β-D-2'-C-methyl-cytidine dihydrochloride salt (Compound M), and β-D-2'-C-methyl-uracil (Compound N)

| Compound | $CC_{50}$ | BVDV | YFV | DENV 2 | WNV | CVB-2 | Sb-1 | REO |
|---|---|---|---|---|---|---|---|---|
| G | 34 | 2.3 | 54 | 95 | 80 | 12 | 11.5 | 13 |
| M | 24 | 5.8 | 82 | >100 | 82 | 12 | 14 | 22 |
| N | >100 | 18 | 100 | > or =100 | 80 | >100 | 55 | >100 |

Note:
Cell lines utilized include MT-4 for HIV; Vero 76, African green monkey kidney cells for SARS; BHK for Bovine Viral Diarrhea Virus; Sb-1 for poliovirus Sabin type-1; CVB-2, CVB-3, CVB-4, and CVA-9 for Coxsackieviruses B-2, B-3, B-4 and A-9; and REO-1 for double-stranded RNA viruses.

TABLE 8c $CC_{50}$ and $EC_{50}$ Test Results for β-D-2'-C-methyl-cytidine (Compound G)

| Compound | $CC_{50}$ MT-4 | $CC_{50}$ Vero 76 | $CC_{50}$ BHK | $EC_{50}$ Sb-1 | $EC_{50}$ CVB-2 | $EC_{50}$ CVB-3 | $EC_{50}$ CVB-4 | $EC_{50}$ CVA-9 | $EC_{50}$ REO-1 |
|---|---|---|---|---|---|---|---|---|---|
| G | 34 | >100 | >100 | 6 | 11 | 9 | 13 | 26 | 13 |

Note:
Cell lines utilized include MT-4 for HIV; Vero 76, African green monkey kidney cells for SARS; BHK for Bovine Viral Diarrhea Virus; Sb-1 for poliovirus Sabin type-1; CVB-2, CVB-3, CVB-4, and CVA-9 for Coxsackieviruses B-2, B-3, B-4 and A-9; and REO-1 for double-stranded RNA viruses.

The overall antiviral potency of mCyd was determined against different strains of BVDV and both cytopathic (cp) and noncytopathic (ncp) biotypes in cell protection assays as well as in plaque reduction and yield reduction assays. The latter assays measure the output of infectious virus from cells and hence provide a stringent test of antiviral efficacy. The different data sets from all three assays show agreement as summarized in Table 9. The range of 50% and 90% effective inhibitory concentration ($EC_{50}$ and $EC_{90}$) values for mCyd was 0.3 to 2.8 μM and 0.87 to 4.8 μM, respectively.

In the BVDV yield reduction assay, subcytotoxic concentrations (circa 20 μM) of mCyd suppressed de novo BVDV production by up to 6 $log_{10}$, to the point where no infectious virus was detected. A 4 $log_{10}$ effective reduction in BVDV production ($EC_{4\ log\ 10}$ or $EC_{99-99}$) was attained between 6.0 and 13.9 μM mCyd. In contrast, interferon alpha 2b (IFN α2b), although active against BVDV in this assay ($EC_{50}$ 2.6 IU per ml), never gave more than 2 logs of viral reduction, even at 1000 IU per ml. Thus, the antiviral effect of mCyd against BVDV was much greater than that of IFNα2b or RBV.

EXAMPLE 6

In Vitro Antiviral Activity Against Other Positive-Strand RNA Viruses mCyd has been tested for efficacy against positive-strand RNA viruses other than BVDV. Data obtained are summarized in Table 9 and 10. Against flaviruses, mCyd showed modest activity. The composite $EC_{50}$ ranges (in μM) determined from both sites were: West Nile virus (46-97); Yellow Fever virus (9-80); and Dengue virus (59-95). For mCyd against the alpha virus, Venezuelan equine encephalitis virus, $EC_{50}$ values were 1.3-45 μM. mCyd was broadly active against picornaviruses, such as polio virus ($EC_{50}$=6 μM), coxsackie virus ($EC_{50}$=15 μM), rhinovirus types 5 and 14 ($EC_{50}$s=<0.1 and 0.6 μg/ml) and rhinovirus type 2 ($EC_{50}$ 2-10 μM). mCyd was generally inactive against all RNA and DNA viruses tested except for the positive-strand RNA viruses. mCyd was also found to have no activity against HIV in MT-4 human T lymphocyte cells or HBV in HepG2.2.15 cells.

TABLE 9

In Vitro Antiviral Activity of mCyd Against Plus-Strand RNA Viruses

| Method of Assay | Virus Type | Cell Type | n | Antiviral Efficacy (μM) | | |
|---|---|---|---|---|---|---|
| | | | | $EC_{50}$ | $EC_{90}$ | $EC_{4\ log}$ |
| Cell Protection Assay | BVDV NADL cp | MDBK | 11 | 0.67 ± 0.22 | | |
| Yield Reduction Assay | BVDV NADL cp | MDBK | 3 | 2.77 ± 1.16 | 4.8 ± 1.55 | 13.9 ± 3.07 |
| | BVDV New York-1 ncp | MDBK | 6 | 0.30 ± 0.07 | 0.87 ± 0.18 | 6.03 ± 1.41 |
| | BVDV I-NADL cp | MDBK | 1 | 0.68 | 1.73 | 8.22 |
| | BVDV I-N-dlns ncp | MDBK | 1 | 0.59 | 1.49 | 7.14 |
| Plaque Reduction Assay | BVDV NADL cp | MDBK | 3 | 2.57 ± 0.35 | 4.63 ± 0.72 | |
| Cell Protection Assay | West Nile Virus | BHK | 3 | 63-97 | | |
| Cell Protection Assay | Yellow Fever Virus 17D | BHK | 1 | 60-80 | | |
| | DENV-2 | BHK | 2 | 95 | | |
| Cell Protection Assay | DENV-4 | BHK | 1 | 59 | | |
| Plaque Reduction Assay | Polio Virus Sb-1 | VERO | 1 | 6 | | |
| Plaque Reduction Assay | Coxsackie Virus B2 | VERO | 1 | 15 | | | cp, cytopathic virus; ncp noncytopathic virus
1-NADL cp and 1-N-dlns ncp represent recombinant BVDV viruses

TABLE 10

In Vitro Antiviral Activity, Selectivity, and Cytotoxicity of mCyd

| Virus (Cell line)[a] | $EC_{50}$[b] (μM) | $CC_{50}$[c] (μM) |
|---|---|---|
| WNV (Vero) | 46 | 114-124 |
| YFV (Vero) | 9-30 | 150->200 |
| VEE (Veto) | 1.3-45 | >200 |
| HSV-1 (HFF)[d] | >100 | >100 |
| HSV-2 (HFF)[d] | >100 | >100 |
| VZV (HFF)[d] | >20 | 67.8 |
| EBV (Daudi)[d] | 25.5 | >50 |
| HCMV (HFF)[d] | 9.9-15.6 | 67-73 |
| MCMV (MEF) | >0.8 | 2.4 |
| Influenza A/H1N1 (MDCK) | >200 | >200 |
| Influenza A/H3N2 (MDCK) | >20 | 45-65 |
| Influenza B (MDCK) | >200 | 55-140 |
| Adenovirus type 1 (A549) | >200 | >200 |
| Parainfluenza type 3 (MA-104) | >200 | >200 |
| Rhinovirus type 2 (KB) | 2-10 | >200 |
| Rhinovirus type 5 (KB)[d] | 0.6 | 20-30 |
| Rhinovirus type 14 (HeLa-Ohio)[d] | <0.1 | 20->100 |
| RSV type A (MA-104) | >200 | 200 |
| Punta Toro A (LLC-MK2) | >200 | >200 |

[a]HFF, human foreskin fibroblast; Daudi, Burkitt's B-cell lymphoma; MDCK, canine kidney cells; CV-1, African green monkey kidney cells; KB, human nasopharyngeal carcinoma; MA-104, Rhesus monkey kidney cells; LLC-MK2, Rhesus monkey kidney cells; A549, Human lung carcinoma cells; MEF, mouse embryo fibroblast; Vero, African green monkey kidney cells; HeLa, human cervical adenocarcinoma cells.
[b]$EC_{50}$ = 50% effective concentration.
[c]$CC_{50}$ = 50% cytotoxic concentration.
[d]Result presented in μg/mL rather than μM.

EXAMPLE 7

Multiplicity of Infection (MOI) and Antiviral Efficacy

The cell protection assay format was used to test the effect of increasing the amount of BVDV virus on the $EC_{50}$ of mCyd. Increasing the multiplicity of infection (MOI) of BVDV in this assay from 0.04 to 0.16, caused the $EC_{50}$ of mCyd to increase linearly from 0.5 µM to approximately 2.2 µM.

EXAMPLE 8

Viral Rebound in mCyd Treated Cells

The effect of discontinuing treatment with mCyd was tested in MDBK cells persistently infected with a noncytopathic strain (strain I-N-dIns) of BVDV. Upon passaging in cell culture, these cells continuously produce anywhere from $10^6$ to >$10^7$ infectious virus particles per ml of media. This virus can be measured by adding culture supernatants from treated MDBK (BVDV) cells to uninfected MDBK cells and counting the number of resultant viral foci after disclosure by immunostaining with a BVDV-specific antibody. Treatment of a persistently infected cell line with 4 µM mCyd for one cell passage (3 days) reduced the BVDV titer by approximately 3 $\log_{10}$ from pretreatment and control cell levels of just under $10^7$ infectious units per ml. At this point, mCyd treatment was discontinued. Within a single passage, BVDV titers rebounded to untreated control levels of just over $10^7$ infectious units per ml.

EXAMPLE 9

Mechanism of Action

In standard BVDV CPA assays, mCyd treatment results in a marked increase in total cellular RNA content as cells grow, protected from the cytopathic effects of BVDV. This is coupled with a marked decrease in the production of BVDV RNA due to mCyd. Conversely, in the absence of mCyd, total cellular RNA actually decreases as BVDV RNA rises due to the destruction of the cells by the cytopathic virus. To further test the effect of mCyd on viral and cellular RNAs, the accumulation of intracellular BVDV RNA was monitored in MDBK cells 18-hours post infection (after approximately one cycle of virus replication) using Real Time RT-PCR. In parallel, a cellular housekeeping ribosomal protein mRNA (rig S15 mRNA) was also quantitated by RT-PCR using specific primers. The results showed that mCyd dramatically reduced BVDV RNA levels in de novo-infected MDBK cells with an $EC_{50}$ of 1.7 µM and an $EC_{90}$ of 2.3 µM. The maximum viral RNA reduction was 4 $\log_{10}$ at the highest inhibitor concentration tested (125 µM). No effect on the level of the rig S15 cellular mRNA control was observed. Together, the preceding findings suggest that mCyd inhibited BVDV by specifically interfering with viral genome RNA synthesis without impacting cellular RNA content. This idea is further supported by the observation (Table 4a) that inhibition of RNA synthesis as measured by [$^3$H]-uridine uptake in HepG2 cells requires high concentrations of mCyd $EC_{50}$=186 µM).

Figure 2:
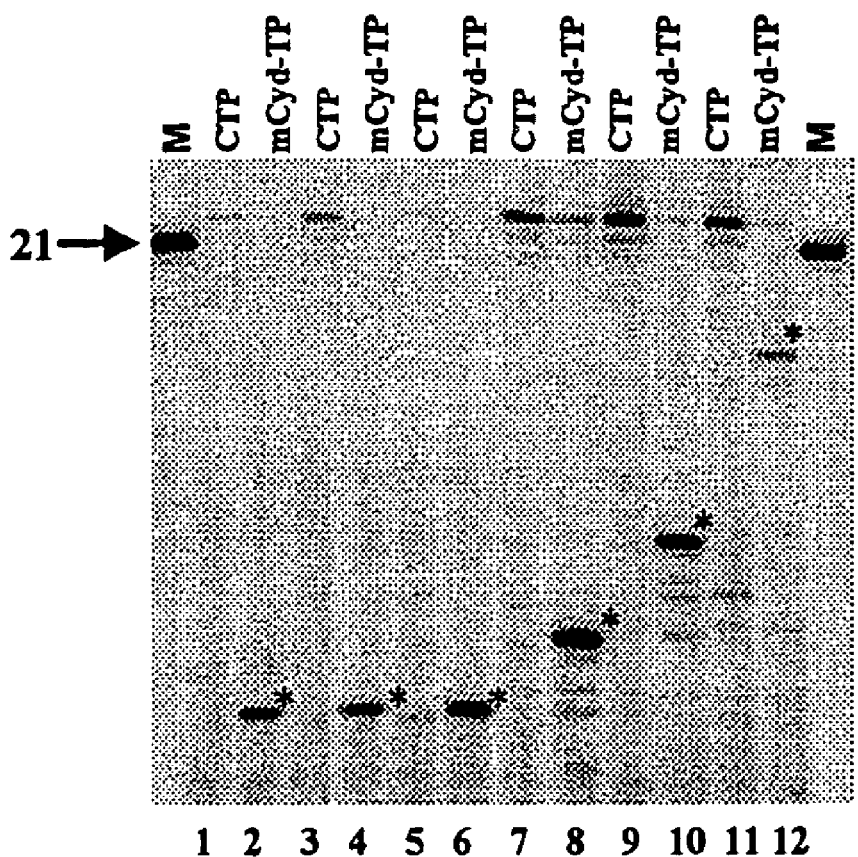
FIG. 2 is a photocopy of a gel illustrating the site-specific chain termination of in vitro RNA synthesis by β-D-2'-C-methyl-ribofuranosyl cytidine triphosphate at specified guanine residues in RNA templates, as described in Example 9.

In in vitro studies using purified BVDV NS5B RNA-dependent RNA polymerase (Kao, C. C., A. M. Del Vecchio, et al. (1999). "De novo initiation of RNA synthesis by a recombinant flaviviridae RNA-dependent RNA polymerase." *Virology* 253(1): 1-7) and synthetic RNA templates, mCyd-TP inhibited RNA synthesis with an $IC_{50}$ of 0.74 µM and was a competitive inhibitor of BVDV NS5B RNA-dependent RNA polymerase with respect to the natural CTP substrate. The inhibition constant ($K_i$) for mCyd-TP was 0.16 µM and the Michaelis-Menten constant ($K_m$) for CTP was 0.03 µM. Inhibition of RNA synthesis by mCyd-TP required the presence of a cognate G residue in the RNA template. The effect of mCyd-TP on RNA synthesis in the absence of CTP was investigated in more detail using a series of short (21 mer) synthetic RNA templates containing a single G residue, which was moved progressively along the template. Analysis of the newly synthesized transcripts generated from these templates in the presence of mCyd-TP revealed that RNA elongation continued only as far as the G residue, then stopped (FIG. 2). In templates containing more than one G residue, RNA synthesis stopped at the first G residue encountered by the polymerase. These data strongly suggest that m-Cyd-TP is acting as a non-obligate chain terminator. The mechanism of this apparent chain termination is under further investigation.

EXAMPLE 10

Eradication of a Persistent BVDV Infection

Figure 3:
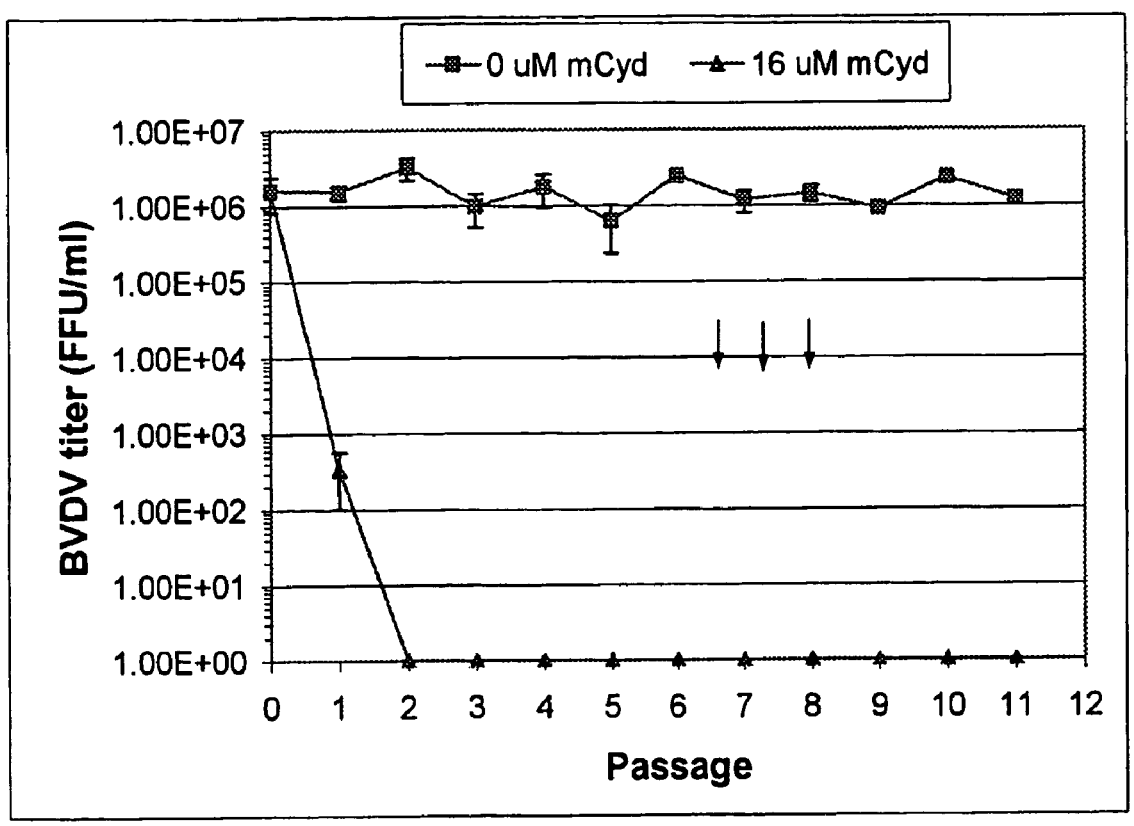
FIG. 3 is a graph of the titer of bovine viral diarrhea virus (BVDV) over number of passages of BVDV infected MDBK cells, indicating eradication of a persistent BVDV infection by prolonged treatment with β-D-2'C-methyl-ribofuranosyl cytidine (16 uM) as described in Example 10. Arrows indicate points at which a portion of cells were withdrawn from drug treatment.

The ability of mCyd to eradicate a viral infection was tested in MDBK cells persistently infected with a noncytopathic strain of BVDV (strain I-N-dIns). (Vassilev, V. B. and R. O. Donis *Virus Res* 2000 69(2): 95-107.) Compared to untreated cells, treatment of persistently infected cells with 16 µM mCyd reduced virus production from more than 6 logs of virus per ml to undetectable levels within two cell passages (3 to 4 days per passage). No further virus production was seen upon continued treatment with mCyd through passage 12. At passages 8, 9 and 10 (arrows, FIG. 3), a portion of cells was cultured for two further passages in the absence of drug to give enough time for mCyd-TP to decay and virus replication to resume. The culture media from the cells were repeatedly tested for the re-emergence of virus by adding culture supernatants from treated MDBK (BVDV) cells to uninfected MDBK cells and counting the resultant viral foci after disclosure by immunostaining with a BVDV-specific antibody. Although this assay can detect a single virus particle, no virus emerged from the cells post drug treatment. Thus, treatment with mCyd for 8 or more passages was sufficient to eliminate virus from the persistently infected cells.

EXAMPLE 11

Combination Studies with Interferon Alpha 2B

Figure 4:
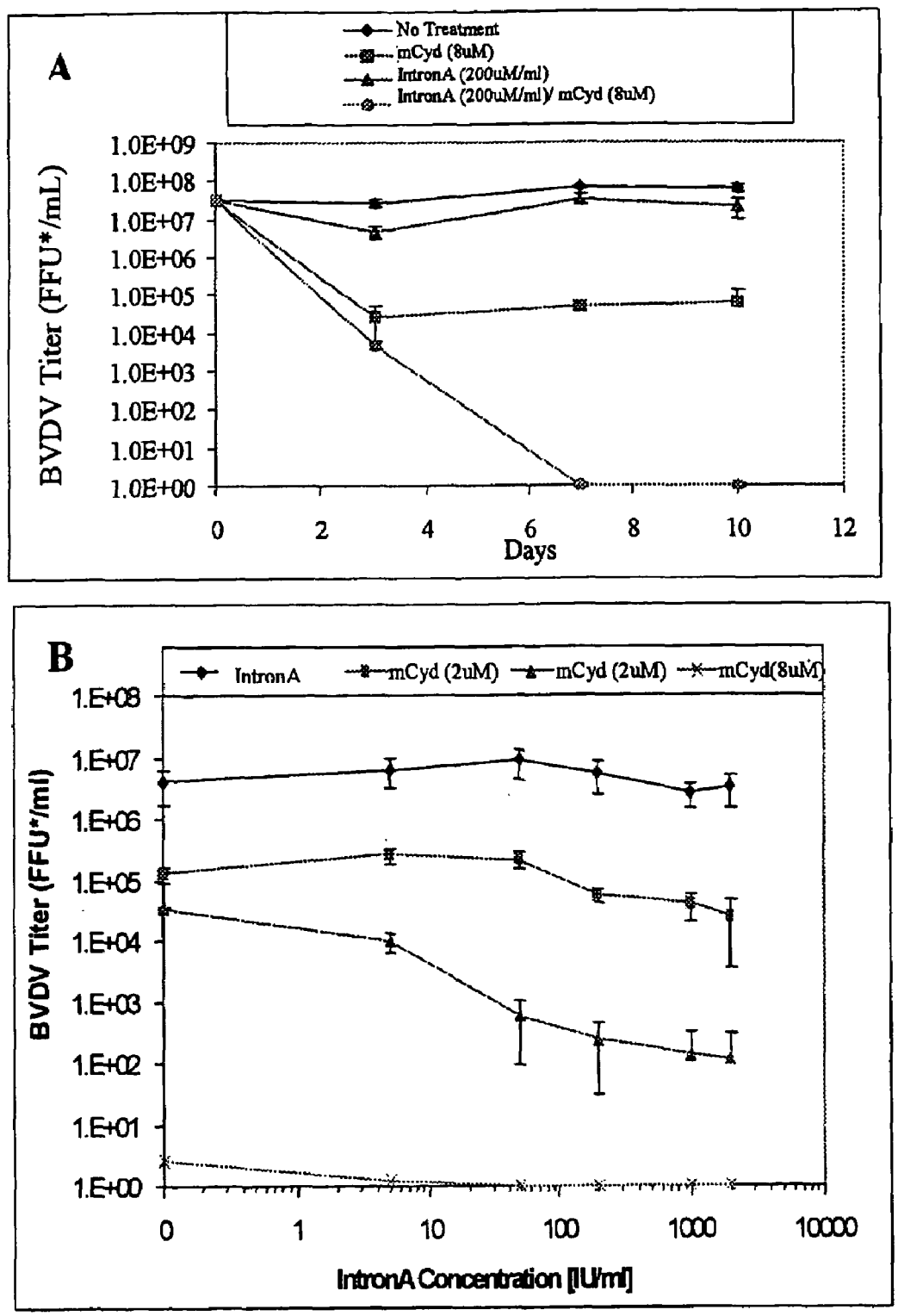
FIGS. 4a and 4b are graphs of the concentration of bovine viral diarrhea virus (BVDV) in MDBK cells persistently infected with the virus, as described in Example 11. These graphs indicate the synergy between β-D-2'-C-methyl-ribofuranosyl cytidine and interferon alpha 2b (IntronA) in reducing the viral titer.

The first study, performed in MDBK cells persistently infected with the New York-1 (NY-1) strain of BVDV, compared the effect of monotherapy with either mCyd (8 µM) or interferon alpha 2b (200 IU/ml), or the two drugs in combination (FIG. 4A). In this experiment, 8 µM mCyd alone reduced viral titers by approximately 3.5 $\log_{10}$ after one passage to a level that was maintained for two more passages. Interferon alpha 2b alone was essentially inactive against persistent BVDV infection (approximately 0.1 $\log_{10}$ reduction in virus titer) despite being active against de novo BVDV infection. However, the combination of mCyd plus interferon alpha 2b reduced virus to undetectable levels by the second passage and clearly showed better efficacy to either monotherapy.

In a follow up study (FIG. 4B) of MDBK cells persistently infected with the I-N-dIns noncytopathic strain of BVDV, mCyd was supplied at fixed doses of 0, 2, 4 and 8 µM, while interferon alpha 2b was titrated from 0 to 2,000 IU per ml. Again, interferon alpha 2b was essentially inactive (0.1 log reduction in viral titer), while mCyd alone inhibited BVDV (strain I-N-dIns) propagation in a dose-dependent manner. mCyd at 8 µM reduced virus production by 6.2 $\log_{10}$, to almost background levels.

EXAMPLE 12

Resistance Development

Figure 5:
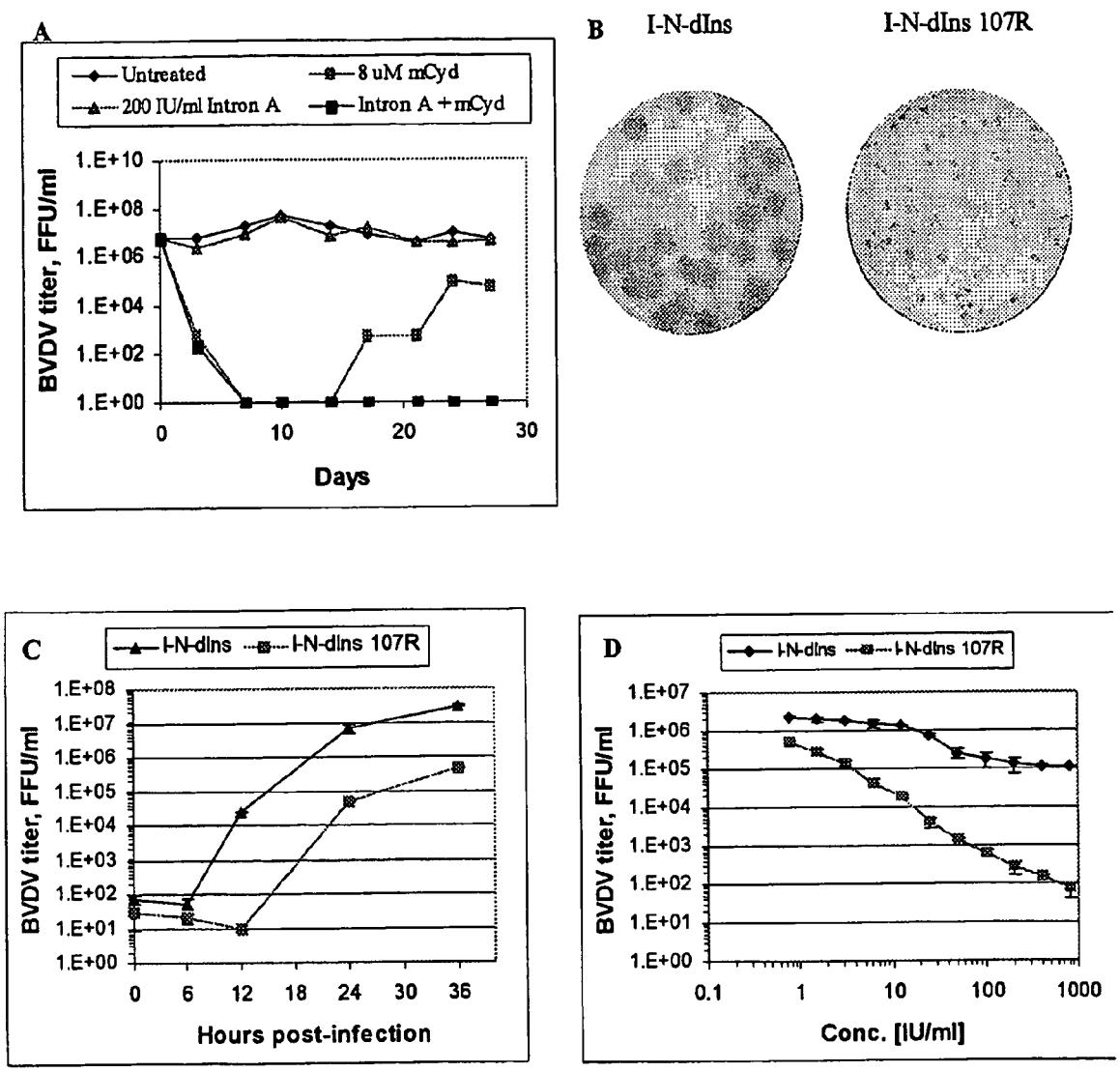
FIGS. 5a-d illustrate the results of experiments studying the development of resistance to β-D-2'-C-methyl-ribofuranosyl cytidine treated MDBK cells, infected with bovine viral diarrhea virus (BVDV), as described in Example 12.

In early cell culture studies, repeated passaging of a cytopathic strain of BVDV in MDBK cells in the presence of mCyd failed to generate resistant mutants, suggesting that the isolation of mCyd-resistant BVDV mutants is difficult. However, studies in cell lines persistently infected with noncytopathic forms of BVDV led to the selection of resistant virus upon relatively prolonged treatment with mCyd at suboptimal therapeutic concentrations of drug (2 to 8 µM, depending on the experiment). In the representative experiment shown in FIG. 5A, the virus was no longer detectable after two passages in the presence of 8 µM mCyd, but re-emerged by passage 6. The lower titer of the re-emergent virus is apparent from the data: resistant virus typically has a 10 fold or more lower titer than the wild-type virus and is easily suppressed by co-therapy with IntronA (FIG. 5A). The phenotype of the virus that re-emerged was remarkably different from the initial wild-type virus: as shown in FIG. 5B, it yielded much smaller foci (typically, 3 to 10 times smaller in diameter then those of the wild-type virus). This phenotype did not change after prolonged passaging in culture in the presence of the inhibitor (at least 72 days), however, it quickly reverted to the wild-type phenotype (large foci) after the discontinuation of the treatment.

RT-PCR sequencing of the resistant mutant was used to identify the mutation responsible for resistance. Sequencing efforts were focused on the NS5B RNA-dependent RNA polymerase region of BVDV, which was assumed to be the likely target for a nucleoside inhibitor. A specific S405T amino-acid substitution was identified at the start of the highly conserved B domain motif of the polymerase. The B domain is part of the polymerase active site and is thought to be involved in nucleoside binding (Lesburg, C. A., M. B. Cable, et al. *Nature Structural Biology* 1999 6(10): 937-43). Resistance to nucleosides has been mapped to this domain for other viruses such as HBV (Ono et al, *J Clin Invest.* 2001 February; 107(4):449-55). To confirm that this mutation was responsible for the observed resistance, the mutation was reintroduced into the backbone of a recombinant molecular clone of BVDV. The resulting clone was indistinguishable in phenotypic properties from the isolated mutant virus, confirming that the S405T mutation is responsible for resistance and that the NS5B RNA-dependent RNA polymerase is the molecular target for mCyd. The highly conserved nature of this motif at the nucleotide sequence (Lai, V. C., C. C. Kao, et al. *J Virol* 1999 73(12): 10129-36) and structural level among positive-strand RNA viruses (including HCV) allows a prediction that the equivalent mutation in the HCV NS5B RNA-dependent RNA polymerase would likely be S282T.

S405T mutant BVDV was refractory to mCyd up to the highest concentrations that could be tested ($EC_{50}>32$ µM), but was also significantly impaired in viability compared to wild-type virus. As noted above, the S405T mutant exhibited a 1-2 $\log_{10}$ lower titer than wild-type BVDV and produced much smaller viral plaques. In addition, the mutant virus showed a marked reduction in the rate of a single cycle of replication (>1000-fold lower virus titer at 12 h), and accumulated to about 100 fold lower levels than the wild-type virus even after 36 h of replication (FIG. 5C). The virus also quickly reverted to wild-type virus upon drug withdrawal. Finally, the mutant was also more sensitive (~40 fold) to treatment with IFN alpha 2b than wild-type as shown in FIG. 5D.

A second, additional mutation, C446S, was observed upon further passaging of the S405T mutant virus in the presence of drug. This mutation occurs immediately prior to the essential GDD motif in the C domain of BVDV NS5B RNA-dependent RNA polymerase. Preliminary studies suggest that a virus bearing both mutations does not replicate significantly better than the S405T mutant, hence the contribution of this mutation to viral fitness remains unclear.

EXAMPLE 13

In Vivo Antiviral Activity of Val-mCyd in an Animal Efficacy Model

Chimpanzees chronically infected with HCV are the most widely accepted animal model of HCV infection in human patients (Lanford, R. E., C. Bigger, et al. *Ilar J* 2001 42(2): 117-26; Grakoui, A., H. L. Hanson, et al. *Hepatology* 2001 33(3): 489-95). A single in vivo study of the oral administration of val-mCyd in the chimpanzee model of chronic hepatitis C virus infection has been conducted.

HCV genotyping on the five chimpanzees was performed by the Southwest Foundation Primate Center as part of their mandated internal Health and Maintenance Program, designed to ascertain the disease status of all animals in the facility to identify potential safety hazards to employees. The five chimpanzees used in this study exhibited a high HCV titer in a genotyping RT PCR assay that distinguishes genotype 1 HCV from all other genotypes, but does not distinguish genotype 1a from 1b. This indicated that the chimpanzees used in this study were infected with genotype 1 HCV (HCV-1).

TABLE 11

Summary of Val-mCyd In Vivo Activity Study in the Chimpanzee Model of Chronic HCV Infection

| Study Description | Species (N) | Val-mCyd Doses (mg/kg) (n) | Frequency/Route of Administration | Study Endpoints |
|---|---|---|---|---|
| One-week antiviral activity of mCyd in chronically hepatitis C virus (genotype 1)-infected chimpanzees | Chimpanzee (5) | 10 and 20 (2 each) [equivalent to 8.3 and 16.6 mpk of freebase], and vehicle control (1) | QD ×7 days (PO) | Serum HCV RNA, serum chemistries, CBCs, general well being, and clinical observations |

Seven-Day Antiviral Activity Study in the Chimpanzee Model of Chronic Hepatitis C Virus Infection Four chimpanzees (2 animals per dose group at 10 mg/kg/day or 20 mg/kg/day) received val-mCyd dihydrochloride, freshly dissolved in a flavorful fruit drink vehicle. These doses were equivalent to 8.3 and 16.6 mg/kg/day of the val-mCyd free base, respectively. A fifth animal dosed with vehicle alone provided a placebo control. The study design included three pretreatment bleeds to establish the baseline fluctuation of viral load and three bleeds during the one week of treatment (on days 2, 5 and 7 of therapy) to evaluate antiviral efficacy. The analysis was completed at the end of the one-week dosing period, with no further follow up.

HCV RNA Determination

Serum levels of HCV RNA throughout the study were determined independently by two clinical hospital laboratories. HCV RNA was assayed using a quantitative RT-PCR nucleic acid amplification test (Roche Amplicor HCV Monitor Test, version 2.0). This assay has a lower limit of detection (LLOD) of 600 IU/mL and a linear range of 600-850,000 IU/mL.

Figure 6:
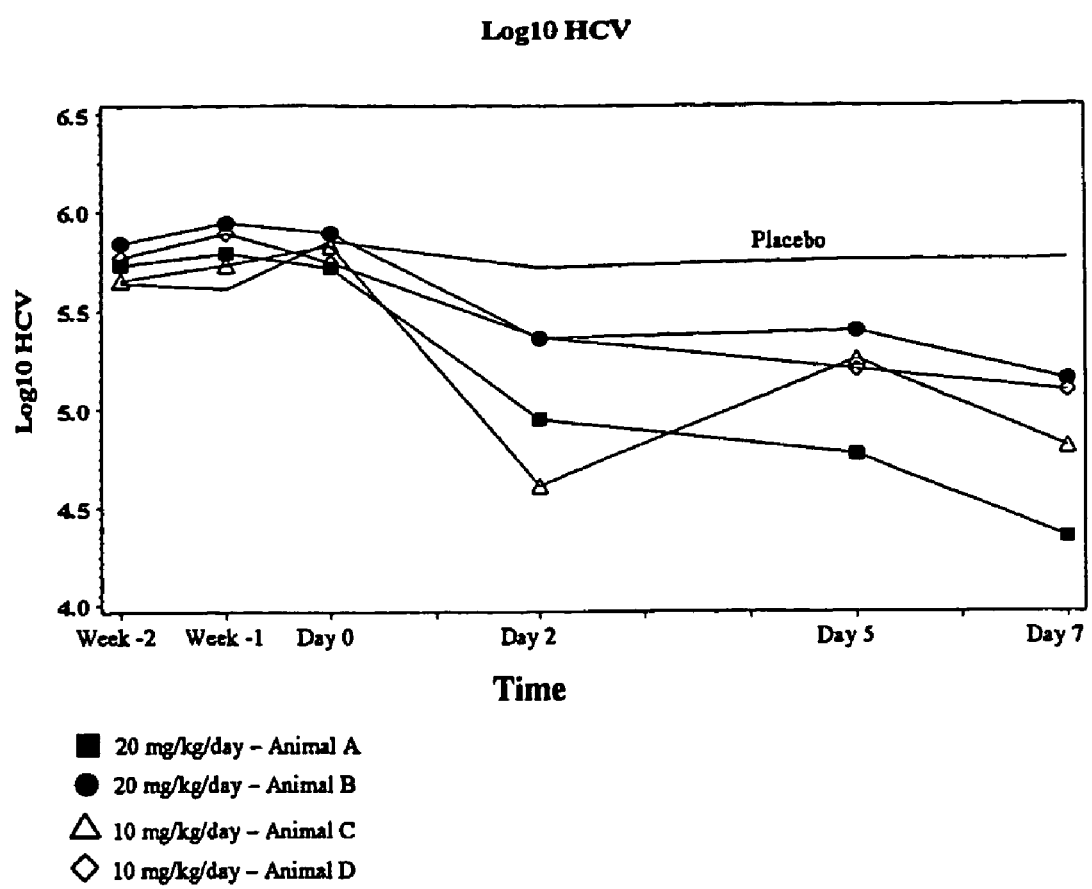
FIG. 6 is a graph of the concentration of hepatitis C virus ($Log_{10}$) in individual chimpanzees over days of treatment with β-D-2'-C-methyl-ribofuranosyl cytidine-3'-O-L-valine ester as described in Example 13.
Figure 7:
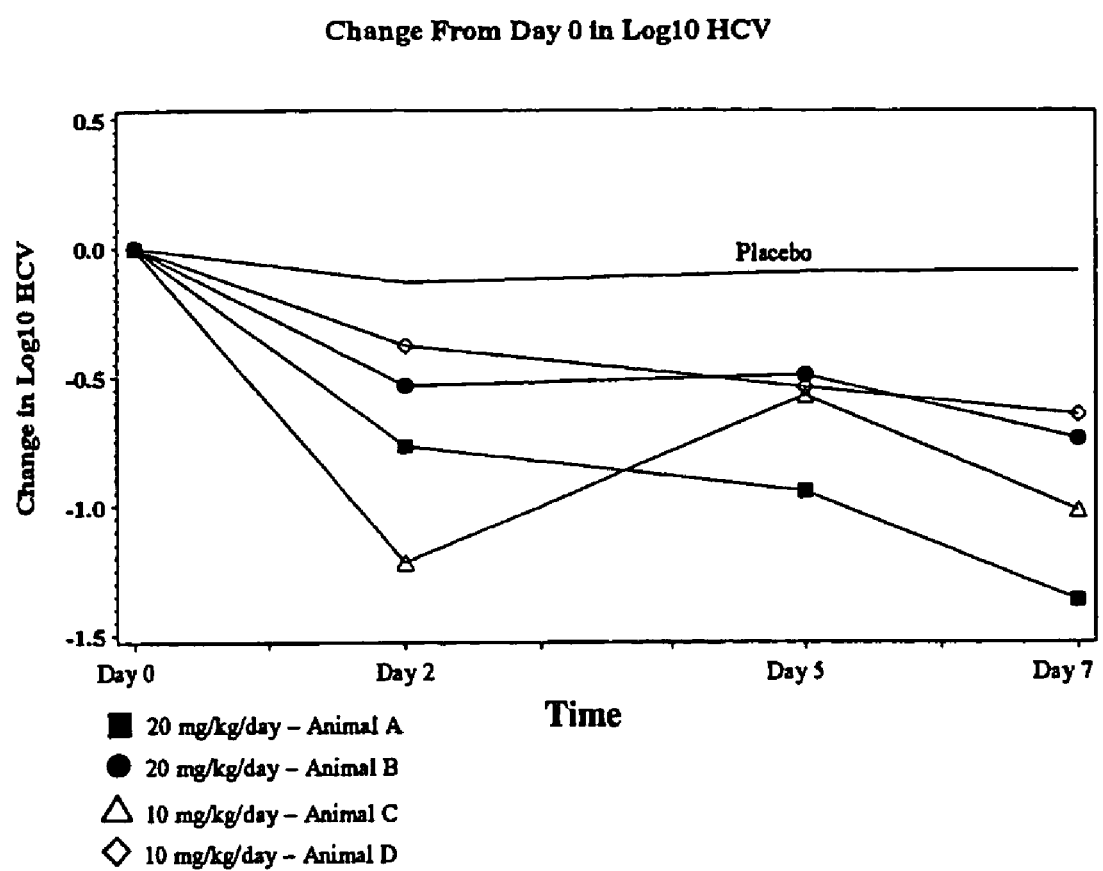
FIG. 7 is a graph of the concentration of hepatitis C virus in individual chimpanzees over days of treatment with β-D-2'-C-methyl-ribofuranosyl cytidine-3'-O-L-valine ester as compared to baseline, as described in Example 13.

To aid in interpretation of the viral load declines seen during therapy, emphasis was placed on determining (i) the extent of fluctuations in baseline HCV viral load in individual animals, and (ii) the inherent variability and reproducibility of the HCV viral load assay. To address these issues, full viral load data sets obtained from the two laboratories were compared. The results from both sites were found to be closely comparable and affirmed both the stability of the pretreatment HCV viral loads as well as the reliability of the HCV Roche Amplicor assay. To present the most balanced view of the study, the mean values derived by combining both data sets were used to generate the results presented in FIGS. 6 and 7. FIG. 6 presents the averaged data for dose cohorts, while FIG. 7 presents the individual animal data. The changes in viral load from baseline seen during therapy for each animal at each site are also summarized in Table 12.

The HCV viral load analysis from the two sites revealed that pretreatment HCV viral loads were (i) very similar among all five animals and all 3 dose groups, and (ii) very stable over the 3-week pretreatment period. The mean pretreatment $\log_{10}$ viral load and standard deviations among the five individual animals were 5.8±0.1 (site 1) and 5.6±0.1 (site 2). These data indicated that the c.v. (coefficient of variance) of the assay is only around 2% at both sites. The largest fluctuation in HCV viral load seen in any animal during pretreatment was approximately 0.3 $\log_{10}$.

As seen in FIGS. 6 and 7, once a day oral delivery of val-mCyd produced a rapid antiviral effect that was not seen for the placebo animal, nor during the pretreatment period. Viral titers were substantially reduced from baseline after two days of therapy for all animals receiving val-mCyd, and tended to fall further under continued therapy in the two treatment arms. By the end of treatment (day 7), the mean reductions from baseline HCV viral load were 0.83 $\log_{10}$ and 1.05 $\log_{10}$ for the 8.3 and 16.6 mg/kg/day dose groups, respectively. The titer of the placebo animal remained essentially unchanged from baseline during the therapy period.

An analysis of the data from the two quantification sites on the changes in baseline HCV viral load in response to therapy is presented in Table 12. Overall, the two data sets agree well, confirming the reliability of the assay. With the exception of animal 501, the difference in viral load between the two sites was generally 0.3 $\log_{10}$ or less, similar to the fluctuation observed during the pretreatment period. For animal 501, the discrepancy was closer to 0.5 $\log_{10}$. The viral load drop seen in response to therapy varied from 0.436 (animal 501, site 1) to 1.514 $\log_{10}$ (animal 497, site 2). The latter corresponds to a change in HCV viral load from 535,000 (pretreatment) to 16,500 (day 7) genomes per ml.

TABLE 12

Summary of Changes in Baseline $\log_{10}$ HCV RNA Viral Load During Therapy

| Dose (mpk) | Animal ID | Site | Day 2 | Day 5 | Day 7 |
|---|---|---|---|---|---|
| 0 | 499 | 1 | −0.00041 | −0.11518 | 0.14085 |
|  |  | 2 | −0.06604 | 0.10612 | −0.16273 |

TABLE 12-continued

Summary of Changes in Baseline $\log_{10}$ HCV RNA Viral Load During Therapy

| Dose (mpk) | Animal ID | Site | Day 2 | Day 5 | Day 7 |
|---|---|---|---|---|---|
| 8.3 | 500 | 1 | −1.15634 | −0.40385 | −0.80507 |
|  |  | 2 | −1.07902 | −0.55027 | −1.06259 |
| 8.3 | 501 | 1 | −0.25180 | −0.36179 | −0.43610 |
|  |  | 2 | −0.45201 | −0.71254 | −0.90034 |
| 16.6 | 497 | 1 | −0.72148 | −0.90704 | −1.27723 |
|  |  | 2 | −0.85561 | −1.01993 | −1.51351 |
| 16.6 | 498 | 1 | −0.29472 | −0.28139 | −0.60304 |
|  |  | 2 | −0.65846 | −0.55966 | −0.69138 |

Exposure of Chimpanzees to mCyd

Limited HPLC analyses were performed to determine the concentration of mCyd attained in the sera of chimpanzees following dosing with val-mCyd. In sera drawn 1 to 2 hours post dose on days 2 and 5 of dosing, mCyd levels were typically between 2.9 and 12.1 μM (750 and 3100 ng/mL, respectively) in treated animals. No mCyd was detected in pretreatment sera or in the placebo control sera. Within 24 hours of the final dose, serum levels of mCyd had fallen to 0.2 to 0.4 μM (50 and 100 ng/mL, respectively). No mUrd was detected in any sera samples although the methodology used has a lower limit of quantification of 0.4 μM (100 ng/mL) for mUrd.

Safety of mCyd in the Chimpanzee Model of Chronic HCV Infection

Chimpanzees were monitored by trained veterinarians throughout the study for weight loss, temperature, appetite, and general well being, as well as for blood chemistry profile and CBCs. No adverse events due to drug were noted. The drug appeared to be well tolerated by all four treated animals. All five animals lost some weight during the study and showed some aspartate aminotransferase (AST) elevations, but these are normal occurrences related to sedation procedures used, rather than study drug. A single animal experienced an alanine aminotransferase (ALT) flare in the pretreatment period prior to the start of dosing, but the ALT levels diminished during treatment. Thus, this isolated ALT event was not attributable to drug.

EXAMPLE 14

In Vitro Metabolism

Figure 8:
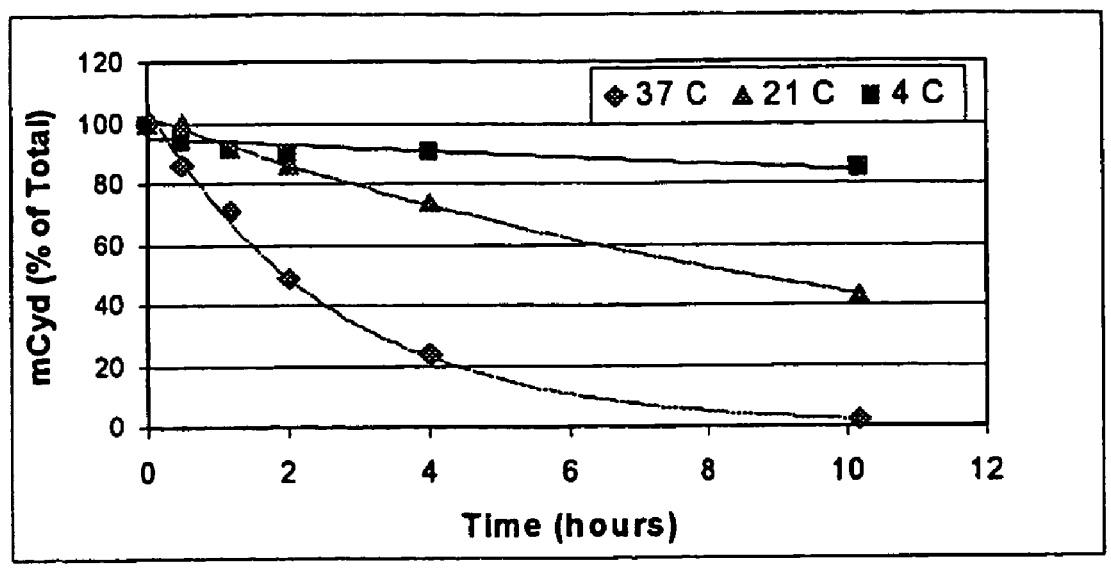
FIG. 8 is a graph of percent of total β-D-2'-C-methyl-ribofuranosyl cytidine-3'-O-L-valine ester remaining in samples over time after incubation of the drug in human plasma at 4° C., 21° C., and 37° C., as described in Example 14.

Studies were conducted to determine the stability of val-mCyd and mCyd in human plasma. Val-mCyd was incubated in human plasma at 0, 21 or 37° C. and samples analyzed at various time points up to 10 hours (FIG. 8). At 37° C., val-mCyd was effectively converted to mCyd, with only 2% of the input val-mCyd remaining after 10 hours. The in vitro half-life of val-mCyd in human plasma at 37° C. was 1.81 hours. In studies of the in vitro stability of mCyd in human plasma, or upon treatment with a crude preparation enriched in human cytidine/deoxycytidine deaminase enzymes, mCyd remained essentially unchanged and no deamination to the uridine derivative of mCyd (mUrd) occurred after incubation at 37° C. Only in rhesus and cynomologus monkey plasma was limited deamination observed. Incubation of mCyd at 37° C. in cynomologus monkey plasma yielded 6.7 and 13.0% of mUrd deamination product after 24 and 48 hours, respectively, under conditions where control cytidine analogs were extensively deaminated.

In addition to the TP derivatives of mCyd and mUrd, minor amounts of mCyd-5'-diphosphate, mCyd-DP, roughly 10% the amount of the corresponding TP, were seen in all three cell types. Lesser amounts of mUrd-DP were detected only in two cell types, primary human hepatocytes and MDBK cells. No monophosphate (MP) metabolites were detected in any cell type. There was no trace of any intracellular mUrd and no evidence for the formation of liponucleotide metabolites such as the 5'-diphosphocholine species seen upon the cellular metabolism of other cytidine analogs.

FIG. 9 shows the decay profile of mCyd-TP determined following exposure of HepG2 cells to 10 μM [$^3$M]-mCyd for 24 hours. The apparent intracellular half-life of the mCyd-TP was 13.9±2.2 hours in HepG2 cells and 7.6±0.6 hours in MDBK cells: the data were not suitable for calculating the half life of mUrd-TP. The long half life of mCyd-TP in human hepatoma cells supported the notion of once-a-day dosing for val-mCyd in clinical trials for HCV therapy. Phosphorylation of mCyd occurred in a dose-dependent manner up to 50 μM drug in all three cell types, as shown for HepG2 cells in FIG. 9C. Other than the specific differences noted above, the phosphorylation pattern detected in primary human hepatocytes was qualitatively similar to that obtained using HepG2 or MDBK cells.

Contribution of mUrd

In addition to the intracellular active moiety, mCyd-TP, cells from different species have been shown to produce variable and lesser amounts of a second triphosphate, mUrd-TP, via deamination of intracellular mCyd species. The activity of mUrd-TP against BVDV NS5B RNA-dependent RNA polymerase has not been tested to date but is planned. To date, data from exploratory cell culture studies on the antiviral efficacy and cytotoxicity of mUrd suggest that mUrd (a) is about 10-fold less potent than mCyd against BVDV; (b) has essentially no antiviral activity against a wide spectrum of other viruses; and (c) is negative when tested at high concentrations in a variety of cytotoxicity tests (including bone marrow assays, mitochondrial function assays and incorporation into cellular nucleic acid). Based on these results, it appeared that the contribution of mUrd to the overall antiviral activity or cytotoxicity profile of mCyd is likely to be minor. Extensive toxicology coverage for the mUrd metabolite of mCyd exists from subchronic studies conducted with val-mCyd in the monkey.

EXAMPLE 15

Cellular Pathways for Metabolic Activation

The nature of the enzyme responsible for the phosphorylation of mCyd was investigated in substrate competition experiments. Cytidine (Cyd) is a natural substrate of cytosolic uridine-cytidine kinase (UCK), the pyrimidine salvage enzyme responsible for conversion of Cyd to Cyd-5'-monophosphate (CMP). The intracellular phosphorylation of mCyd to mCyd-TP was reduced in the presence of cytidine or uridine in a dose-dependent fashion with $EC_{50}$ values of 19.17±4.67 μM for cytidine and 20.92±7.10 μM for uridine. In contrast, deoxycytidine, a substrate for the enzyme deoxycytidine kinase (dCK), had little effect on the formation of mCyd-TP with an $EC_{50}$>100 mM. The inhibition of mCyd phosphorylation by both cytidine and uridine, but not deoxycytidine, suggests that mCyd is phosphorylated by the pyrimidine salvage enzyme, uridine-cytidine kinase (Van Rompay, A. R., A. Norda, et al. *Mol Pharmacol* 2001 59(5): 1181-6). Further studies are required to confirm the proposed role of this kinase in the activation of mCyd.

EXAMPLE 16

Pathways for the Cellular Biosynthesis of mUrd-TP

As outlined above, mUrd-TP is a minor metabolite arising to varying extents in cells from different species. mUrd does not originate via extracellular deamination of mCyd since mUrd was not seen in the cell medium which also lacks any deamination activities. The cellular metabolism data are consistent with the idea that mUrd-TP arises via the biotransformation of intracellular mCyd species. Consideration of the known ribonucleoside metabolic pathways suggests that the most likely routes involve deamination of one of two mCyd species by two distinct deamination enzymes: either mCyd-MP by a cytidylate deaminase (such as deoxycytidylate deaminase, dCMPD), or of mCyd by cytidine deaminase (CD). Further phosphorylation steps lead to mUrd-TP. These possibilities are under further investigation.

EXAMPLE 17

Clinical Evaluation of Val-mCyd

Patients who met eligibility criteria were randomized into the study at Baseline (Day 1), the first day of study drug administration. Each dosing cohort was 12 patients, randomized in a 10:2 ratio to treatment with drug or matching placebo. Patients visited the study center for protocol evaluations on Days 1, 2, 4, 8, 11, and 15. After Day 15, study drug was stopped. Thereafter, patients attended follow-up visits on Days 16, 17, 22, and 29. Pharmacokinetic sampling was performed on the first and last days of treatment (Day 1 and Day 15) on all patients, under fasting conditions.

The antiviral effect of val-mCyd was assessed by (i) the proportion of patients with a $\geq 1.0 \log_{10}$ decrease from baseline in HCV RNA level at Day 15, (ii) the time to a $\geq 1.0 \log_{10}$ decrease in serum HCV RNA level, (iii) the change in HCV RNA level from Day 1 to Day 15, (iv) the change in HCV RNA level from Day 1 to Day 29, (v) the proportion of patients who experience return to baseline in serum HCV RNA level by Day 29, and (vi) the relationship of val-mCyd dose to HCV RNA change from Day 1 to Day 15.

Clinical Pharmacokinetics of mCyd after Oral Administration of Escalating Doses of Val-mCyd Pharmacokinetics were evaluated over a period of 8 h after the first dose on day 1 and after the last dose on day 15, with 24-h trough levels monitored on days 2, 4, 8, 11 and 16, and a 48-h trough on day 17. Plasma concentrations of mCyd, mUrd and Val-mCyd were measured by a HPLC/MS/MS methodology with a lower limit of quantitation (LOQ) at 20 ng/ml.

The pharmacokinetics of mCyd was analyzed using a non-compartmental approach. As presented in the tables below, the principal pharmacokinetic parameters were comparable on day 1 and day 15, indicative of no plasma drug accumulation after repeated dosing. The plasma exposure also appeared to be a linear function of dose. As shown in the tables below, principal pharmacokinetic parameters of drug exposure (Cmax and AUC) doubled as doses escalated from 50 to 100 mg.

TABLE 13

Pharmacokinetic parameters of mCyd at 50 mg

| Parameters | $C_{max}$ (ng/ml) | $T_{max}$ (h) | $AUC_{0-inf}$ (ng/ml × h) | $t_{1/2}$ (h) |
|---|---|---|---|---|
| Day 1 | | | | |
| Mean | 428.1 | 2.5 | 3118.7 | 4.1 |
| SD | 175.5 | 1.1 | 1246.4 | 0.6 |
| CV % | 41.0 | 43.2 | 40.0 | 13.8 |
| Day 15 | | | | |
| Mean | 362.7 | 2.2 | 3168.4 | 4.6 |
| SD | 165.7 | 1.0 | 1714.8 | 1.3 |
| CV % | 45.7 | 46.9 | 54.1 | 28.6 |

TABLE 14

Pharmacokinetic parameters of mCyd at 100 mg

| Parameters | $C_{max}$ (ng/ml) | $T_{max}$ (h) | $AUC_{0-inf}$ (ng/ml × h) | $t_{1/2}$ (h) |
|---|---|---|---|---|
| Day 1 | | | | |
| Mean | 982.1 | 2.6 | 6901.7 | 4.4 |
| SD | 453.2 | 1.0 | 2445.7 | 1.1 |
| CV % | 46.1 | 36.2 | 35.4 | 25.2 |
| Day 15 | | | | |
| Mean | 1054.7 | 2.0 | 7667.5 | 4.2 |
| SD | 181.0 | 0.0 | 1391.5 | 0.5 |
| CV % | 17.2 | 0.0 | 18.1 | 11.7 |

Figure 10:
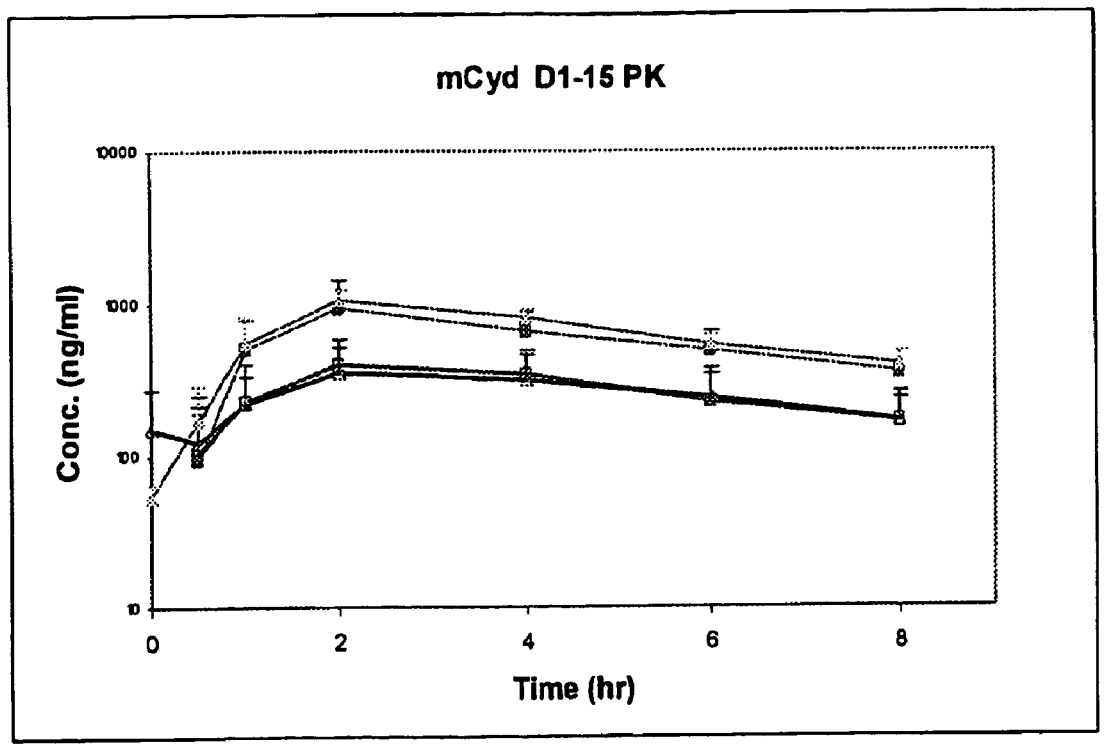
FIG. 10 is a graph of the concentration (ng/ml) of β-D-2'-C-methyl-ribofuranosyl cytidine in human serum after administration of β-D-2'-C-methyl-ribofuranosyl cytidine-3'-O-L-valine ester to patients, as described in Example 17.

The mean day 1 and day 15 plasma kinetic profiles of mCyd at 50 and 100 mg are depicted in the FIG. 10.

In summary, following oral administration of val-mCyd, the parent compound mCyd was detectable in the plasma of HCV-infected subjects. mCyd exhibited linear plasma pharmacokinetics in these subjects across the two dose levels thus far examined. There was no apparent accumulation of mCyd in subjects' plasma following 15 days of daily dosing at the doses thus far examined.

Antiviral Activity of mCyd after Oral Administration of Escalating Doses of Val-mCyd Starting at 50 mg/Day for 15 Days in HCV-Infected Patients Serum HCV RNA levels were determined with the use of the Amplicor HCV Monitor™ assay v2.0 (Roche Molecular Systems, Branchburg, N.J., USA), which utilizes polymerase chain reaction (PCR) methods. The lower limit of quantification (LLOQ) with this assay was estimated to be approximately 600 IU/mL and the upper limit of quantification (ULOQ) with this assay was estimated to be approximately 500,000 IU/mL.

Serum samples for HCV RNA were obtained at screening (Day −42 to −7) to determine eligibility for the study. The Screening serum HCV RNA values must be 5 $\log_{10}$ IU/mL by the Amplicor HBV Monitor™ assay at the central study laboratory.

During the study period, serum samples for HCV RNA were obtained at Baseline (Day 1), and at every protocol-stipulated post-Baseline study visit (Days 2, 4, 8, 11, 15, 16, 17, 22, and 29). Serum samples for HCV RNA were also collected during protocol-stipulated follow-up visits for patients prematurely discontinued from the study.

The antiviral activity associated with the first two cohorts (50 and 100 mg per day) in the ongoing study is summarized in the following tables and graphs. Although the duration of dosing was short (15 days) and the initial dose levels low, there were already apparent effects on the levels of HCV RNA in the plasma of infected patients.

TABLE 15

Summary Statistics of HCV RNA in $\log_{10}$ Scale

| Treatment | | −1 | 1 | 2 | 4 | 8 | 11 | 15 | 16 | 17 | 22 | 29 |
|---|---|---|---|---|---|---|---|---|---|---|---|---|
| Placebo | N | 6 | 5 | 5 | 4 | 4 | 4 | 4 | 4 | 3 | 4 | 3 |
| | Median | 6.45 | 6.25 | 6.25 | 6.52 | 6.42 | 6.28 | 6.58 | 6.51 | 6.64 | 6.35 | 6.61 |
| | Mean | 6.45 | 6.28 | 6.40 | 6.48 | 6.36 | 6.34 | 6.54 | 6.52 | 6.50 | 6.40 | 6.40 |
| | StdErr | 0.25 | 0.12 | 0.15 | 0.18 | 0.24 | 0.16 | 0.11 | 0.19 | 0.31 | 0.23 | 0.30 |
| 50 mg | N | 10 | 10 | 10 | 10 | 10 | 10 | 10 | 10 | 10 | 10 | 10 |
| | Median | 6.81 | 6.69 | 6.58 | 6.55 | 6.56 | 6.46 | 6.57 | 6.45 | 6.54 | 6.73 | 6.67 |
| | Mean | 6.72 | 6.72 | 6.60 | 6.56 | 6.62 | 6.47 | 6.57 | 6.57 | 6.54 | 6.64 | 6.71 |
| | StdErr | 0.11 | 0.11 | 0.12 | 0.06 | 0.10 | 0.09 | 0.08 | 0.11 | 0.08 | 0.10 | 0.09 |
| 100 mg | N | 11 | 10 | 10 | 10 | 9 | 10 | 10 | 9 | 9 | 10 | 4 |
| | Median | 6.75 | 6.93 | 6.80 | 6.46 | 6.59 | 6.56 | 6.41 | 6.40 | 6.72 | 6.66 | 6.71 |
| | Mean | 6.60 | 6.68 | 6.52 | 6.43 | 6.42 | 6.36 | 6.30 | 6.23 | 6.65 | 6.53 | 6.67 |
| | StdErr | 0.16 | 0.24 | 0.23 | 0.21 | 0.24 | 0.22 | 0.22 | 0.23 | 0.16 | 0.18 | 0.17 |

TABLE 16

Summary Statistics of Change From Baseline (Day 1) in $\log_{10}$ HCV RNA

| Treatment | | 2 | 4 | 8 | 11 | 15 | 16 | 17 | 22 | 29 |
|---|---|---|---|---|---|---|---|---|---|---|
| Placebo | N | | | | | | | | | |
| | Median | 0.17 | 0.21 | 0.15 | 0.08 | 0.31 | 0.21 | 0.27 | 0.17 | 0.09 |
| | Mean | 0.12 | 0.22 | 0.10 | 0.08 | 0.28 | 0.25 | 0.15 | 0.14 | 0.09 |
| | StdErr | 0.09 | 0.12 | 0.16 | 0.06 | 0.15 | 0.10 | 0.18 | 0.09 | 0.16 |

TABLE 16-continued

Summary Statistics of Change From Baseline (Day 1) in Log$_{10}$ HCV RNA

| Treatment | | Day | | | | | | | | |
|---|---|---|---|---|---|---|---|---|---|---|
| | | 2 | 4 | 8 | 11 | 15 | 16 | 17 | 22 | 29 |
| 50 mg | N | 10 | 10 | 10 | 10 | 10 | 10 | 10 | 10 | 10 |
| | Median | −0.07 | −0.13 | −0.06 | −0.26 | −0.10 | −0.13 | −0.21 | −0.09 | −0.04 |
| | Mean | −0.13 | −0.16 | −0.11 | −0.26 | −0.15 | −0.15 | −0.18 | −0.09 | −0.01 |
| | StdErr | 0.05 | 0.07 | 0.05 | 0.06 | 0.08 | 0.05 | 0.07 | 0.06 | 0.10 |
| 100 mg | N | 10 | 10 | 9 | 10 | 10 | 9 | 9 | 10 | 4 |
| | Median | −0.12 | −0.24 | −0.20 | −0.28 | −0.43 | −0.49 | −0.24 | −0.19 | −0.12 |
| | Mean | −0.16 | −0.25 | −0.21 | −0.32 | −0.38 | −0.39 | −0.18 | −0.15 | 0.13 |
| | StdErr | 0.07 | 0.10 | 0.16 | 0.13 | 0.12 | 0.14 | 0.15 | 0.13 | 0.28 |

Figure 11:
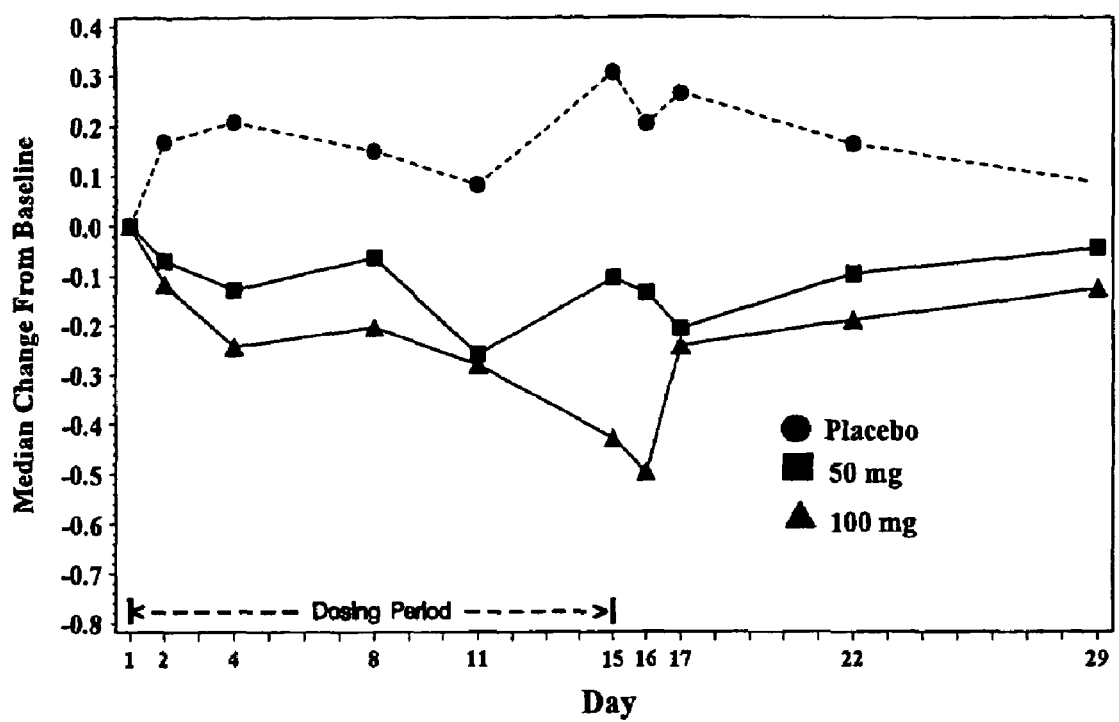
FIG. 11 is a graph of the median change of the titer of hepatitis C virus in human patients after administration of β-D-2'-C-methyl-ribofuranosyl cytidine-3'-O-L-valine ester, as described in Example 17. The graph indicates change from baseline in $Log_{10}$ HCV RNA by patient visit.

FIG. 11 Depicts the Median Change from Baseline In Log$_{10}$ HCV RNA by Visit

The present invention is described by way of illustration in the following examples. It will be understood by one of ordinary skill in the art that these examples are in no way limiting and that variations of detail can be made without departing from the spirit and scope of the present invention.

We claim:

1. A method of treating a host infected with a Flaviviridae virus, comprising administering to the host an effective amount of a compound having the structure of the formula:

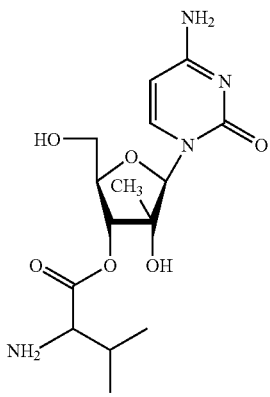

or a pharmaceutically acceptable salt or prodrug thereof optionally in a pharmaceutically acceptable carrier.

2. The method according to claim 1, wherein the pharmaceutically acceptable salt is a hydrochloride salt.

3. The method according to claim 1, wherein the pharmaceutically acceptable salt is a dihydrochloride salt.

4. The method according to claim 1, further comprising administering the compound in a pharmaceutically acceptable carrier, diluent or excipient.

5. The method according to claim 1, wherein the compound is administered in combination or alternation with a second anti-viral agent.

6. The method according to claim 5, wherein the second antiviral agent is selected from the group consisting of an interferon, ribavirin, an interleukin, a NS3 protease inhibitor, a cysteine protease inhibitor, thiazolidine derivative, thiazolidine, benzanilide, phenan-threnequinone, a helicase inhibitor, a polymerase inhibitor, a nucleoside analogue, gliotoxin, cerulenin, antisense phosphorothioate oligodeoxynucleotides, an inhibitor of IRES-dependent translation, and a ribozyme.

7. The method according to claim 5, wherein the second antiviral agent is an interferon.

8. The method according to claim 7, wherein the second agent is selected from the group consisting of pegylated interferon alpha 2a, interferon alphacon-1, natural interferon, albuferon, interferon beta-1a, omega interferon, interferon alpha, interferon gamma, interferon tau, interferon delta and interferon gamma-1b.

9. The method of claim 8, wherein the second antiviral agent is interferon alpha 2.

10. The method of claim 1, wherein the host is a human.

11. The method of claim 1, wherein the compound is in the form of a dosage unit.

12. The method of claim 11, wherein the dosage unit contains 70 to 1400 mg of the compound.

13. The method of claim 11, wherein the dosage unit is a tablet or capsule.

14. The method of any one of claims 1-3, wherein the pharmaceutically acceptable carrier is suitable for oral or intravenous delivery.

15. The method of any one of claims 1-3, wherein the compound is administered in substantially pure form.

16. The method of any one of claims 1-3, wherein the compound is at least 90% by weight of the β-D-isomer.

17. The method of any one of claims 1-3, wherein the compound is at least 95% by weight of the β-D-isomer.

18. The method of any one of claims 1-3, wherein the virus is hepatitis C.

19. A method for treating a host infected with an RNA-dependant RNA polymerase virus, comprising administering an effective amount of the compound of the formula:

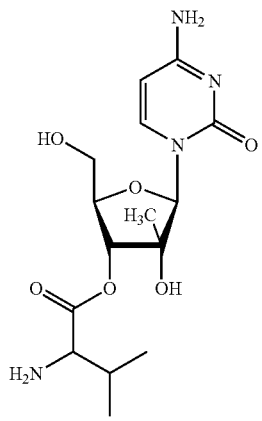

or its mono or dihydrochloride in pharmaceutically acceptable carrier, wherein the 5'-hydroxyl group is replaced with a 5'-OR, wherein R is hydrogen, phosphate; a stabilized phosphate prodrug; acyl; an amino acid; a carbohydrate; a peptide; or other pharmaceutically acceptable leaving group which when administered in viva provides a compound wherein R is independently H or phosphate.

20. The method of claim 19 wherein the virus is a F/aviviridae virus.

21. The method of claim 19 or 20 wherein the Flaviviridae virus is hepatitis C.

22. The method of claim 19 or 20 wherein the host is a human.

23. The method of claim 1, wherein the pharmaceutically acceptable salt is selected from tosylate, methanesulfonate, acetate, citrate, malonate, tartarate, succinate, benzoate, ascorbate, α-ketoglutarate, and α-glycerophosphate, formate, fumarate, propionate, glycolate, lactate, pyruvate, oxalate, maleate, salicyate, sulfate, sulfonate, nitrate, hydrobromate, hydrobromide, hydroiodide, and phosphoric acid salts.

24. The method of claim 19, wherein the compound or a pharmaceutically acceptable salt thereof, is administered in combination with a pharmaceutically acceptable carrier.

25. The method of claim 24, wherein the carrier is suitable for oral or intravenous delivery.

26. The method of claim 19, wherein the compound is in the form of a dosage unit.

27. The method of claim 19, wherein the compound is administered in substantially pure form.

28. The method of claim 19, wherein the compound is at least 90% by weight of the β-D-isomer.

29. The method of claim 19, wherein the compound is at least 95% by weight of the β-D-isomer.

30. The method of claim 11 or 26, wherein the dosage unit contains 50 mg to 1000 mg of the compound.

31. The method of claim 11 or 26, wherein the dosage unit contains 100 mg of the compound.

32. The method of claim 11 or 26, wherein the dosage unit contains 200 mg of the compound.

33. The method of claim 11 or 26, wherein the dosage unit contains 400 mg of the compound.

34. The method of claim 11 or 26, wherein the dosage unit contains 800 mg of the compound.

35. The method of claim 11 or 26, wherein the dosage unit contains 1000 mg of the compound.

36. The method of claim 21 wherein the host is a human.

* * * * *